(12) United States Patent
Berez et al.

(10) Patent No.: US 8,409,267 B2
(45) Date of Patent: *Apr. 2, 2013

(54) VASCULAR STENTING FOR ANEURYSMS

(75) Inventors: Aaron L. Berez, Menlo Park, CA (US); Quang Q. Tran, Redwood City, CA (US)

(73) Assignee: Covidien LP, Mansfield, MA (US)

( * ) Notice: Subject to any disclaimer, the term of this patent is extended or adjusted under 35 U.S.C. 154(b) by 112 days.

This patent is subject to a terminal disclaimer.

(21) Appl. No.: 12/431,716

(22) Filed: Apr. 28, 2009

(65) Prior Publication Data

US 2009/0270974 A1    Oct. 29, 2009

(51) Int. Cl.
*A61F 2/06* (2006.01)

(52) U.S. Cl. ...................................................... 623/1.11

(58) Field of Classification Search ................ 623/1.11, 623/1.15, 1.16, 1.12, 1.4, 1.5, 1.51, 1.53, 623/1.17–1.22

See application file for complete search history.

(56) References Cited

U.S. PATENT DOCUMENTS

| | | |
|---|---|---|
| 4,954,126 A | 9/1990 | Wallsten |
| 5,951,599 A | 9/1999 | McCrory |
| 6,264,671 B1 | 7/2001 | Stack et al. |
| 6,497,711 B1 | 12/2002 | Plaia et al. |
| 6,613,078 B1 * | 9/2003 | Barone ........................ 623/1.13 |
| 6,652,574 B1 | 11/2003 | Jayaraman |
| 6,702,843 B1 | 3/2004 | Brown et al. |
| 7,235,096 B1 | 6/2007 | Van Tassel et al. |
| RE40,816 E | 6/2009 | Taylor et al. |
| 2002/0138133 A1 * | 9/2002 | Lenz et al. ................... 623/1.15 |
| 2003/0135258 A1 | 7/2003 | Andreas et al. |
| 2004/0133223 A1 | 7/2004 | Weber |
| 2004/0186368 A1 | 9/2004 | Ramzipoor et al. |
| 2006/0116713 A1 | 6/2006 | Septka |
| 2006/0184238 A1 | 8/2006 | Kaufmann et al. |
| 2006/0206201 A1 | 9/2006 | Garcia et al. |
| 2006/0271153 A1 | 11/2006 | Garcia et al. |
| 2007/0021816 A1 | 1/2007 | Rudin |
| 2007/0055365 A1 | 3/2007 | Greenberg et al. |
| 2007/0239261 A1 * | 10/2007 | Bose et al. ................... 623/1.15 |
| 2010/0076317 A1 | 3/2010 | Babic |
| 2011/0040372 A1 | 2/2011 | Hansen |

OTHER PUBLICATIONS

International Search Report and Written Opinion for International Application No. PCT/US2010/031092, mailed on Jun. 16, 2010, in 20 pages.

Vanninen, et al., "Broad Based Intracranial Aneurysms: Thrombosis Induced by Stent Placement", Am J Neuroradiol, 24: 263-6 (2003).

* cited by examiner

*Primary Examiner* — Thomas McEvoy

(74) *Attorney, Agent, or Firm* — Mark J. Kertz, Esq.

(57) ABSTRACT

Described herein are flexible implantable occluding devices that can, for example, navigate the tortuous vessels of the neurovasculature. The occluding devices can also conform to the shape of the tortuous vessels of the vasculature. In some embodiments, the occluding devices can direct blood flow within a vessel away from an aneurysm or limit blood flow to the aneurysm. Some embodiments describe methods and apparatus for adjusting, along a length of the device, the porosity of the occluding device. In some embodiments, the occluding devices allows adequate blood flow to be provided to adjacent structures such that those structures, whether they are branch vessels or oxygen-demanding tissues, are not deprived of the necessary blood flow.

15 Claims, 58 Drawing Sheets

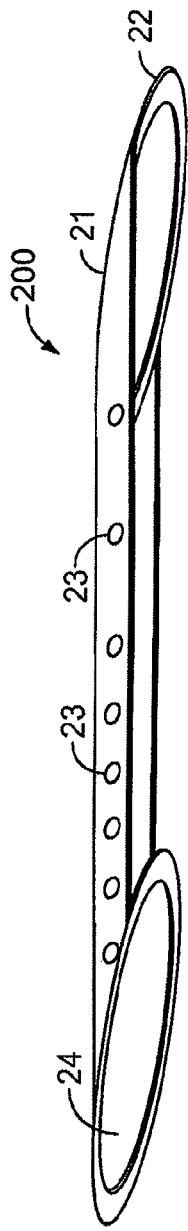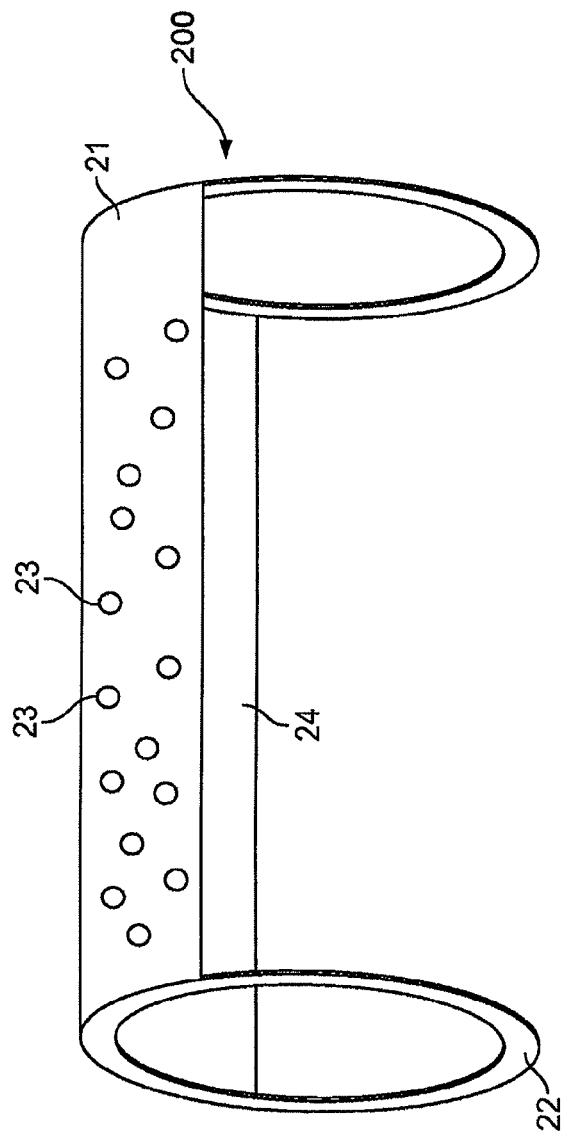
FIG. 2A
FIG. 2B

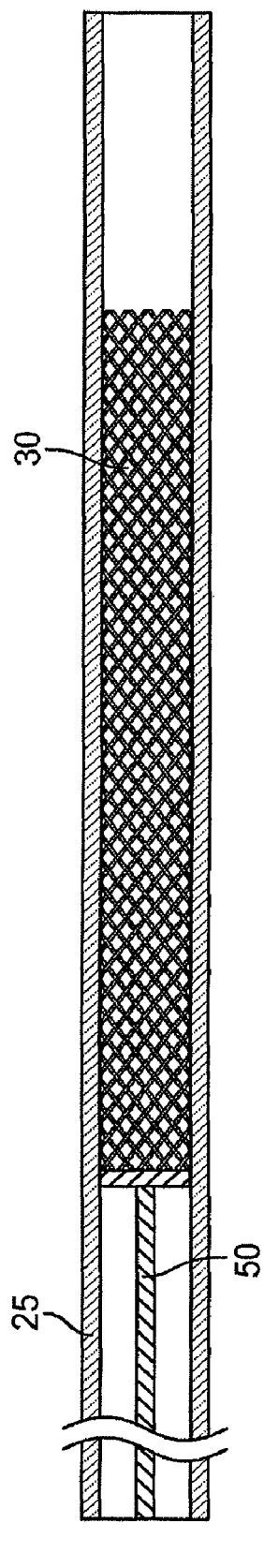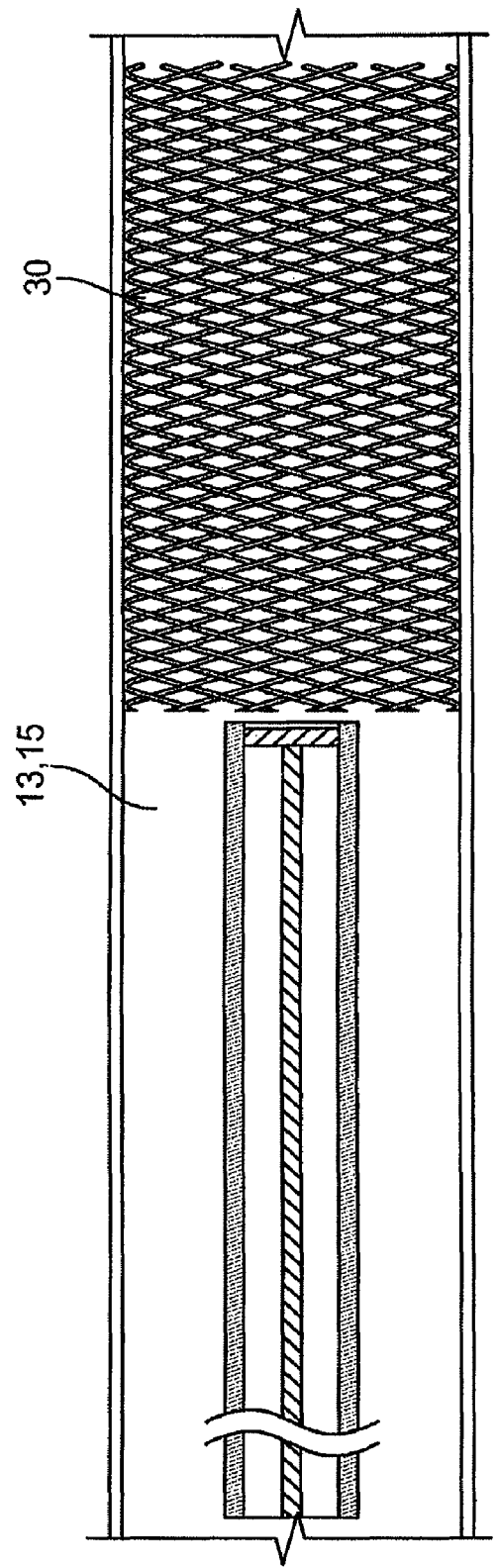

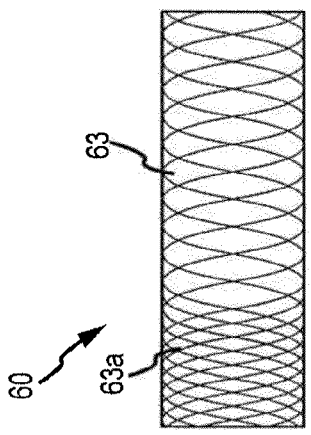
FIG.11B
FIG.11C
FIG.11D
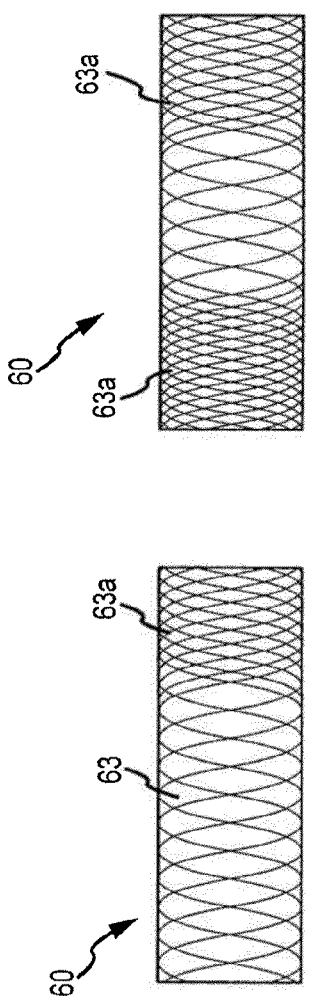
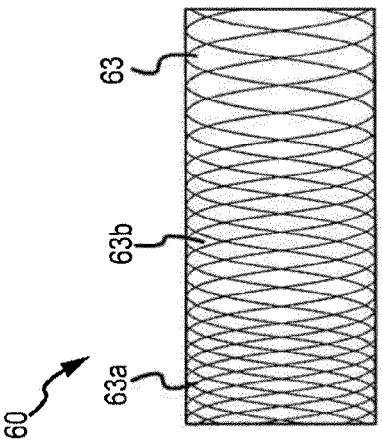
FIG.11E
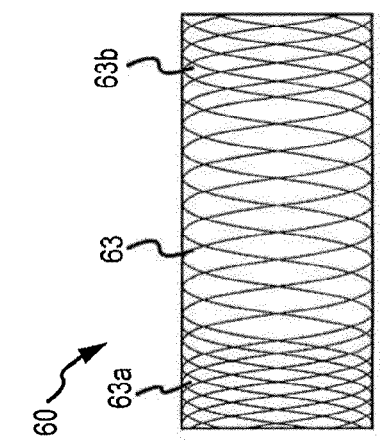
FIG.11F
FIG.11G

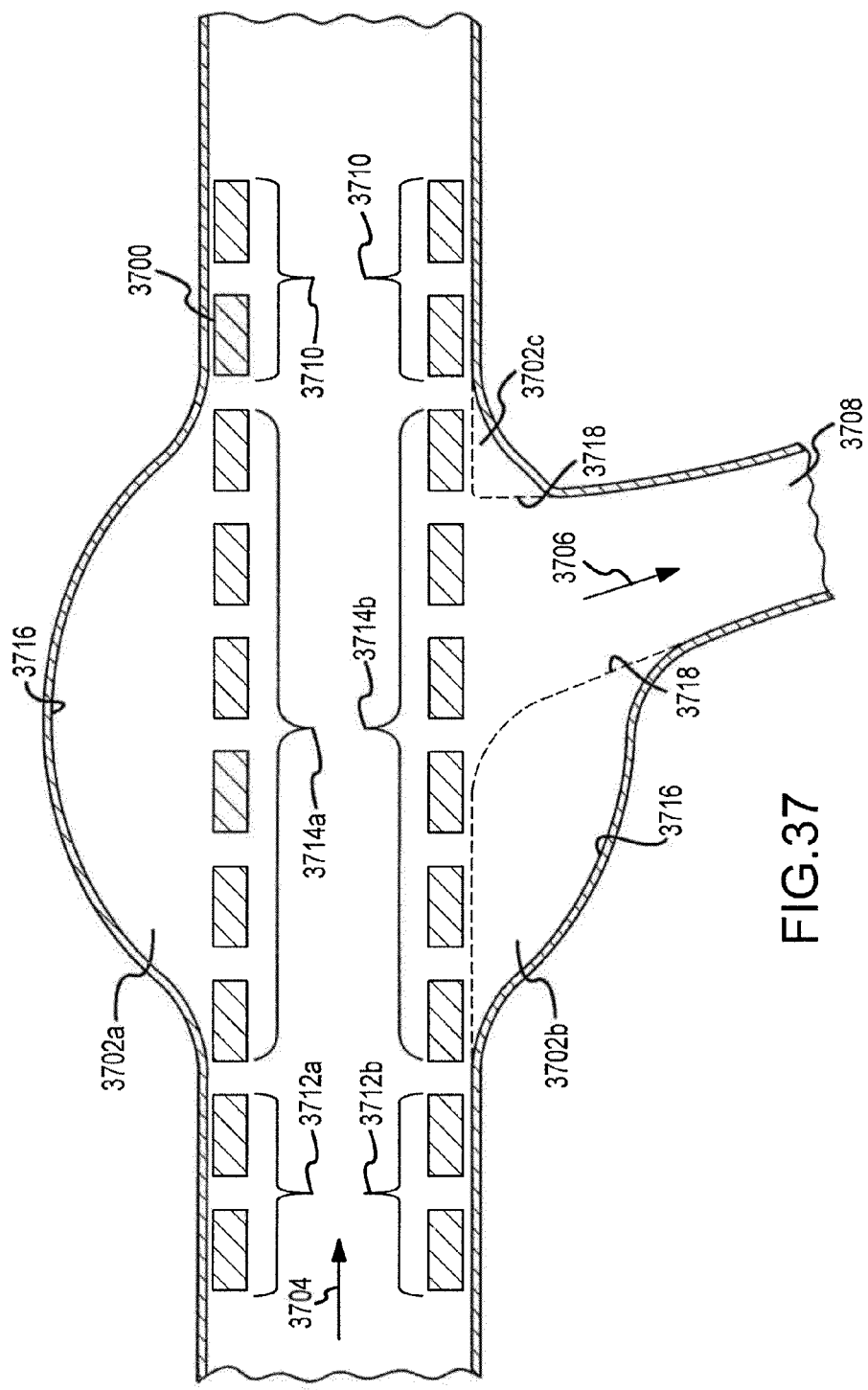

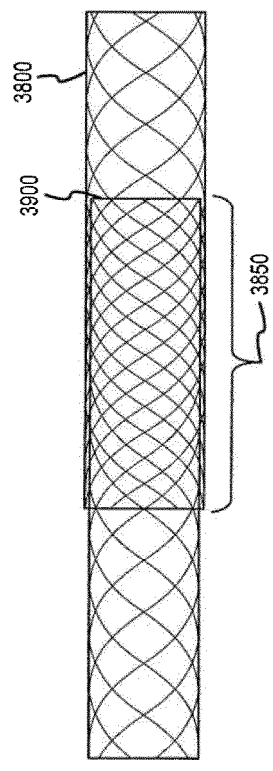
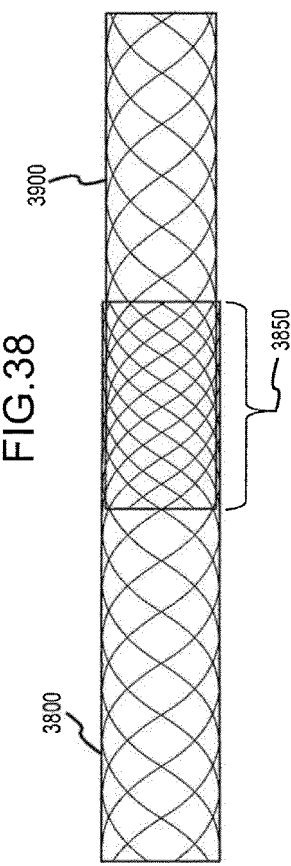
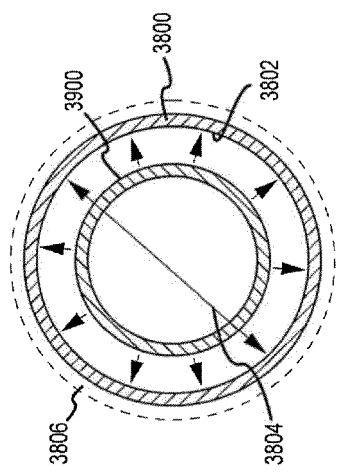
FIG.38
FIG.39
FIG.40

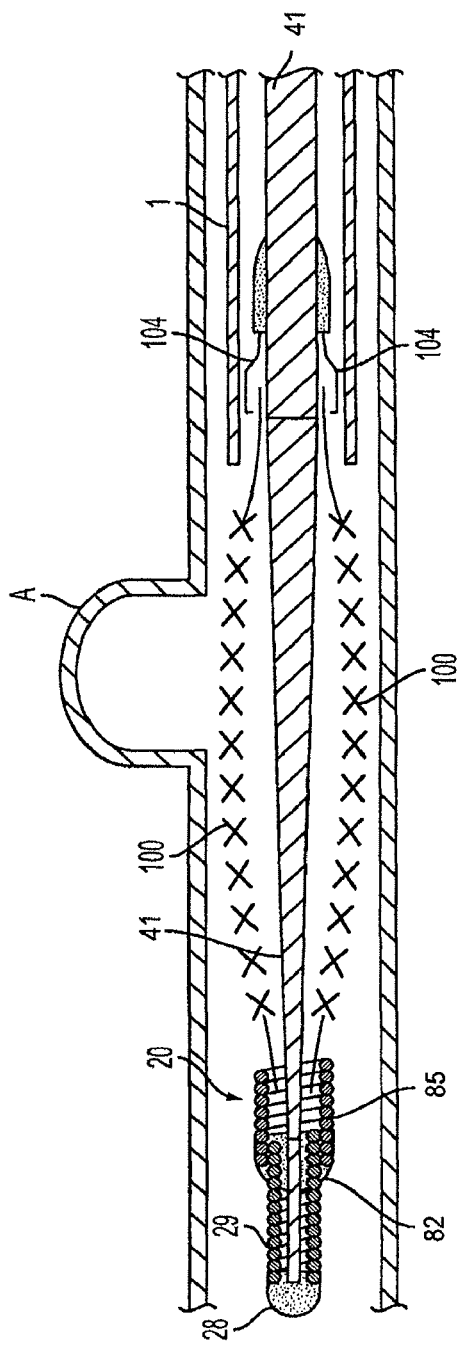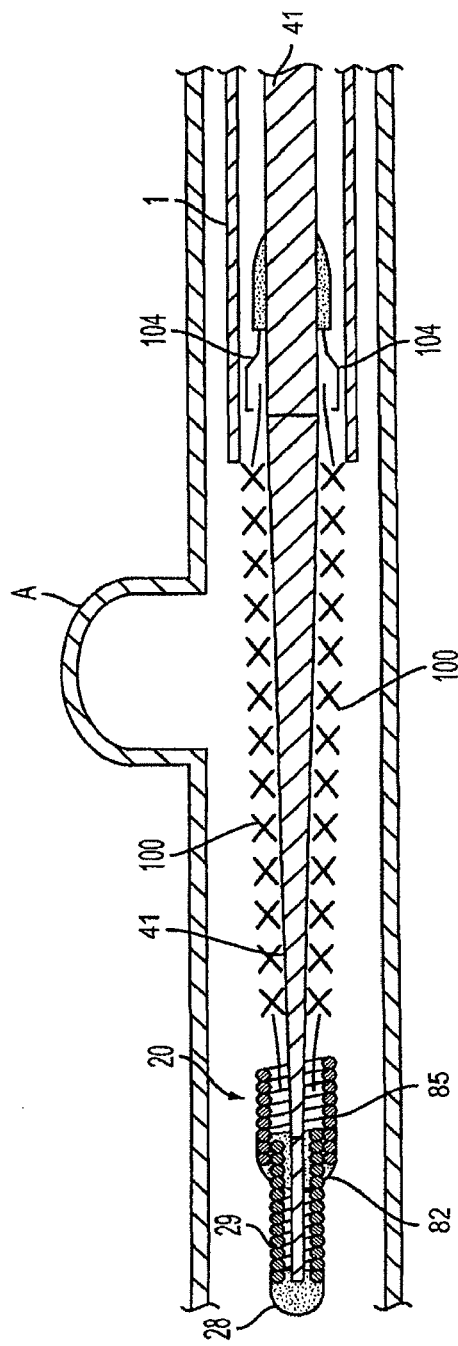

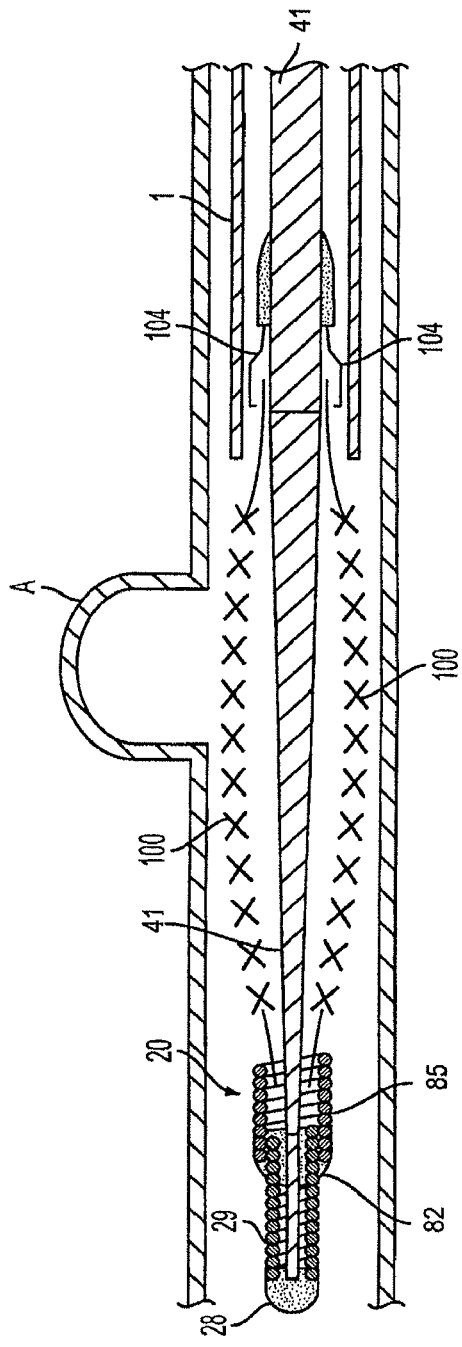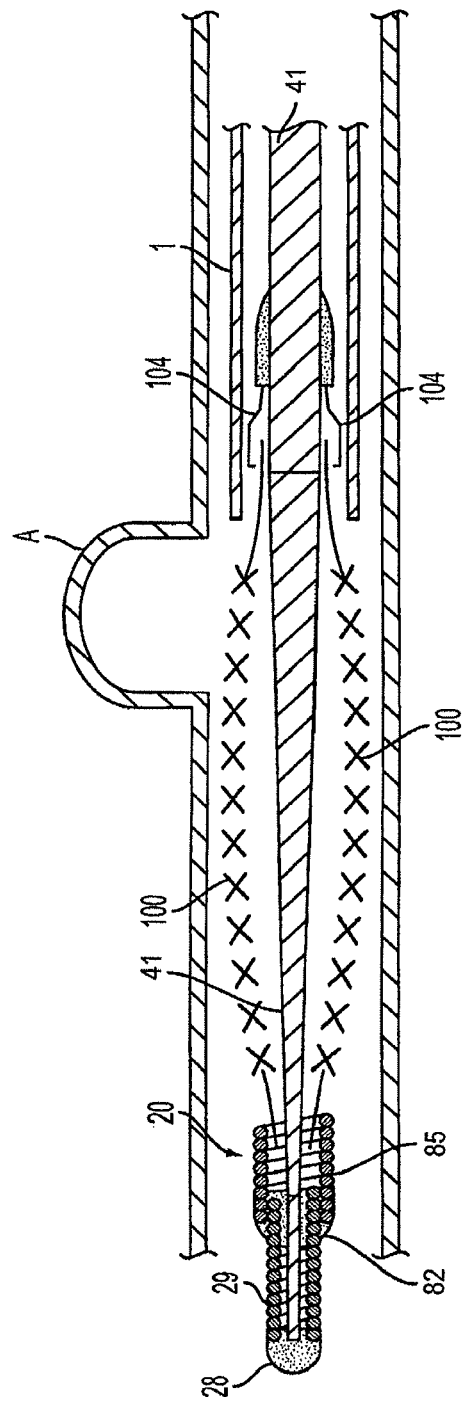

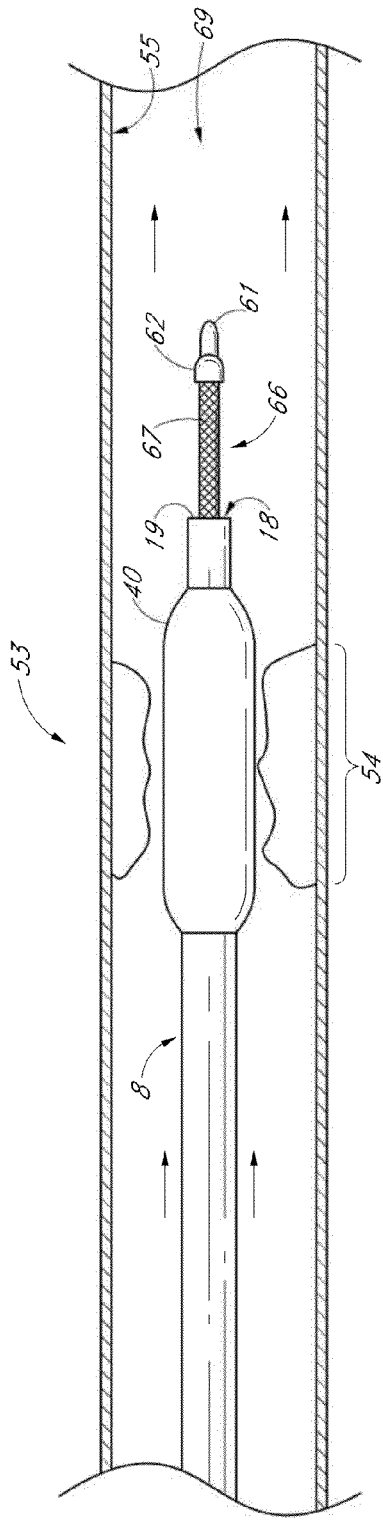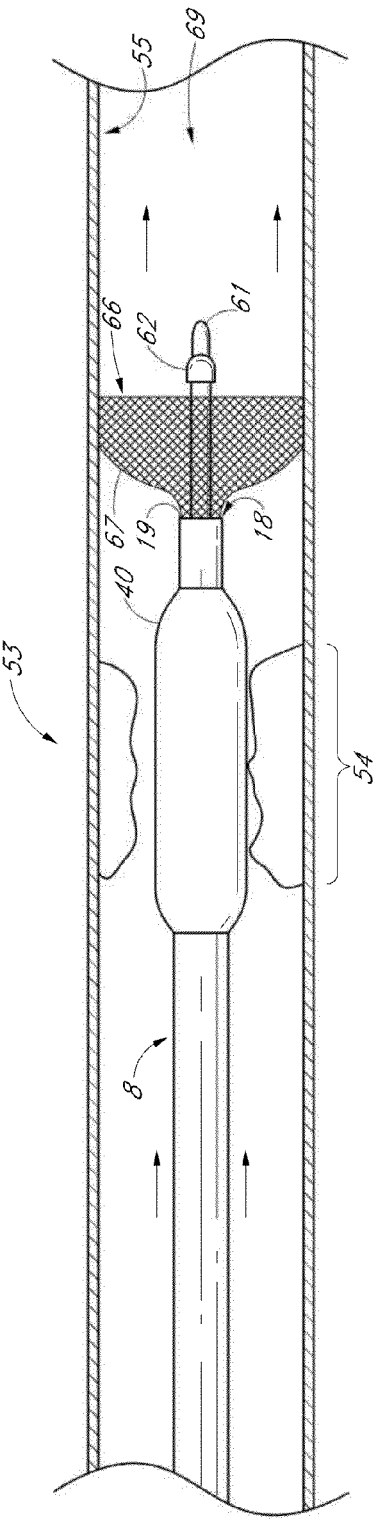
FIG. 65
FIG. 66

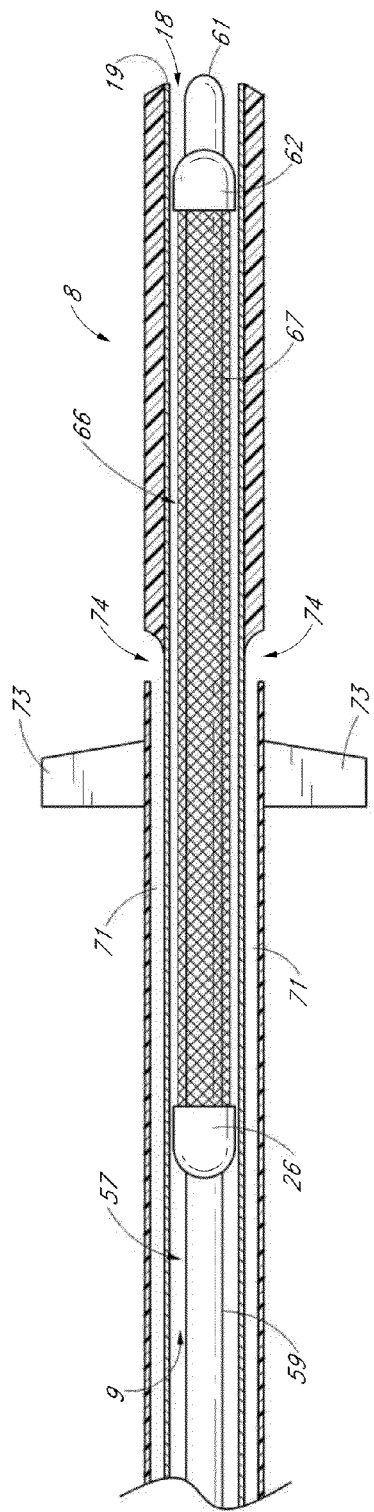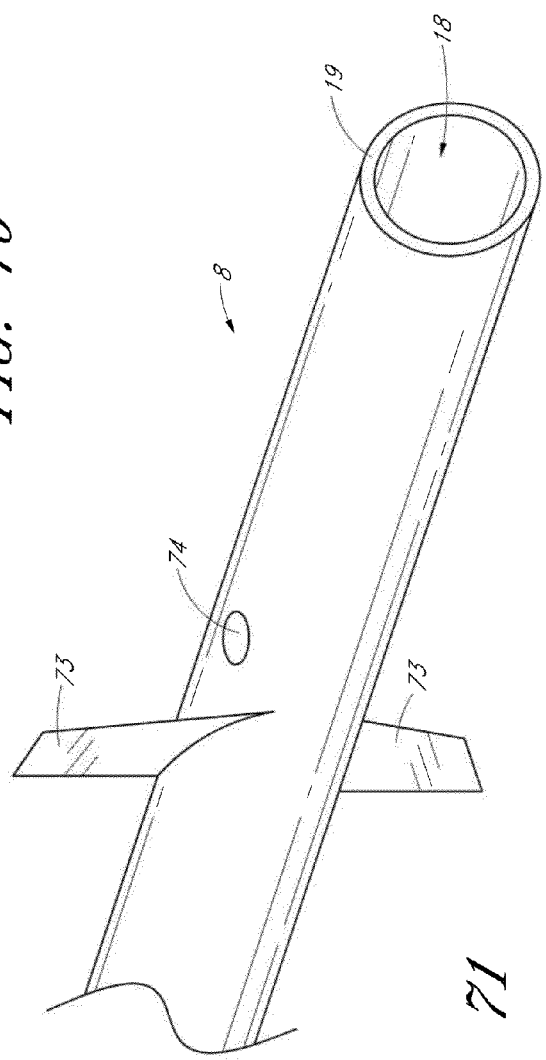
FIG. 70
FIG. 71

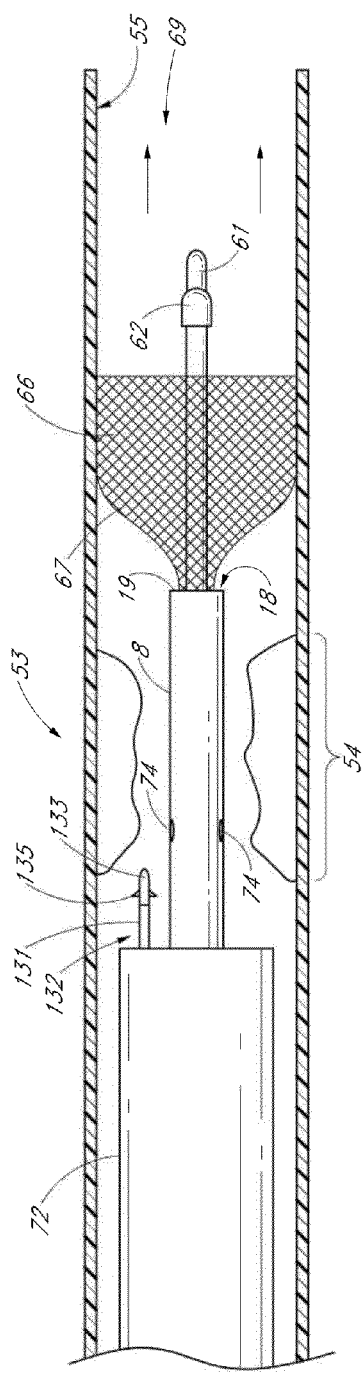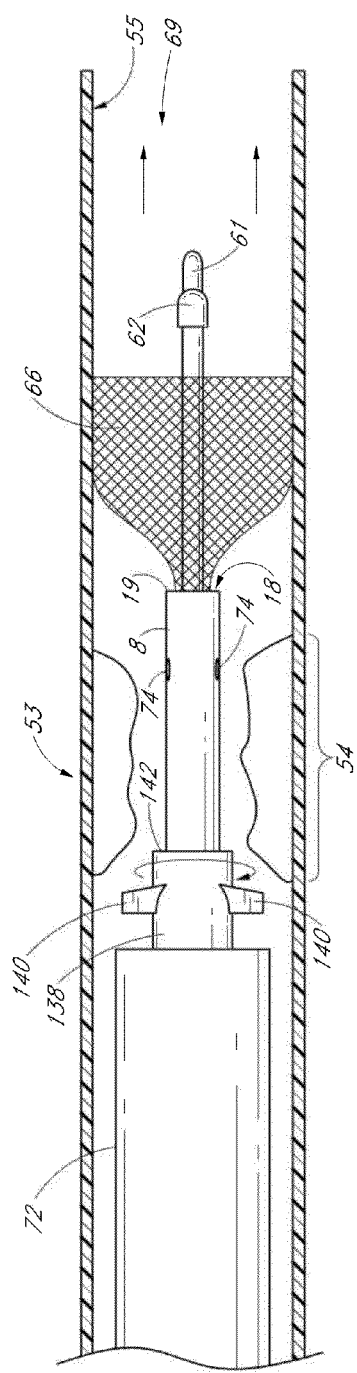

VASCULAR STENTING FOR ANEURYSMS

STATEMENT AS TO RIGHTS TO INVENTIONS MADE UNDER FEDERALLY SPONSORED RESEARCH OR DEVELOPMENT

Not Applicable.

FIELD

The subject technology generally relates to implantable devices for use within a patient's body and, in particular, relates to methods and apparatus for luminal stenting.

BACKGROUND

Lumens in the body can change in size, shape, and/or patency, and such changes can present complications or affect associated body functions. For example, the walls of the vasculature, particularly arterial walls, may develop pathological dilatation called an aneurysm. Aneurysms are observed as a ballooning-out of the wall of an artery. This is a result of the vessel wall being weakened by disease, injury or a congenital abnormality. Aneurysms have thin, weak walls and have a tendency to rupture and are often caused or made worse by high blood pressure. Aneurysms could be found in different parts of the body; the most common being abdominal aortic aneurysms (AAA) and the brain or cerebral aneurysms. The mere presence of an aneurysm is not always life-threatening, but they can have serious heath consequences such as a stroke if one should rupture in the brain. Additionally, a ruptured aneurysm can also result in death.

SUMMARY

An aspect of the disclosure provides a highly flexible implantable occluding device that can easily navigate the tortuous vessels of the neurovasculature. Additionally, occluding device can easily conform to the shape of the tortuous vessels of the vasculature. Furthermore, the occluding device can direct the blood flow within a vessel away from an aneurysm; additionally such an occluding device allows adequate blood flow to be provided to adjacent structures such that those structures, whether they are branch vessels or oxygen demanding tissues, are not deprived of the necessary blood flow.

The occluding device is also capable of altering blood flow to the aneurysm, yet maintaining the desired blood flow to the surrounding tissue and within the vessel. In this instance, some blood is still allowed to reach the aneurysm, but not enough to create a laminar flow within the aneurysm that would cause injury to its thinned walls. Instead, the flow would be intermittent, thereby providing sufficient time for blood clotting or filler material curing within the aneurysm.

The occluding device is flexible enough to closely approximate the native vasculature and conform to the natural tortuous path of the native blood vessels. One of the significant attributes of the occluding device according to the present disclosure is its ability to flex and bend, thereby assuming the shape of a vasculature within the brain. These characteristics are for a neurovascular occluding device than compared to a coronary stent, as the vasculature in the brain is smaller and more tortuous.

In general terms, aspects of the disclosure relate to methods and devices for treating aneurysms. In particular, a method of treating an aneurysm with a neck comprises deploying a vascular occluding device in the lumen of a vessel at the location of the aneurysm, whereby the blood flow is redirected away from the neck of the aneurysm. The induced stagnation of the blood in the lumen of the aneurysm would create embolization in the aneurysm. The occluding device spans the width of the stem of the aneurysm such that it obstructs or minimizes the blood flow to the aneurysm. The occluding device is very flexible in both its material and its arrangement. As a result, the occluding device can be easily navigated through the tortuous blood vessels, particularly those in the brain. Because the occluding device is flexible, very little force is required to deflect the occluding device to navigate through the vessels of the neurovasculature, which is of significance to the operating surgeon.

A feature of the occluding device, apart from its flexibility, is that the occluding device may have an asymmetrical braid pattern with a higher concentration of braid strands or a different size of braid strands on the surface facing the neck of the aneurysm compared to the surface radially opposite to it. In one embodiment, the surface facing the aneurysm is almost impermeable and the diametrically opposed surface is highly permeable. Such a construction would direct blood flow away from the aneurysm, but maintain blood flow to the side branches of the main vessel in which the occluding device is deployed.

In another embodiment, the occluding device has an asymmetrical braid count along the longitudinal axis of the occluding device. This provides the occluding device with a natural tendency to curve, and hence conform to the curved blood vessel. This reduces the stress exerted by the occluding device on the vessel wall and thereby minimizing the chances of aneurysm rupture. Additionally, because the occluding device is naturally curved, this eliminates the need for the tip of the catheter to be curved. Now, when the curved occluding device is loaded on to the tip of the catheter, the tip takes the curved shape of the occluding device. The occluding device could be pre-mounted inside the catheter and can be delivered using a plunger, which will push the occluding device out of the catheter when desired. The occluding device could be placed inside the catheter in a compressed state. Upon exiting the catheter, it could expand to the size of the available lumen and maintain patency of the lumen and allow blood flow through the lumen. The occluding device could have a lattice structure and the size of the openings in the lattice could vary along the length of the occluding device. The size of the lattice openings can be controlled by the braid count used to construct the lattice.

According to one aspect of the disclosure, the occluding device can be used to remodel an aneurysm within the vessel by, for example, neck reconstruction or balloon remodeling. The occluding device can be used to form a barrier that retains occlusion material within the aneurysm so that introduced material will not escape from within the aneurysm due to the lattice density of the occluding device in the area of the aneurysm.

In another aspect of the disclosure, a device for occluding an aneurysm is disclosed. The device is a tubular with a plurality of perforations distributed on the wall of the member. The device is placed at the base of the aneurysm covering the neck of the aneurysm such that the normal flow to the body of the aneurysm is disrupted and thereby generating thrombus and ultimately occlusion of the aneurysm.

In yet another aspect of this disclosure, the device is a braided tubular member. The braided strands are ribbons with rectangular cross section, wires with a circular cross section or polymeric strands.

In another embodiment, a device with a braided structure is made in order to conform to a curved vessel in the body, where the density of the braid provides enough rigidity and radial strength. Additionally, the device can be compressed using a force less than 10 grams. This enables the device to be compliant with the artery as the arterial wall is pulsating. Also, the device is capable of bending upon applying a force of less than 5 gram/cm.

In another aspect, the device may include an occluding device having a first lattice density in one portion and a second lattice density in a second portion, the first and second lattice densities being different. In another example, the first lattice density and/or the second lattice density may be adjusted. For example, an input motion may determine the first and/or lattice density.

Aspects of the disclosure include a system and method of deploying an occluding device within a vessel. The occluding device can be used to remodel an aneurysm within the vessel by, for example, neck reconstruction or balloon remodeling. The occluding device can be used to form a barrier that retains occlusion material such as a well known coil or viscous fluids, such as "ONYX" by Microtherapeutics, within the aneurysm so that introduced material will not escape from within the aneurysm. Also, during deployment, the length of the occluding device can be adjusted in response to friction created between the occluding device and an inner surface of a catheter. When this occurs, the deployed length and circumferential size of the occluding device can be changed as desired by the physician performing the procedure.

An aspect of the disclosure includes a system for supporting and deploying an occluding device. The system comprises an introducer sheath and an assembly for carrying the occluding device. The assembly includes an elongated flexible member having an occluding device retaining member for receiving a first end of the occluding device, a proximally positioned retaining member for engaging a second end of the occluding device and a support surrounding a portion of the elongated flexible member over which the occluding device can be positioned.

Another aspect of the disclosure includes a system for supporting and deploying an occluding device. The system comprises an assembly for carrying the occluding device. The assembly comprises an elongated member including a flexible distal tip portion, a retaining member for receiving a first end of the occluding device, and a support surrounding a portion of the elongated flexible member for supporting the occluding device.

A further aspect of the disclosure comprises a method of introducing and deploying an occluding device within a vessel. The method includes the steps of introducing an elongated sheath including an introducer sheath carrying a guidewire assembly into a catheter and advancing the guidewire assembly out of the sheath and into the catheter. The method also includes the steps of positioning an end of the catheter proximate an aneurysm, advancing a portion of the guidewire assembly out of the catheter and rotating a portion of the guidewire assembly while deploying the occluding device in the area of the aneurysm.

In another aspect an elongated flexible member supports and deploys an occluding device and the occluding device may be expanded and retracted based on input pressure. For example, air of fluid pressure may be applied to the occluding device via the flexible member to cause the occluding device to expand or retract.

Other aspects of the disclosure include methods corresponding to the devices and systems described herein.

In some embodiments, methods, of implanting a stent in a patient's blood vessel, are described, including: providing an elongate body, the elongate body comprising a proximal portion, a distal portion, and a lumen extending between the proximal portion and the distal portion; inserting the distal portion in a blood vessel of a patient; advancing the distal portion within the blood vessel until the distal portion is at a target site; advancing, relative to the elongate body and within the lumen of the elongate body, a stent in a compressed configuration; allowing a distal portion of the stent to expand to an expanded configuration and contact a vessel wall as a distal portion of the stent is advanced out of the distal portion of the elongate body; and after the distal portion of the stent is in the expanded configuration and contacts the vessel wall, axially compressing the stent to change a porosity of the stent by advancing a proximal portion of the stent with respect to the distal portion of the stent.

In some embodiments, the methods further comprise positioning the stent at an aneurysm arising from the blood vessel. In some embodiments, axially compressing the stent decreases the porosity of the stent. In some embodiments, axially compressing the stent reduces blood flow to the vessel aneurysm. In some embodiments, after the allowing the distal portion to expand and axially compressing the stent, a proximal portion of the stent, proximal to the distal portion, is axially compressed more than the distal portion. In certain embodiments, the methods further include reducing the migration of blood clots from the aneurysm by decreasing the porosity of the stent adjacent the aneurysm.

Some embodiments further comprise compressing all or a part of the distal portion of the stent back into the compressed configuration after allowing the distal portion of the stent to expand in the vessel. In some embodiments, the distal portion of the stent is compressed by withdrawing all or a portion of the distal portion into the elongate body. In some embodiments, the distal portion of the stent is compressed by advancing the elongate body over the distal portion. Some embodiments further include moving the distal portion of the stent to a different location; advancing the stent, relative to the elongate body and within the lumen of the elongate body; and allowing a distal portion of the stent to automatically expand to an expanded configuration at the different location. Some embodiments further include removing the stent from the vessel.

Some embodiments of implanting a stent in a patient's vessel include providing a stent comprising a distal section and a proximal section and having a compressed configuration and an expanded configuration, the stent being configured to change from the compressed configuration to the expanded configuration and to have a variable porosity when in the expanded configuration; advancing the stent within the patient's vessel to a target site; expanding the distal section of the stent at the target site; varying a proximal section porosity with respect to a distal section porosity by advancing, after the expanding the distal section, the proximal section of the stent axially relative to the distal section; and expanding the proximal section of the stent in the patient's vessel.

Some embodiments further include positioning the stent at an aneurysm arising from the vessel. Some embodiments further include reducing the migration of blood clots from the aneurysm by decreasing a porosity of the proximal section, relative to the distal section porosity, adjacent the aneurysm. In some embodiments, the varying the proximal section porosity comprises decreasing the proximal section porosity with respect to the distal section porosity. In some embodiments, the varying the proximal section porosity reduces blood flow to the vessel aneurysm. In certain embodiments, after expanding the distal section and advancing the proximal section axially, a portion of the proximal section is axially compressed more than the distal section.

Some embodiments further include compressing the distal section of the stent back into the compressed configuration after expanding the distal section of the stent in the vessel. In some embodiments, the distal section of the stent is compressed by withdrawing the distal section into an elongate body. In some embodiments, the distal section of the stent is compressed by advancing an elongate body over the distal section. Some embodiments further include moving the distal section of the stent to a different location; and reexpanding the distal section of the stent within a vessel without removing the stent from the patient's vasculature.

Some embodiments of implanting a stent in a patient's vessel include providing a stent comprising a distal section and a proximal section and having a compressed configuration and an expanded configuration, the stent being configured to have an adjustable porosity; expanding the distal section of the stent in the patient's vessel such that the distal section has a first porosity; and adjusting the proximal section such that, when expanded within the patient's vessel, the proximal section has a second porosity different than the first porosity.

Some embodiments further include positioning the stent at an aneurysm arising from the vessel. Some embodiments further include reducing the migration of blood clots from the aneurysm by decreasing a porosity of the proximal section, relative to the distal section porosity, adjacent the aneurysm. In some embodiments, the adjusting the proximal section reduces blood flow to the vessel aneurysm. In some embodiments, the adjusting the proximal section comprises decreasing the proximal section porosity with respect to the distal section porosity. In some embodiments, after expanding the distal section and adjusting the proximal section, a portion of the proximal section is axially compressed more than the distal section. Some embodiments further include compressing the distal section of the stent back into the compressed configuration after expanding the distal section of the stent in the vessel.

Some embodiments of implanting a stent in a patient's vessel include advancing a stent in a vessel to a treatment site; expanding, on one side of the treatment site, a distal section of the stent in the vessel such that, after expanding, the distal section has a distal section wall with a first porosity; after expanding the distal section of the stent, adjusting a middle section of the stent such that, when adjusted, the middle section has a middle section wall having a second porosity less than the first porosity; and after adjusting the middle section, expanding a proximal section of the stent such that, after expanding, the proximal section has a proximal section wall having a third porosity.

Some embodiments further include positioning the stent at an aneurysm arising from the vessel. In some embodiments, the expanded middle section wall is positioned at the aneurysm. In some embodiments, the adjusting the middle section reduces blood flow to the vessel aneurysm. In some embodiments, the middle section wall second porosity is adjusted to be less than at least one of the first porosity and the third porosity. Some embodiments further include engaging the vessel with the distal section. In some embodiments, the expanding the proximal section comprises expanding the proximal section radially. Some embodiments further include engaging the vessel with the proximal section. In some embodiments, the second porosity is adjusted to be less than at least one of the first porosity and the third porosity.

Some embodiments further include returning the distal section of the stent to a contracted configuration, thereby reducing contact between the distal section and the vessel, after allowing the distal section to expand in the vessel. In some embodiments, the distal section of the stent is returned to the contracted configuration by withdrawing the distal section into the elongate body. In some embodiments, the distal section of the stent is returned to the contracted configuration by advancing an elongate body over the distal section. Some embodiments further include after returning the distal section of the stent to a contracted configuration, moving the distal section of the stent to a different location within the patient; and expanding the distal section of the stent at the different location. Some embodiments further include removing the stent from the vessel.

Some embodiments of implanting a stent in a patient's vessel include expanding a stent in the vessel, the stent having a wall with an adjustable porosity that, when unrestrained, has a first porosity; and adjusting the stent within the vessel such that a middle section of the wall has a second porosity different than the first porosity. In some embodiments, the second porosity is less than a third porosity of a proximal section of the wall and a fourth porosity of a distal section of the wall. Some embodiments further include positioning the stent at an aneurysm arising from the vessel. In some embodiments, the middle section is positioned and expanded at the aneurysm. In some embodiments, the second porosity is adjusted to be less than at least one of the first porosity, a third porosity of a proximal section of the wall, and a fourth porosity of a distal section of the wall. Some embodiments further include compressing the stent to a contracted configuration after expanding the stent in the vessel. In some embodiments, the stent compressed to the contracted configuration by withdrawing a distal section of the stent from the vessel into a delivery catheter. Some embodiments further include after compressing the stent to the contracted configuration, moving the stent to a different location within a vessel of the patient; and expanding the stent at the different location.

Some embodiments of treating a patient's vessel include advancing a stent into a patient's vessel, the stent having lumen extending between a proximal end of the stent and a distal end of the stent; expanding the stent from a first state, having a first cross-sectional dimension to a second state, having a second cross-sectional dimension greater than the first cross-sectional dimension, the stent having a second state stent length less than a first state stent length; and axially compressing a first portion of the stent to a third state, such that the stent has a third state stent length less than the second state stent length; wherein the expanding the stent from the first state comprises permitting the stent to axially compress and radially expand by unrestraining the stent; and wherein the axially compressing the first portion of the stent comprises applying an axially compressive force on the stent when the stent is in the second state.

Some embodiments further include permitting the stent to axially expand from the third state to the second state by unrestraining the stent. In some embodiments, the stent, in the third state, has a third cross-sectional dimension that is substantially the same as the second cross-sectional dimension.

Some embodiments relate to a stent, for implanting in a patient's vessel, that includes a proximal portion having a proximal end; a distal portion having a distal end; a stent length extending from the proximal end to the distal end; a stent wall that defines a lumen extending between the proximal end and the distal end, the stent wall having a delivery configuration and an expanded configuration; wherein, when in the expanded configuration, the stent wall has a porosity that is changeable in a discrete location proximal to the distal portion by changing the stent length.

In some embodiments, the porosity of the stent wall is decreased as the stent length is decreased. In some embodiments, as the stent length is changed, the stent wall porosity changes in the discrete location relative to the stent wall porosity in at least one of the proximal portion and the distal portion. In some embodiments, when the stent length is decreased, the porosity of the stent wall in the discrete location is reduced relative to the porosity of the stent wall in the proximal portion and the distal portion. In some embodiments, axially compressing the stent decreases the porosity of the stent. In some embodiments, the stent automatically changes from the delivery configuration to the expanded configuration when unrestrained.

In some embodiments, the stent is radially collapsible, after changing from the delivery configuration to the expanded configuration, by increasing the stent length. In some embodiments, the stent is radially collapsible, after changing from the delivery configuration to the expanded configuration, by advancement of a catheter over the expanded stent. In some embodiments, the stent comprises a first stent length when the stent is in the delivery configuration, and a second stent length, shorter than the first stent length, when the stent is in the expanded configuration. In some embodiments, the porosity of the stent can be reduced in the discrete location by decreasing the stent length beyond the second stent length. In some embodiments, when in the expanded configuration, the porosity is changeable in the discrete location by changing the stent length without substantially changing a cross-sectional dimension of the stent, the cross-sectional dimension spanning the lumen. In some embodiments, when in the expanded configuration, the stent length is reducible without substantially changing a radial cross-sectional dimension of the stent lumen.

Some embodiments describe a system, for implanting a stent in a patient's vessel, including an elongate body, having a proximal portion, a distal portion, and a body lumen extending from the proximal portion to the distal portion, the distal portion being configured to extend within a blood vessel of a patient; and a stent expandable from a compressed configuration to an expanded configuration, the stent having a proximal end, a distal end, a stent lumen extending from the proximal end to the distal end, and a stent wall that has, in the expanded configuration, an adjustable porosity; wherein the stent in the compressed configuration is configured to be slideably positioned within the body lumen and to change to an expanded configuration as the stent is advanced out of the body lumen; and wherein, when the distal end of the stent is in the expanded configuration, the adjustable porosity is adjustable by advancing or withdrawing the proximal end of the stent relative to the distal end of the stent.

In some embodiments, the adjustable porosity is adjustable in multiple discrete locations along a length of the stent wall. In some embodiments, when stent is in the expanded configuration, the adjustable porosity is decreasable in discrete, spatially separate sections of the stent wall as the proximal end of the stent is advanced toward the distal end of the stent. In some embodiments, when stent is in the expanded configuration, the adjustable porosity is increasable in the discrete, spatially separate sections of the stent wall as the proximal end is withdrawn from the distal end of the stent. In some embodiments, axially compressing the stent, when the stent is in the expanded configuration, decreases the porosity of at least a portion of the stent. In some embodiments, the stent automatically changes from the delivery configuration to the expanded configuration when unrestrained. In some embodiments, the stent is collapsible, after changing from the delivery configuration to the expanded configuration, by increasing a length of the stent. In some embodiments, the stent has a length extending from the proximal end to the distal end; and when in the expanded configuration, the stent length is reducible without substantially changing a radial cross-sectional dimension of the stent lumen.

Some embodiments relate to a stent, for implanting in a body lumen of a patient, including a proximal portion and a distal portion; a stent wall that defines a lumen extending from the proximal portion to the distal portion, the stent wall having a compressed configuration and an expanded configuration; wherein, when in the expanded configuration, the stent wall has a variable porosity that is adjustable by relative movement of the proximal portion with respect to the distal portion.

In some embodiments, the porosity of the stent wall is adjustable in a plurality of spatially separated locations between the proximal and distal portions. In some embodiments, the porosity of the stent wall is decreased when a length of the stent, extending from the proximal portion to the distal portion, is decreased. In some embodiments, when a length of the stent, extending from the proximal portion to the distal portion, is changed, a porosity of the stent wall in a first region, located between the proximal portion and the distal portion, changes relative to a porosity of the stent wall in a second region, located in at least one of the proximal portion and the distal portion. In some embodiments, when the length of the stent is decreased, the porosity in the first region is reduced relative to the porosity in the second region. In some embodiments, when the stent is in the expanded configuration, axially compressing the stent decreases the porosity of the stent. In some embodiments, the stent has a length extending from the proximal portion to the distal portion; and when in the expanded configuration, the stent length is substantially reducible without substantially changing a radial cross-sectional dimension of the stent lumen.

Some embodiments relate to a stent, for implanting in a patient, comprising a stent wall that has an adjustable porosity, such that a porosity of at least a portion of the stent wall can be adjusted while the stent is positioned in the patient.

Some embodiments disclose a stent, for implanting in a patient's vessel, including a stent wall configured to change between a compressed configuration and an expanded configuration, the stent wall having a proximal portion, a distal portion, and a middle portion extending between the proximal portion and the distal portion; wherein the middle portion of the stent has a variable porosity that is adjustable when the distal portion is in the expanded configuration.

In some embodiments, the porosity of the middle portion decreases when a length of the stent extending from the proximal portion to the distal portion decreases. In some embodiments, the porosity of the middle portion changes by changing a length of the middle portion. In some embodiments, when a length of the middle portion is decreased, the porosity of the middle portion is reduced relative to a porosity in at least one of the proximal portion and the distal portion. In some embodiments, when the stent is in the expanded configuration, axially compressing the stent decreases the porosity of the middle portion. In some embodiments, the stent has a length extending from the proximal portion to the distal portion; and when in the expanded configuration, the stent length is substantially reducible without substantially changing a radial cross-sectional dimension of the stent.

Some embodiments describe methods, of treating a patient's vessel, including: providing an elongate body, the elongate body comprising a proximal portion having a proximal end, a distal portion having a distal end, and a lumen extending between the proximal end and the distal end; providing a stent comprising a distal section and a proximal section and having a compressed configuration and an expanded configuration, the stent being configured to change from the compressed configuration to the expanded configuration; advancing the distal portion of the elongate body to a treatment site of the patient's vessel; moving the stent, in the compressed configuration, distally relative to the elongate body; changing the distal section of the stent from the compressed configuration to the expanded configuration in the patient's vessel, such that the distal section of the stent engages a wall of the vessel; treating the vessel such that material in the vessel becomes at least partially dislodged from the vessel wall; withdrawing the elongate body proximally relative to the stent, such that the proximal section of the stent changes from the compressed configuration to the expanded configuration; and trapping the material between the stent and the vessel wall.

Some embodiments further include changing the proximal section of the stent from the compressed configuration to the expanded configuration. In some embodiments, the treating the vessel comprises expanding a balloon within the vessel proximal to the distal section of the stent prior to changing the proximal section to the expanded configuration. In some embodiments, the treating the vessel comprises cutting material from the vessel wall proximal to the distal section of the stent prior to changing the proximal section to the expanded configuration. In some embodiments, the treating the vessel comprises inflating a balloon within the stent, thereby increasing a cross-sectional dimension of the expanded stent. In some embodiments, the material comprises at least one of plaque and thrombus.

Some embodiments describe methods, of treating a vessel during an intravascular procedure, including: expanding, on one side of a stenotic region of a vessel, a distal portion of a stent; expanding a proximal portion of the stent in the stenotic region; increasing a diameter of a lumen of the vessel in the stenotic region; and with the stent, trapping plaque debris, created during the procedure, between the stent and a wall of the vessel.

In some embodiments, the expanding the distal portion comprises advancing the distal portion relative to a delivery catheter and allowing the distal portion to automatically expand. Some embodiments further include engaging a wall of the vessel with the distal portion of the stent upon expansion of the distal portion. Some embodiments further include advancing the proximal portion with respect to the distal portion and decreasing a porosity of the distal portion with respect to another portion of the stent. In some embodiments, decreasing the porosity of the distal portion comprises changing the porosity to between about 30 percent and about 5 percent. In some embodiments, the increasing the diameter comprises expanding a balloon proximal to the expanded distal portion before expanding the proximal portion of the stent. In some embodiments, the increasing the diameter comprises expanding a balloon proximal to the expanded distal portion after expanding the proximal portion of the stent. Some embodiments further include cutting material from the vessel wall proximal to the distal portion of the stent before expanding the proximal portion. In some embodiments, cutting material from the vessel wall comprises rotating a cutting member about the stent.

Some embodiments describe methods, of treating a patient's vessel, including: advancing a stent to a stenotic region in the patient's vessel, the stent having a distal portion and a proximal portion; expanding, distal to the stenotic region, the distal portion of the stent; expanding, proximal to the stenotic region, the proximal portion of the stent; and with the stent, filtering debris between the stent and a wall of the vessel after expanding the distal portion and before expanding the proximal portion.

Some embodiments further include trapping the debris between the stent and the vessel wall. Some embodiments further include aspirating the debris to remove the debris from the patient. Some embodiments further include increasing a diameter of a lumen of the vessel in the stenotic region by expanding a balloon within the vessel. Some embodiments further include increasing a diameter of a lumen of the vessel in the stenotic region by expanding a balloon within the stent. In some embodiments, the expanding the distal portion comprises advancing the distal portion relative to a delivery catheter and allowing the distal portion to expand automatically. In some embodiments, the expanding the distal portion comprises engaging a wall of the vessel with the distal portion of the stent. Some embodiments further include advancing the proximal portion with respect to the distal portion and decreasing a porosity of the distal portion with respect to another portion of the stent. In some embodiments, decreasing the porosity of the distal portion comprises changing the porosity to between about 30 percent and about 5 percent. Some embodiments further include cutting material from the vessel wall proximal to the distal portion of the stent prior to expanding the proximal portion. In some embodiments, the cutting comprises rotating a cutting member about the stent prior to expanding the proximal portion.

Some embodiments relate to a system, for treating a patient's vessel, including: an elongate body having a proximal portion with a proximal end, a distal portion with a distal end, and a lumen extending between the proximal end and the distal end; a stent, configured to reside within the elongate body and to be advanced relative to the elongate body, the stent having a distal section and a proximal section, the stent being configured to change between a compressed stent configuration and an expanded stent configuration; and a treatment device that increases a cross-sectional dimension of a lumen of the vessel in a stenotic region of the vessel, by cutting plaque material in the stenotic region or by expanding the stenotic region; wherein the distal section of the stent is configured to engage a wall of the vessel and to change from a compressed distal configuration to an expanded distal configuration when advanced distal to the distal end of the elongate body; wherein the proximal section of the stent is configured to engage a wall of the vessel and to change from a compressed proximal configuration to an expanded proximal configuration by advancing the stent relative to the elongate body; wherein, when the expanded distal section of the stent engages the vessel wall, the distal section captures debris dislodged from the stenotic region by the treatment device.

In some embodiments, the stent, when unrestrained in the expanded stent configuration, has a porosity between about 60% and about 85%. In some embodiments, the stent, when unrestrained in the expanded stent configuration, has a porosity between about 65% and about 75%. In some embodiments, the stent is axially compressible when in the expanded stent configuration, and the porosity is reducible to between about 5% and about 30% without substantially changing an outer diameter of the stent. In some embodiments, the stent, in the expanded stent configuration, is adjustable to decrease porosities of the stent in a respective plurality of locations between the proximal section and the distal section. In some embodiments, the stent, in the expanded stent configuration, is changeable in a plurality of locations along the stent to have a porosity in at least one of the locations of from about 5% and about 30%. In some embodiments, the elongate body comprises an expandable member that expands when the distal section of the stent is in the expanded distal configuration and when the proximal section of the stent is in the compressed proximal configuration. In some embodiments, the treatment device comprises a cutting member that cuts the plaque material. In some embodiments, the cutting member rotates about the compressed proximal section of the stent when the distal section is expanded and engages the vessel wall. In some embodiments, the cutting member rotates about the elongate body.

Some embodiments describe a device, for filtering blood of a patient during an intravascular procedure, comprising: a stent having a distal section and a proximal section, the stent being configured to change between a compressed stent configuration and an expanded stent configuration; and a treatment device that increases a cross-sectional dimension of a lumen of the vessel in a stenotic region of the vessel by cutting plaque material in the stenotic region or by expanding the stenotic region; wherein the distal section of the stent is configured to engage a wall of the vessel and to change from a compressed distal configuration to an expanded distal configuration; wherein, when the expanded distal section of the stent engages the vessel wall, the distal section captures debris dislodged from the stenotic region by the treatment device.

In some embodiments, the proximal section of the stent is configured to engage the vessel wall and to change from a compressed proximal configuration to an expanded proximal configuration. In some embodiments, the elongate body comprises an expandable member that expands when the distal section of the stent is in the expanded distal configuration and when the proximal section of the stent is in the compressed proximal configuration. In some embodiments, the expanded distal section operates as a filter to restrict migration of debris with the blood downstream past the expanded distal section. In some embodiments, the treatment device comprises a cutting member that cuts the plaque material. In some embodiments, the cutting member rotates about the compressed proximal section of the stent. In some embodiments, the stent, when unrestrained in the expanded configuration, has a porosity between about 60% and about 85%. In some embodiments, the stent, when unrestrained in the expanded configuration, has a porosity between about 65% and about 75%. In some embodiments, the stent is axially compressible when in the expanded stent configuration, and the porosity is reducible to between about 5% and about 30% without substantially changing an outer diameter of the stent. In some embodiments, the porosity is reducible to between about 3%, about 10%, about 20%, about 25%, about 35%, about 40%, about 45%, about 50%, and about 55%. In some embodiments, the stent, in the expanded stent configuration, is adjustable to decrease porosities of the stent in a respective plurality of locations between the proximal section and the distal section. In some embodiments, the stent, in the expanded stent configuration, is changeable in a plurality of locations along the stent to have a porosity in at least one of the locations of from about 5% and about 30%.

In some embodiments, the stent can be used in other lumens of the body. For example, in some embodiments, the stent can be used in the ureter, the urethra, and the fallopian tube of a patient's body.

Some embodiments describe methods, of treating an aneurysm in the vessel of a patient, including: expanding, in a vessel having an aneurysm, a first stent having a first stent proximal end and a first stent distal end, such that the first stent extends from a first location, proximal to the aneurysm, to a second location, distal to the aneurysm; expanding, within the first stent, a second stent having a second stent proximal end and a second stent distal end, such that when the second stent is expanded and engages the first stent, the second stent is axially positioned substantially adjacent to the aneurysm, the second stent proximal end is positioned distal to the first stent proximal end, and the second stent distal end is positioned proximal to the first stent distal end, thereby impeding blood flow from the vessel into the aneurysm.

In some embodiments, blood flow through the first and second stents into the aneurysm is less than blood flow into the aneurysm would be through the first stent alone. In some embodiments, the second proximal end is substantially coterminous with the first proximal end. In some embodiments, the first stent and the second stent have, when unrestrained, substantially the same porosity. Some embodiments further include adjusting a porosity of at least one of the first and second stents along a portion of the respective stent. In some embodiments, the adjusting comprises decreasing the porosity. In some embodiments, the porosity is decreased by axially compressing at least one of the first and second stents.

Some embodiments relate to methods, of treating an aneurysm in a vessel of a patient, including: expanding within the vessel a first stent such that the first stent extends from a first location distal to an aneurysm of the vessel to a second location proximal to the aneurysm; and expanding a second stent, within the first stent, such that the second stent is positioned substantially adjacent to the aneurysm.

In some embodiments, the first stent and the second stent have, when unrestrained, substantially the same porosity. Some embodiments further include adjusting a porosity of at least one of the first and second stents along a portion of the respective stent. In some embodiments, the adjusting the porosity comprises decreasing the porosity. In some embodiments, the porosity is decreased by axially compressing at least one of the first and second stents. In some embodiments, blood flow through the first and second stents into the aneurysm is less than blood flow into the aneurysm would be through the first stent alone.

Some embodiment relate to a braided stent, for implanting in a patient's vessel, including: a plurality of braided strands, having an average strand thickness, the plurality of braided strands forming pores in open areas between strands; wherein the stent is expandable from a compressed configuration to an expanded configuration; wherein the pores have an average pore length; wherein the stent has a porosity equal to a ratio of an open surface area of the stent to a total surface area of the stent; wherein, when the stent is in the expanded configuration, the porosity of the stent multiplied by the average pore length is equal to or less than about 0.3 mm.

In some embodiments, each of the braided members comprises a ribbon having a width greater than its thickness. In some embodiments, each of the braided members comprises a ribbon having a width that is substantially equal to its thickness. In some embodiments, the porosity of a portion of the stent can be reduced by axially compressing the portion of the stent. In some embodiments, the axially compressed portion of the stent axially expands when unrestrained. In some embodiments, the porosity of a portion of the stent can be reduced to between about 5 percent and about 50 percent. In some embodiments, when the stent is in the expanded configuration, the porosity of the stent multiplied by the average pore length multiplied by the average strand thickness is equal to or less than about 0.023 $mm^2$.

Some embodiments relate to a braided stent, for implanting in a patient's vessel, including: a plurality of braided strands, having an average strand thickness, the plurality of braided strands forming pores in open areas between strands; wherein the stent is expandable from a compressed configuration to an expanded configuration; wherein the pores have an average pore length; wherein the stent has a porosity equal to a ratio of an open surface area of the stent to a total surface area of the stent; wherein, when the stent is in the expanded configuration, the porosity of the stent multiplied by the average strand thickness is equal to or less than about 0.002 inches.

In some embodiments, the average strand thickness is less than about 0.004 inches. In some embodiments, the average strand thickness is equal to or less than about 0.003 inches. In some embodiments, the average strand thickness is equal to or less than about 0.002 inches. In some embodiments, the average strand thickness is equal to or less than about 0.001 inches. In some embodiments, when the stent is in the expanded configuration, the average strand thickness multiplied by the average pore length is equal to or less than about 0.0328 $mm^2$. In some embodiments, the pores have an average pore area defined by an inner edge of bordering strands, the average pore area ranging from about $2.2 \times 10^{-5}$ $in^2$ to about $12.3 \times 10^{-5}$ $in^2$. In some embodiments, when the stent is in the expanded configuration, the average strand thickness multiplied by the average pore area is between about $2.2 \times 10^{-9}$ $in^3$ and about $3.69 \times 10^{-7}$ $in^3$.

Some embodiments relate to a braided stent, for implanting in a patient's vessel, including: a plurality of braided strands, having an average strand thickness, the plurality of braided strands forming pores in open areas between strands; wherein the stent is expandable from a compressed configuration to an expanded configuration; wherein the pores have an average pore length; wherein the stent has a porosity equal to a ratio of an open surface area of the stent to a total surface area of the stent; wherein, when the stent is in the expanded configuration, the average pore length multiplied by the average strand thickness is equal to or less than about $9.4 \times 10^{-5}$ $in^2$ In some embodiments, the average pore length multiplied by the average strand thickness is equal to or less than about $6.8 \times 10^{-5}$ $in^2$. In some embodiments, the average pore length multiplied by the average strand thickness is equal to or less than about $5 \times 10^{-5}$ $in^2$.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

FIGS. 2A and 2B illustrate embodiments of an occluding device to treat aneurysms.

FIG. 5 shows the occluding device in a compressed state inside a catheter being advanced out of the catheter using a plunger.

FIG. 6 shows the compressed occluding device shown in FIG. 5 deployed outside the catheter and is in an expanded state.

FIGS. 11A, 11B, 11C, 11D, 11E, 11F and 11G show the non-uniform density of the braid that provides the desired occluding device.

FIG. 37 illustrates embodiments of the occluding device in treating an aneurysm.

FIG. 38 illustrates an example of an occluding device deployed within another occluding device.

FIG. 39 illustrates an example of two occluding devices with an overlapping portion.

FIG. 40 illustrates a cross sectional view of an example of an occluding device deployed within another occluding device.

FIG. 54 illustrates an example of an expanded occluding device that expands responsive to pressure.

FIG. 55 illustrates the occluding device of FIG. 54 after a negative pressure is applied to the occluding device.

FIG. 60 illustrates an example of an expanded occluding device.

FIG. 61 illustrates the example of FIG. 60 after the occluding device is repositioned within a blood vessel.

FIG. 65 illustrates an example of the catheter positioned at a treatment site in a blood vessel.

FIG. 66 illustrates an example of the stent partially deployed in the blood vessel;

FIG. 70 is a cutaway view of the catheter carrying the guidewire assembly loaded with the stent according to another embodiment of the disclosure.

FIG. 71 is a perspective view of the catheter with a cutting tool according to an embodiment of the disclosure.

FIG. 75 illustrates an example in which the catheter and the cutting tool are advanced separately in a blood vessel.

FIG. 76 illustrates an example of the catheter and the cutting tool disposed on another catheter in a blood vessel.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

Flexible Vascular Occluding Device

Figure 1:
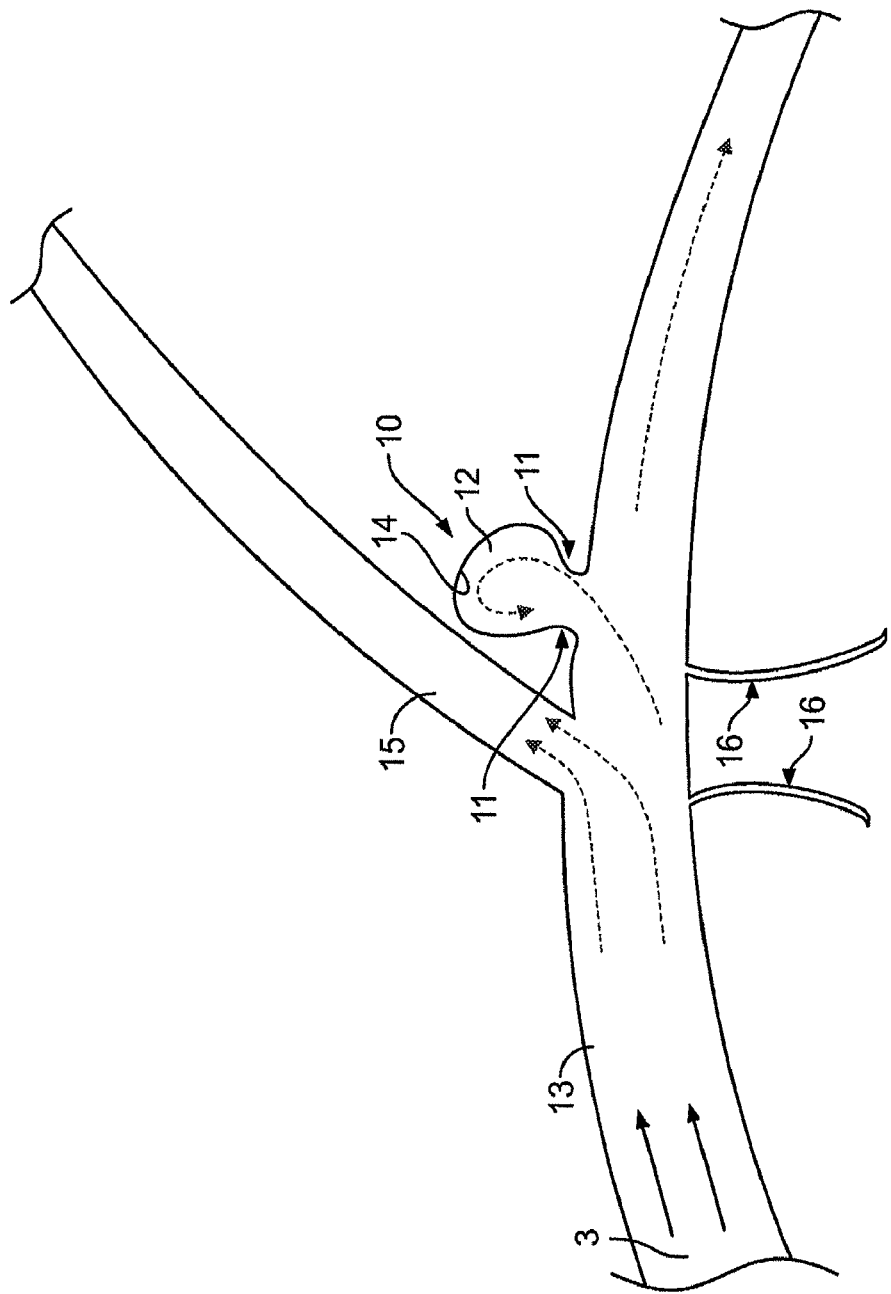
FIG. 1 is an illustration of an aneurysm, branch vessels and blood flow to the aneurysm.

FIG. 1 illustrates a typical cerebral aneurysm 10. A neck 11 of the aneurysm 10 can typically define an opening of between about 2 to 25 mm. As is understood, the neck 11 connects the vessel 13 to the lumen 12 of the aneurysm 10. As can be seen in FIG. 1, the blood flow 3 within the vessel 13 is channeled through the lumen 12 and into the aneurysm. In response to the constant blood flow into the aneurysm, the wall 14 of lumen 12 continues to distend and presents a significant risk of rupturing. When the blood within the aneurysm 10 causes pressure against the wall 14 that exceeds the wall strength, the aneurysm ruptures. An aspect of the subject technology may prevent or reduce likelihood of such ruptures. Also shown in FIG. 1 are the bifurcation 15 and the side branches 16.

FIG. 2 illustrates one embodiment of a vascular occluding device 200 in accordance with an aspect of the disclosure. In the illustrated embodiment, the occluding device 200 has a substantially tubular structure 22 defined by an outer surface 21, an inner surface 24 and a thin wall that extends between the surfaces 21, 24. A plurality of openings 23 extend between the surfaces 21, 24 and allow for fluid flow from the interior of the occluding device 200 to the wall of the vessel. Occluding device 200 is radially compressible and longitudinally adjustable.

Figure 3:
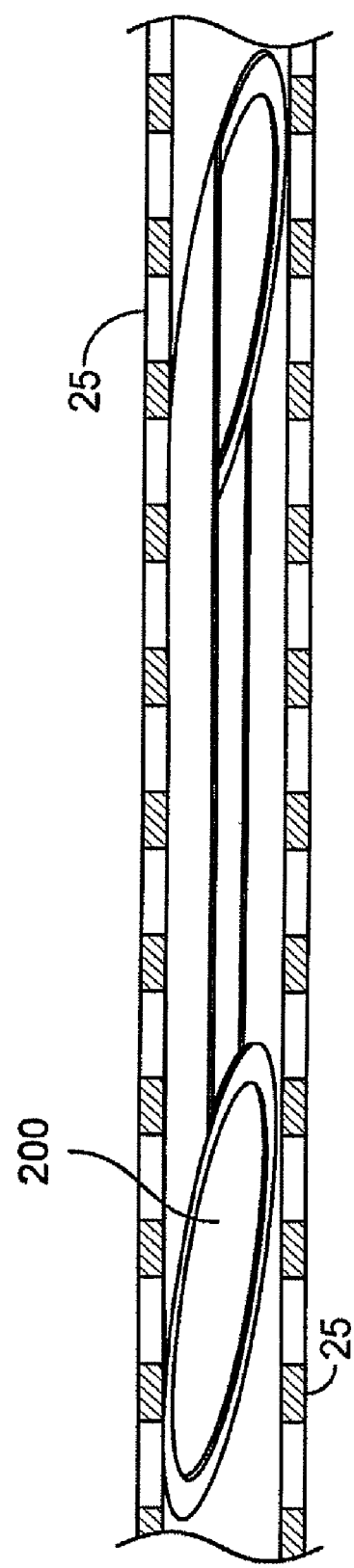
FIG. 3 is an illustration of embodiments shown in FIGS. 2A and 2B in a compressed state inside a catheter.

FIG. 3 shows a catheter 25 and the occluding device 200 inside the catheter 25 in a compressed state prior to being released within the vasculature of the patient.

Figure 4A:
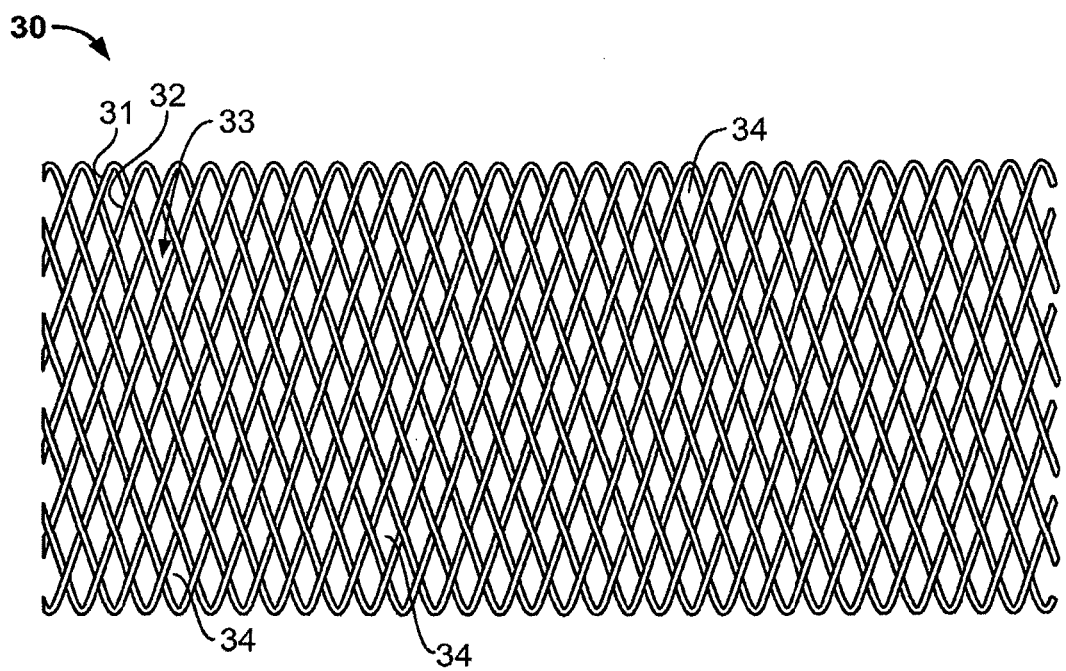
FIG. 4A depicts embodiments of an occluding device for treating aneurysms.
Figure 4B:
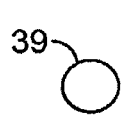
FIGS. 4B and 4C illustrate cross sections of portions of ribbons that can be used to form the occluding device of FIG. 4A.

FIG. 4 illustrates another embodiment of the occluding device 30 having two or more strands of material(s) 31, 32 wound in a helical fashion. The braiding of such material in this fashion results in a lattice structure 33. As can be understood, the dimension of the lattice 33 and the formed interstices 34 is determined, at least in part, by the thickness of the strand materials, the number of strands and the number of helices per unit length of the occluding device 30. For example, the interstices 34 and/or the dimension of the lattice 33 may be determined by the number of strands of material(s) 31, 32 wound in helical fashion. In some embodiments, any number of braiding ribbons up to 16 braiding ribbons may be used (e.g., 5, 8, 10, 13, 15 or 16 braiding ribbons). In some embodiments, 16-32 braiding ribbons may be used (e.g., 20, 23, 25, 27, 30, or 32 braiding ribbons). In some embodiments greater than 32 braiding ribbons may be used such as, for example, 35, 40, 48, 50, 55, 60, 80, 100, or greater braiding ribbons. In some embodiments, 48 braiding ribbons are used.

Hence, strands of material, such as ribbons, may intersect to form a braid pattern. The intersection of the strand material may be formed in either a radial or axial direction on a surface of a forming device such as a braiding mandrel. When the intersection of the strand material is along an axial path, for example, the intersecting material may be at a fixed or variable frequency. As one example of strand material intersecting at a fixed frequency, the intersecting strand material may be along any 1.0 inch axial path on the surface of the forming device (e.g., a braiding mandrel) to indicate the pick count. When the intersection of the strand material is along a radial path or circumferential path, the spacing of the strand material may be uniformly or variably distributed. In one example of the strand material along a radial or circumferential path in which the spacing is uniformly distributed, the spacing along the radial direction may be determined based on the following formula:

$$(\pi)*(\text{forming device diameter})/(\text{\#ribbons}/2) \quad \text{Eq. (1)}$$

Figure 17:
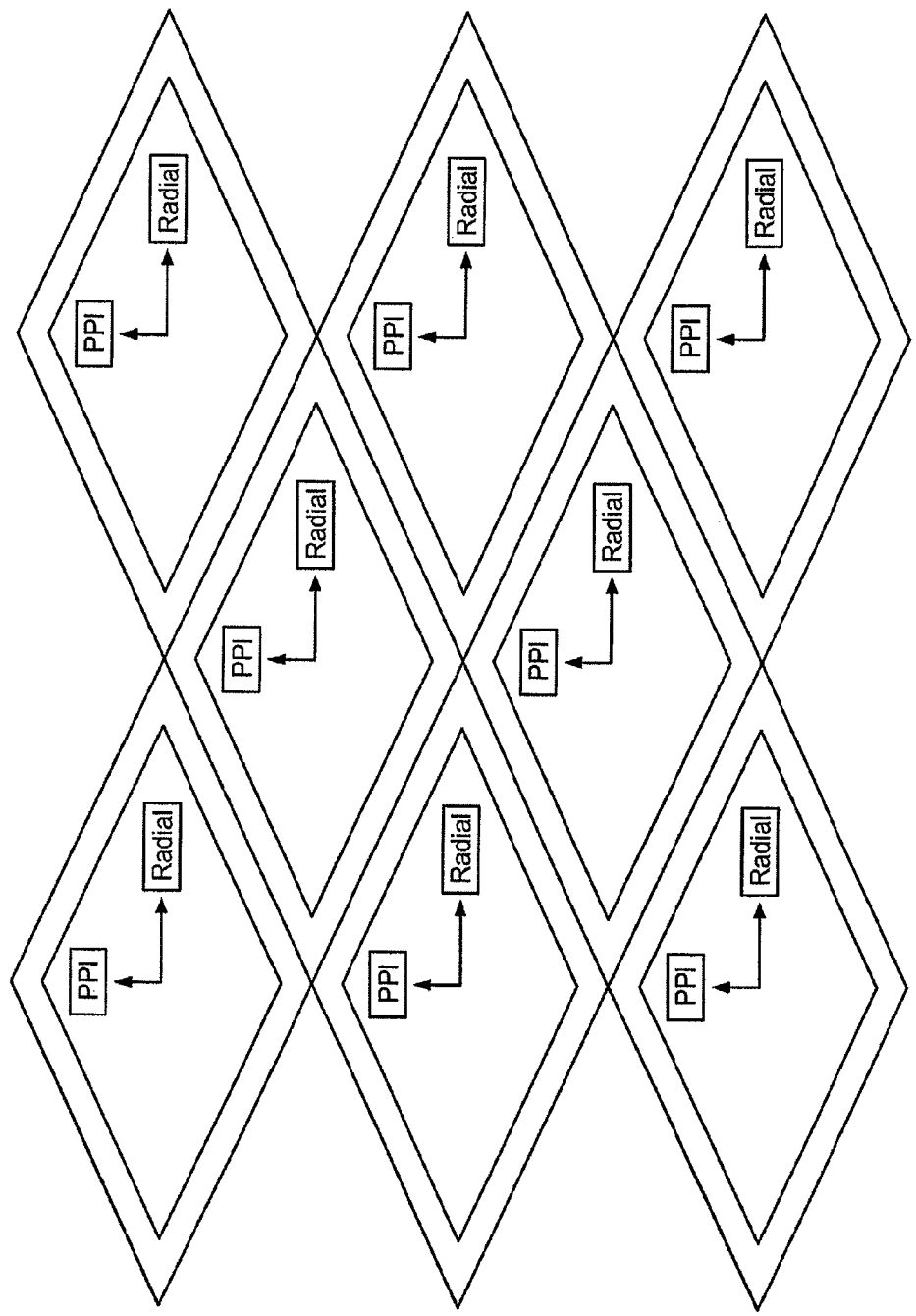
FIG. 17 illustrates embodiments of braiding elements of a lattice in an occluding device.
Figure 18:
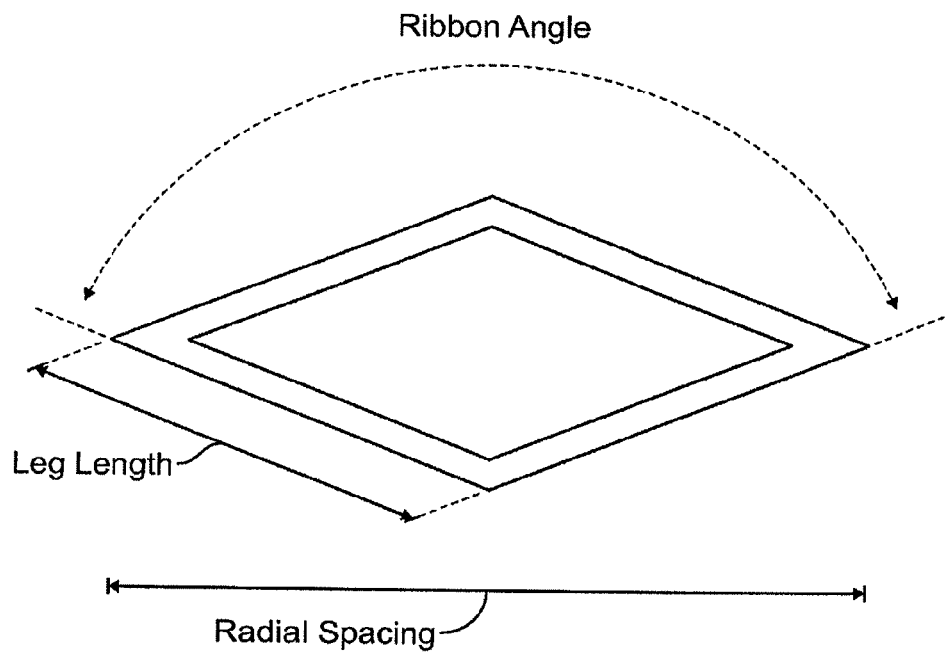
FIG. 18 illustrates an example of a braiding element of a lattice in an occluding device.

FIG. 18 illustrates an example of braiding elements or cells in the radial and PPI (picks per inch) directions. Any single element of the braid (i.e., braid element) may be combined to form a mesh pattern as illustrated in FIG. 17 on a surface of a forming device (e.g., braiding mandrel). The braid is capable of impeding or disrupting the some types of fluid flow (e.g., blood) in a lumen of a patient (e.g., blood vessel). The braid or lattice pattern, density, shape, etc. when the occluding device is deployed in the vessel, may at least partially determine the flow within the vessel. Each of the parameters of the braid or lattice may also be controlled by a user to control flow.

Parameters for determining the flow through an occluding device containing a lattice pattern, density, shape, etc. include surface coverage of the occluding device and cell size of the braid or lattice pattern. Each of these parameters may further characterize the geometry of the braid or lattice. Surface coverage may be determined as (surface area)/(total surface area), where the surface area is the surface area of the frame or solid element and the total surface area is of the entire element (i.e., frame and opening).

Cell size may be determined as the greater length defining a cell opening. Braiding patterns that increase surface coverage while decreasing cell size may have an increased effect on disrupting or impeding the flow through the braid or lattice. Each of the parameters of surface coverage and cell size may further be enhanced by varying the width of the strand material (e.g., the ribbons), increasing the number of strands of strand material defining the braid, and/or increasing the PPI.

The braiding or lattice pattern as described may be further defined by various parameters including, for example, the number of strands (e.g., ribbons), the width of each ribbon/strand, the braiding PPI, and/or the diameter of the forming device (e.g., mandrel diameter), to name a few. In some embodiments, the diameter of each strand is between about 0.001 inches and 0.0014 inches. In some embodiments, the diameter of each strand is between about 0.0005 inches and 0.0020 inches. In some embodiments, the diameter of each strand is less than or equal to about 0.0005 inches or greater than about 0.0020 inches.

Based on the lattice parameters, a leg length and a ribbon angle may be determined. The leg length may define the length of an aspect of the braiding element. For example, if the braiding element is diamond shaped as illustrated in FIG. 17, the length of one side of the diamond shaped braiding element is the "leg length." A ribbon angle may define the angle created by two intersecting aspects of the braiding element. In the example illustrated in FIG. 17, the ribbon angle is the angle formed between two adjacent sides of the diamond shaped braiding element. Radial spacing of braid elements in a lattice pattern can define the width of a braiding element in radial direction. FIG. 18 illustrates an example of a radial spacing, leg length and ribbon angle of a braid element.

Radial spacing of the lattice may be determined as set forth in Equation 1 as follows:

$$\text{Radial Spacing}=(\pi)*(\text{forming device diameter})/(\text{\#ribbons}/2) \quad \text{Eq. (1)}$$

The braiding element may be fitted into a vessel based on the radial spacing or the diameter of the vessel. The radial spacing of the lattice may be adjusted based on the diameter of the vessel. For example, if the diameter of the vessel is small, the radial spacing may be adjusted to a smaller dimension while the leg length of the braid elements may be maintained. Also in this example, the ribbon angle may also be adjusted to achieve the adjusted radial spacing. Adjusting the ribbon angle may also alter the spacing of the braid element in the PPI direction.

Figure 19:
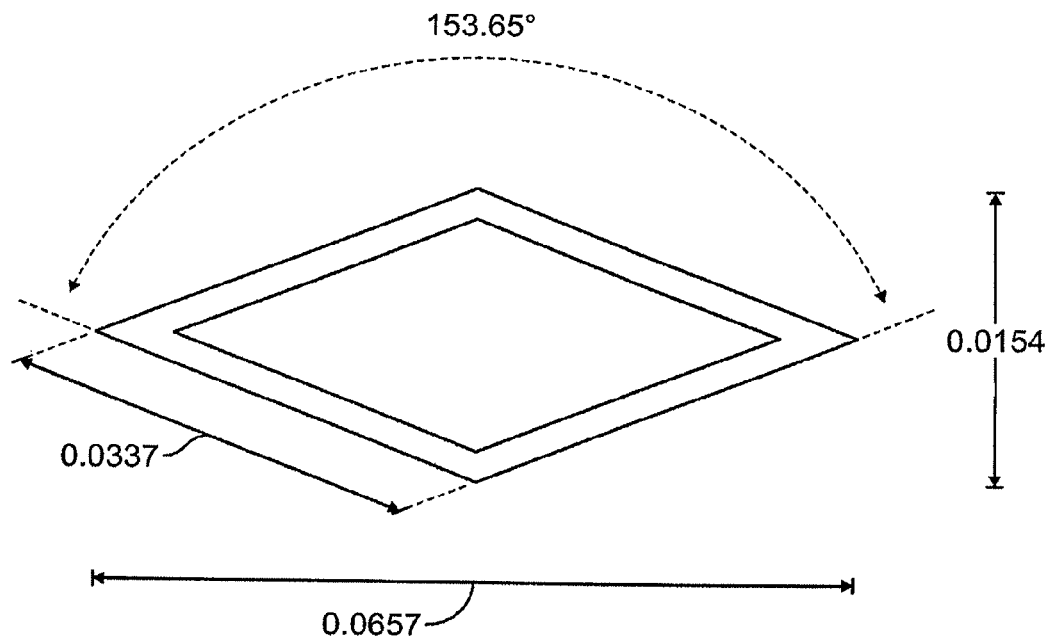
FIG. 19 illustrates an example of another braiding element of a lattice in an occluding device.

FIG. 19 illustrates an example of determining a radial spacing and ribbon angle of a lattice structure in an occluding device. In this example, a lattice or braid contains sixteen interlacing ribbons, with each ribbon being about 0.004 inches wide and braided on a forming device such as a mandrel with a diameter of about 4.25 mm and 65 PPI. Thus, in this example, the number of braiding elements is sixteen, the ribbon width is about 0.004 inches, the spacing in the PPI direction is about ⅟₆₅=0.01538 inches and the diameter of the forming device (e.g., mandrel diameter) is about 4.25 mm.

Figure 20:
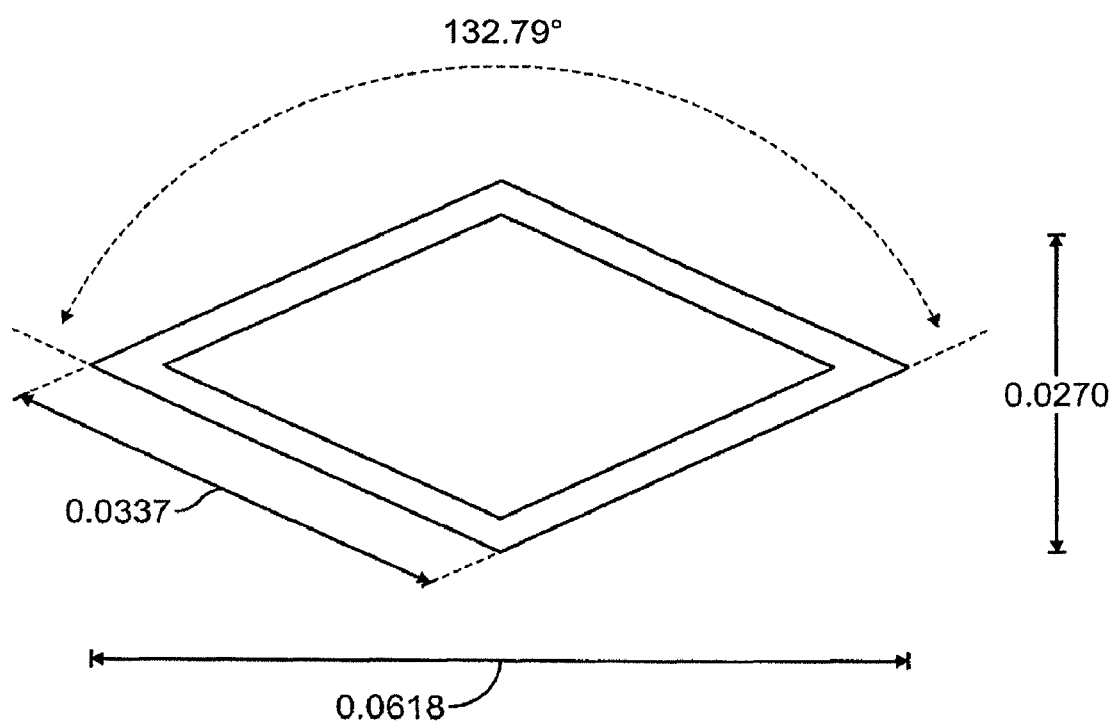
FIG. 20 illustrates a braiding element of an occluding device fitted into a vessel diameter.

FIG. 20 illustrates the example of FIG. 19 after the braiding element is fitted into an appropriate vessel diameter. In this example, the radial spacing is adjusted to a smaller length to accommodate a smaller vessel diameter. The leg length remains constant at about 0.0337 inches so the ribbon angle changes based on changes in the radial spacing. In this example, the radial spacing is adjusted to about 0.06184 inches and the ribbon angle is adjusted to about 132.79 degrees. Also, the spacing of the braid element in the PPI direction is also changed. In this example, the spacing of the braid element in the PPI direction increases from about 0.0154 inches to about 0.0270 inches.

Table 1 illustrates additional examples of lattice or braid patterns of varying PPI, ribbon width (RW), or number of ribbons. In addition, each of the braid patterns in Table 1 may produce patterns with the same percent coverage within a vessel.

TABLE 1

| # ribbons | 16 | 32 | 48 | 64 |
|---|---|---|---|---|
| Braid diameter (mm) | 4.25 | 4.25 | 4.25 | 4.25 |
| Braid diameter (in) | 0.16732 | 0.16732 | 0.16732 | 0.16732 |
| PPI | 65.00 | 130.00 | 275.00 | 260.00 |
| RW (mils) | 4.0000 | 2.0000 | 1.3000 | 1.0000 |
| Node Spacing (ppi) | 0.01538 | 0.00769 | 0.00364 | 0.00385 |
| Node Spacing (radial) | 0.06571 | 0.03285 | 0.02190 | 0.01643 |
| Ribbon Angle (ppi) | 153.65 | 153.65 | 161.13000 | 153.62 |
| Leg Length (in) | 0.03374 | 0.01687 | 0.0111 | 0.00844 |
| Vessel diameter (mm) | 4 | 4 | 4 | 4 |
| In-vessel device Node spacing | 0.06184 | 0.03092 | 0.02061 | 0.01546 |
| In-vessel device Ribbon Angle (ppi) | 132.79 | 132.79 | 136.37 | 132.70 |
| In-vessel device Node spacing (ppi) | 0.02702 | 0.01351 | 0.00825 | 0.00677 |
| In-vessel device PPI | 37.01 | 74.04 | 121.21 | 147.72 |
| In-vessel device braided closed area (in2) | 0.00024814 | 0.00006203 | 0.00002641 | 0.00001551 |
| In-vessel device Braided Open Area (in2) | 0.00058741 | 0.00014680 | 0.00005861 | 0.00003681 |
| In-vessel device coverage | 29.7% | 29.7% | 31.06% | 29.64% |
| In-vessel device total area (in2) | 0.00083555 | 0.00020883 | 0.00008502 | 0.00005232 |
| In-vessel device cell size (mm) | 1.317 | 0.658 | 0.430 | 0.329 |

Hence, the radial spacing may be calculated as: Radial spacing=$(\pi)$*(forming device diameter)/(# ribbons/2)=(3.14)*(0.425/2.54)/(16/2)=0.0657 inches. FIG. 19 illustrates an example of a braiding element with a radial spacing of about 0.0657 inches. In addition, the leg length of the example is about 0.0337 inches, the ribbon angle is about 153.65 degrees, and the spacing of the braiding element in the PPI direction, based on the ribbon angle and leg length is about 0.0154 inches.

In some embodiments, the braiding pattern can include a "1 over 1 under 1" pattern. In some embodiments, the braiding pattern can include a "1 over 2 under 2" pattern. In some embodiments, the braiding pattern can include other variations of braids.

The occluding device may be placed into a protective coil to enhance placement of the occluding device in a vessel. Also, the occluding device may be housed in a delivery device, such as a catheter, for placement within a vessel. The occluding device may be created at a size or dimension based on the size of the protective coil, delivery device, or catheter housing the occluding device. For example, the number of strands or ribbons in the lattice structure of the occluding device that fit into a corresponding protective coil, delivery device, or catheter may be determined such that the occluding device is effectively stored or housed prior to deployment in a vessel. In one example, the strands of the occluding device may overlap in a 2-layer structure including an inner layer and an outer layer, the outer layer contacting the protective coil.

In some embodiments, the braiding diameter is 0.25 mm larger than the recommended vessel size. In some embodiments, the percent coverage by the stent of the vessel wall is about ⅓, or 33% of the total surface area when the stent is placed within the vessel. In some embodiments, the braiding PPI (picks per inch, or the number of wire crossings per inch) is 275 PPI. In some embodiments, the braid is manufactured over a metal core or mandrel, and the braiding is not too dense to hinder removal of the braiding from the metal core or mandrel. In some embodiments, the PPI of the stent, when implanted within the vessel, is about 100 PPI. In some embodiments, the diameter of the strands of the stent ranges from about 0.001 inch to about 0.0014 inch. In some embodiments, the number of strands selected for a stent is based on the desired diameter of the stent. For example, in some embodiments, 48 strands are used for a stent diameter ranging from about 2.75 mm to about 4.25 mm, 64 strands are used for a stent diameter ranging from about 4.5 mm to about 6.0 mm, 72 strands are used for a stent diameter ranging from 6.0 mm and greater, and 32 strands are used for a stent diameter ranging from 2.5 mm and smaller. In some embodiments, the number of strands is selected based on a diameter of the delivery catheter.

In one example, a housing such as a protective coil, delivery device or catheter that houses the occluding device may have a constant size or diameter and the characteristics of the occluding device may be determined to fit the housing. For example, a ribbon size or width may be determined based on the desired size of the housing. In this way, the size (or diameter) of the housing (e.g., protective coil, delivery device or catheter) may be constant for a variety of occluding devices that may vary in size or number of ribbons.

Figure 21:
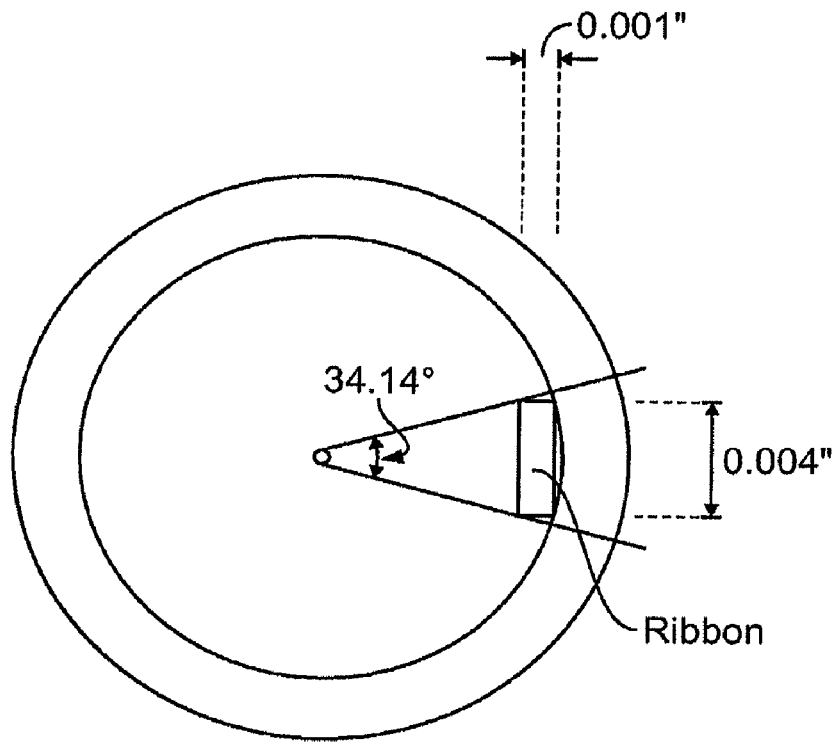
FIG. 21 is a cross sectional view of an example of a protective coil.

FIG. 21 illustrates an example of a cross sectional view of a protective coil. In this example, a number of strands or ribbons in a lattice structure of an occluding device is determined for a protective coil. The protective coil illustrated in FIG. 21 has a circular cross sectional area with a diameter. A strand or ribbon of a predetermined thickness or size is placed within the protective coil such that the outer surface of the strand/ribbon contact the inner surface of the protective coil. The inner surface of the strand/ribbon creates a concave surface within the protective coil. A second strand/ribbon is placed within the protective coil such that the outer surface of the second strand/ribbon contacts an inner circumference in contact with the concave surface of the strand/ribbon previously placed in the protective coil. The angle from a center point of the circular protective coil from one edge of the second strand/ribbon to an opposite edge of the second strand/ribbon is determined (i.e., the "arc-angle"). Based on these measurements, the number of strands or ribbons of the predetermined size or thickness may be determined as follows: (Arc-angle)*(# ribbons/2)<=360 degrees (i.e., # ribbons<=720 degrees/angle).

In the example illustrated in FIG. 21, an occluding device is constructed using approximately a 0.001 inch by 0.004 inch ribbon. The arc-angle of the ribbon element at the center of the protective coil between a first line drawn from the center point of the protective coil to one edge of an inner layer ribbon and a second line drawn from the center point of the protective coil to the opposite edge of the inner layer ribbon is about 34.14 degrees. Thus, the calculated number of ribbons is less than or equal to about 720 degrees/34.14 degrees=20 ribbons.

Table 2 illustrates additional examples of different designs for loading a lattice structure of an occluding device in a protective coil.

TABLE 2

| # ribbons | 16 | 32 | 64 |
|---|---|---|---|
| Protective Coil ID (in) | 0.017 | 0.017 | 0.017 |
| Ribbon Width (in) | 0.004 | 0.002 | 0.001 |
| Ribbon Thickness (in) | 0.001 | 0.001 | 0.001 |
| Inner Circle Angle | 36.98 | 17.83 | 8.84 |
| Max # Ribbons fitting in inner circle | 9.73 | 20.19 | 40.72 |
| # ribbons in inner circle | 8 | 16 | 32 |

Figure 22:
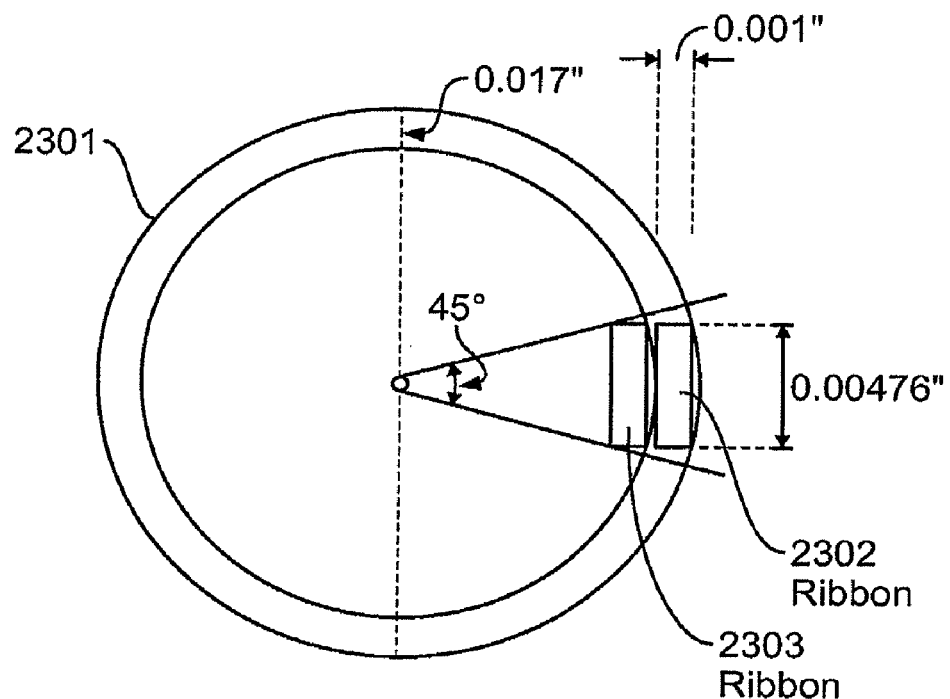
FIG. 22 illustrates an example of determining ribbon dimensions of an occluding device in a protective coil or a delivery device.

FIG. 22 illustrates another example of determining ribbon dimensions for an occluding device in a protective coil or a delivery device. In this example, an occluding device with a lattice or braid structure based on a thickness of a ribbon. As FIG. 22 illustrates, the diameter of the protective coil or delivery device 2301 is about 0.0170 inches. A first ribbon 2302 is fitted within the outer surface of the protective coil or delivery device 2301. A second ribbon 2303 is placed in contact with an inner circumference of the protective coil or delivery device 2301 where the inner circumference is a circumference that is tangential to the inner surface of the first ribbon 2302. The second ribbon 2303 is placed within the inner circumference such that lateral ends of the second ribbon 2303 are in contact with the inner circumference of the protective coil or delivery device 2301. The arc-angle between a first line extending from the center point of the protective coil or delivery device 2301 to one lateral end of the second ribbon 2303 and a second line extending from the center point of the protective coil or delivery device 2301 to the other lateral end of the second ribbon 2303 is calculated as illustrated in FIG. 22.

In this example, the maximum dimensions of the first and second ribbons 2302, 2303 are determined based on the calculated arc-angle formed. For example, to allow eight ribbons in the inner circumference of the protective coil or delivery device 2301, the arc-angle may be calculated as (360 degrees)/8=45 degrees as FIG. 22 illustrates. Based on a 45 degree angle, the maximum ribbon width may be determined as about 0.00476 inches to allow eight ribbons of a thickness of about 0.001 inches to fit within the inner circumference of the protective coil or delivery device 2301. As used herein, the term "maximum" is a broad term, and is intended to mean, without limitation, a desired upper range of a particular parameter, and the term "minimum" is a broad term, and is intended to mean, without limitation, a desired lower range of a particular parameter. In some embodiments, the parameters explained herein, described as maximum, can extend greater than or beyond the maximum range, and parameters explained herein, described as minimum, can extend less than or beyond the minimum range.

Figure 23:
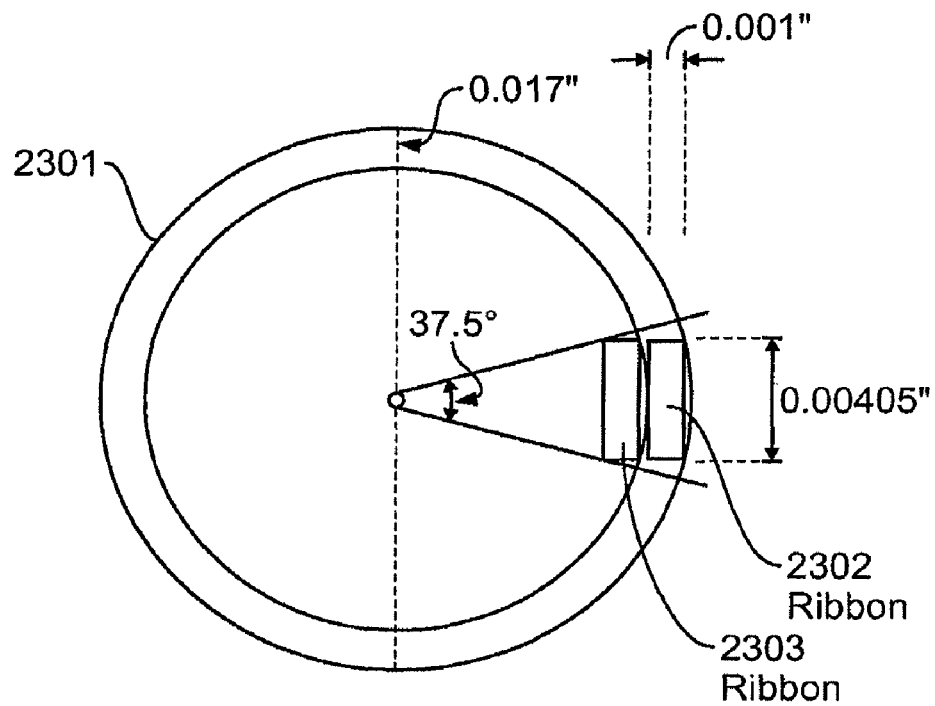
FIG. 23 illustrates another example of determining ribbon dimensions of an occluding device in a protective coil or a delivery device.

In another example, a narrower ribbon width is used to compensate for material tolerance variations and curvature. Based on extensive research and experimentation by the applicants, it was discovered that a tolerance range applied to the ribbon widths of about 20% can compensate for such material tolerance variations. FIG. 23 illustrates an example of a 20% tolerance range or cushion applied to ribbon widths of an occluding device.

In this example, 20% additional ribbons are desired in the occluding device (i.e., ribbons). The maximum width of the ribbons may be determined based on the desired number of 9.6 ribbons by calculating the angle as described above. Specifically, the arc-angle may be calculated as (360 degrees)/9.6=37.7 degrees. Based on this calculation, the maximum width of the ribbons may be determined as about 0.00405 inches as illustrated in FIG. 23. Thus, in this example, a 20% cushion is applied to permit about 9.6 ribbons in the protective coil or delivery device at a maximum width of about 0.00405 inches.

Table 3 provides additional examples of ribbon widths for various ribbon thicknesses. In the examples provided in Table 3, the ribbon thicknesses range from about 0.0007 inches to about 0.0015 inches.

TABLE 3

| Ribbon Thickness (in) | Calculated max width (in) | 20% cushion width (in) |
| --- | --- | --- |
| 0.0005 | 0.00543 | 00.000463 |
| 0.0006 | 0.00530 | 0.00452 |
| 0.0007 | 0.00516 | 0.00440 |
| 0.0008 | 0.00503 | 0.00428 |
| 0.0009 | 0.00490 | 0.00417 |
| 0.0010 | 0.00476 | 0.00405 |
| 0.0011 | 0.00463 | 0.00393 |
| 0.0012 | 0.00450 | 0.00382 |
| 0.0013 | 0.00436 | 0.00370 |
| 0.0014 | 0.00422 | 0.00358 |
| 0.0015 | 0.00409 | 0.00346 |

Figure 24:
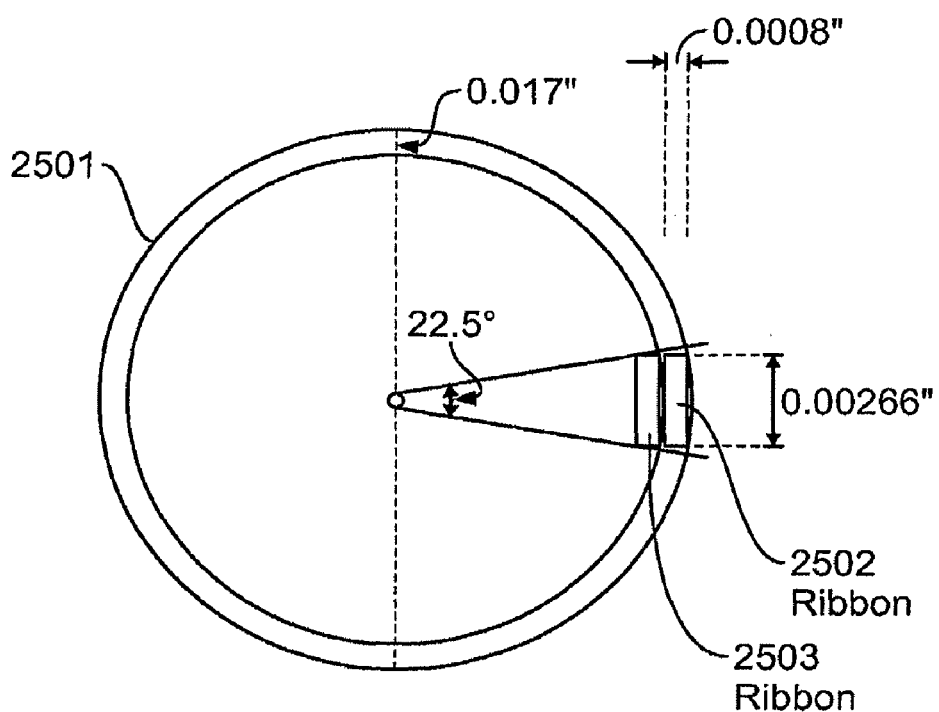
FIG. 24 illustrates an example of determining a ribbon width based on a number of ribbons.

In another example, an occluding device containing 32 ribbons is described. FIG. 24 illustrates an example of determining the ribbon width of a 32-ribbon occluding device based on the number of ribbons that can fit in the protective coil or delivery device 2501. In this example, the protective coil or delivery device 2501 has a diameter of about 0.017 inches and the maximum ribbon width that can fit in the inner circumference of the protective coil or delivery device 2501 provides an arc-angle of about (360 degrees)/(32/2)=22.5 degrees as illustrated in FIG. 24. Hence, to fit 16 ribbons along the inner circumference of the protective coil 2501, the width of the ribbons is determined to be about 0.00266 inches, with a thickness of about 0.00080 inches as illustrated in FIG. 24. Similarly a 20% cushion may be applied to the ribbon widths to provide for narrower ribbon widths to compensate for material tolerance variations. In this example, the modified ribbon widths may be determined based on the new arc-angle requirement of about (360 degrees)/19.2=18.75 degrees. Table 4 provides maximum ribbon widths for a 32-ribbon occluding device.

TABLE 4

| Ribbon Thickness (in) | Calculated max width (in) | 20% cushion width (in) |
| --- | --- | --- |
| 0.0005 | 0.00288 | 0.00242 |
| 0.0006 | 0.00281 | 0.00235 |
| 0.0007 | 0.00273 | 0.00229 |
| 0.0008 | 0.00266 | 0.00223 |
| 0.009 | 0.00258 | 0.00216 |
| 0.0010 | 0.00251 | 0.00210 |

Alternatively, a larger number of ribbons may be included in the occluding device. For example, the strands or ribbons may be increased to greater than 32, such as 40, 44, 48, 50, 56, 60, 64, 70, 76, 80, 90, 100, or more. For any desired number of ribbons, a ribbon width may be determined based on a calculated angle or a ribbon thickness as described. In addition, a cushion may be applied to the ribbon width as described.

Figure 25:
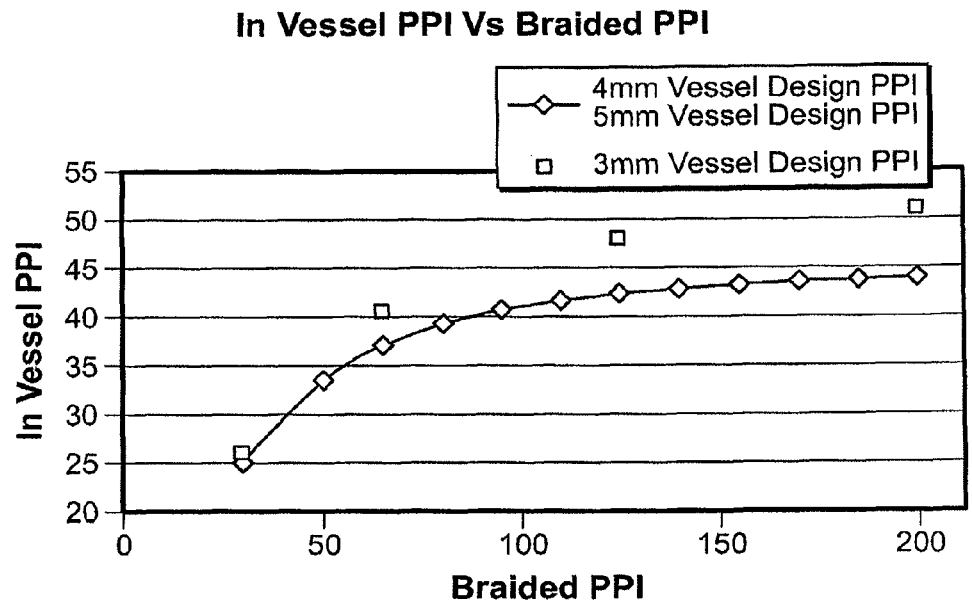
FIG. 25 illustrates a relationship between the PPI of the occluding device in a vessel versus the PPI of the occluding device in a free-standing state.

In another example, oversized occluding devices may be used relative to the vessel. For example, a larger occluding device relative to the size of the vessel lumen may result in enhanced anchoring of the occluding device within the lumen of the vessel. FIG. 25 illustrates a relationship between the PPI of the occluding device in place in the vessel ("in-vessel PPI") versus the PPI of the occluding device in the free-standing state ("braided PPI"). The graph in FIG. 25 demonstrates that for each design, the PPI of the occluding device in place in the vessel approaches a maximum value as the pick count of the occluding device in the free-standing state increases. For example, for the 4 mm vessel design, as the PPI of the free-standing occluding device is increased, the PPI of the occluding device in the vessel increases until the in-vessel PPI reaches about 45. When the in-vessel PPI reaches about 45, further increases in the braided PPI result in only minimal further increases in the in-vessel PPI. Also illustrated in FIG. 25, different vessel designs (e.g., 3 mm vessel design or 5 mm vessel design) result in a similar behavior in which the in-vessel PPI approaches a maximum value for high braided pick counts.

Figure 28:
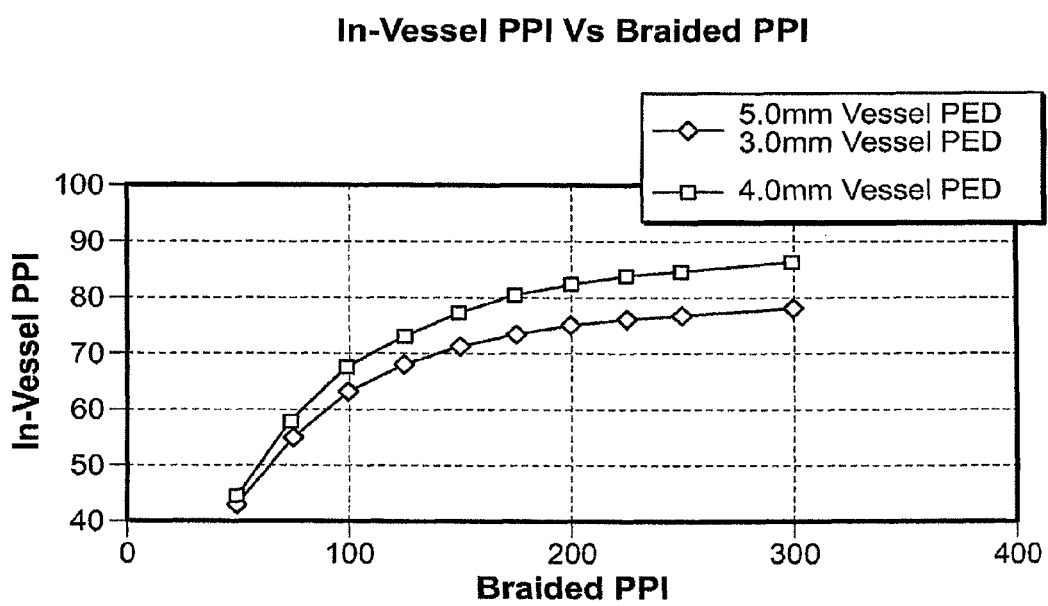
FIG. 28 illustrates the in-vessel PPI as a function of the braided PPI of a 32 ribbon occluding device.

Similarly, FIG. 28 illustrates the in-vessel PPI as a function of the braided PPI of a 32 ribbon occluding device. In the examples illustrated in FIG. 28, the PPI of the occluding device in a vessel ("in-vessel PPI") approaches a higher value as the PPI of the occluding device in a free-standing state ("braided PPI"). FIG. 28 also illustrates alternate vessel designs. As can be seen in the examples of vessel designs of FIG. 28, for each of the vessel designs, the in-vessel PPI approaches a higher value asymptotically as the braided PPI increases.

Figure 26:
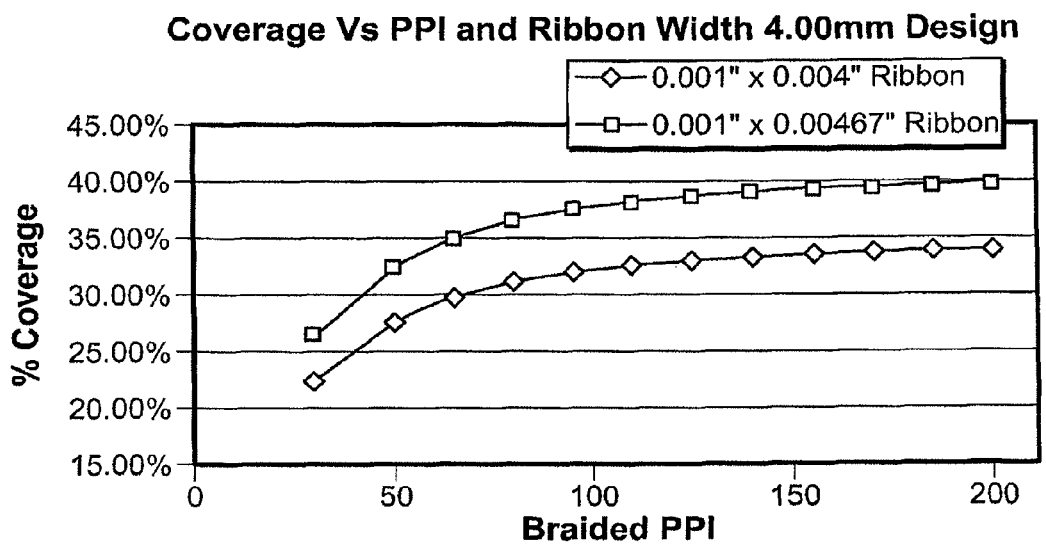
FIG. 26 illustrates an example of a maximum ribbon size that fits in a protective coil.

Similarly, the coverage of the occluding device may be based on ribbon width or braided PPI. FIG. 26 illustrates an example in which the ribbon is about 0.00467 inches wide and 0.001 inches and is the greater ribbon size that fits in the protective coil. As FIG. 26 illustrates, the coverage approaches a greater value of approximately 65-100 PPI range. In this example, the percentage of coverage asymptotically approaches approximately 40% for a 0.001"×0.00467" ribbon and 34% for a 0.001"×0.004" ribbon.

Figure 29:
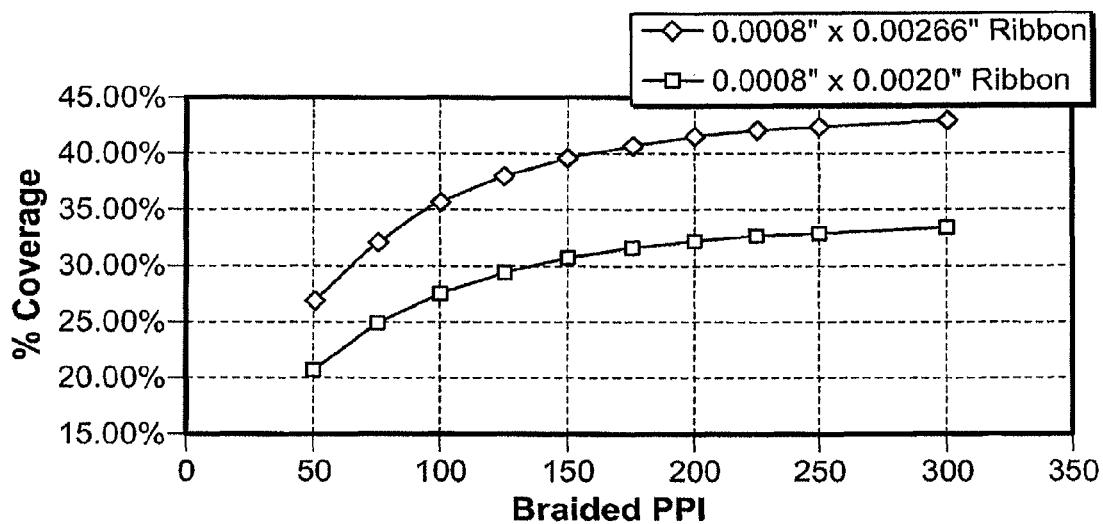
FIG. 29 illustrates the percent coverage as a function of the braided PPI for a 32 ribbon occluding device.

FIG. 29 illustrates the percent coverage as a function of the braided PPI for a 32 ribbon occluding device. As FIG. 29 demonstrates, the % coverage approaches a greater value as the braided PPI in increases. For example, for an occluding device containing about 0.0008×0.00266 inch ribbons, the percent coverage approaches a greater value of about 43% as the braided PPI increases above about 150. Also, for an occluding device containing about 0.0008×0.0020 inch ribbons, the percent coverage approaches a greater value of about 35% as the braided PPI increases above about 150.

Figure 27:
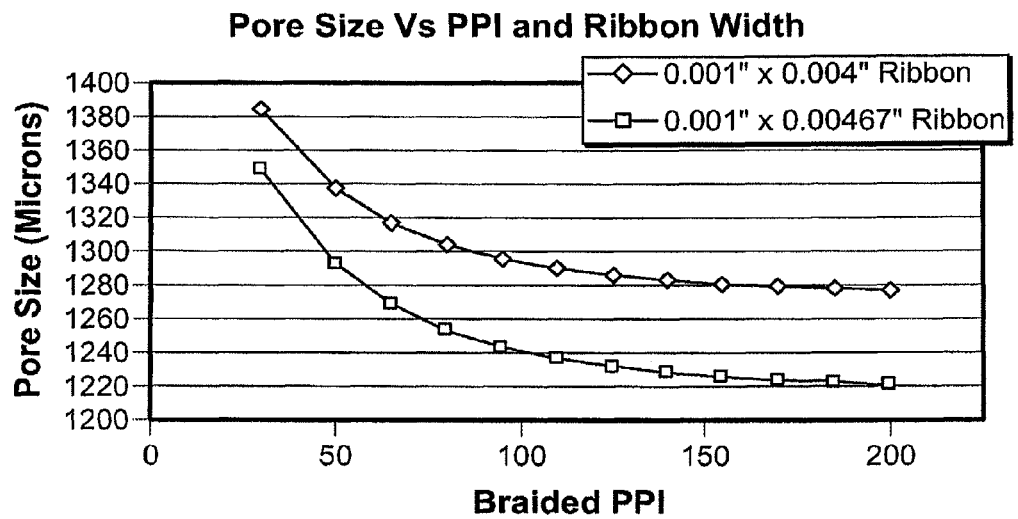
FIG. 27 is a graph showing the opening sizes of braiding elements in the occluding device as a function of the PPI of the lattice structure.

FIG. 27 is a graph showing the opening sizes of braiding elements in the occluding device as a function of the PPI of the lattice structure. As the PPI increases, the opening sizes or spaces through which flow of fluid (e.g., blood) decreases. As the PPI of the lattice structure reaches about 100, the opening sizes of the braiding elements when in place in a vessel asymptotically approaches a minimum value. In the examples illustrated in FIG. 27, for a ribbon size of about 0.001×0.004 inches, the opening sizes of the braiding elements in the lattice structure of an occluding device in a vessel approaches about 1280 microns or less. Similarly, for a ribbon size of about 0.001×0.00467 inches, the opening sizes of the braiding elements in the lattice structure of an occluding device in a vessel approaches about 1220.

Figure 30:
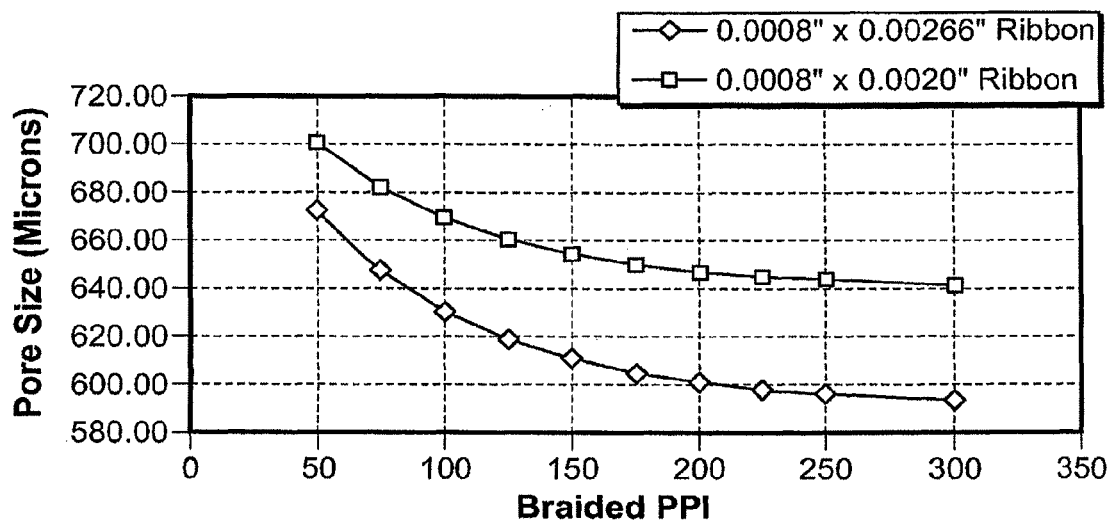
FIG. 30 illustrates the opening sizes of braiding elements in the occluding device as a function of the braided PPI of the lattice structure for a 32 ribbon occluding device.

FIG. 30 illustrates the opening sizes of braiding elements in the occluding device as a function of the braided PPI of the lattice structure for a 32 ribbon occluding device. As FIG. 30 demonstrates, the opening size of braiding elements approaches a lower value as the braided PPI in increases. For example, for an occluding device containing about 0.0008× 0.00266 inch ribbons, the opening size approaches a lower value of about less than 600 microns as the braided PPI increases above about 150. Also, for an occluding device containing about 0.0008×0.0020 inch ribbons, the opening sizes approaches a lower value of about 640 as the braided PPI increases above about 150.

The occluding device 30 is radially compressible and radially expandable without the need for supplemental radially expanding force, such as an inflatable balloon. The occluding device 30 is constructed by winding the two strands (31, 32) in opposite directions. Alternatively, greater than 2 strands may be wound in various directions. For example, 8, 10, 12, 14, 22, 28, 30, 32, 36, 40, 44, 48, 52, 58, 64, 70, 86, 90, 110, 116, 120, 128, 136, 150, or greater strands may be wound in various directions. In an embodiment, the strands 31, 32 are in the shape of rectangular ribbon (See FIG. 4C). The ribbons can be formed of known flexible materials including shape memory materials, such as Nitinol, platinum and stainless steel. In some embodiments, the occluding device 30 is fabricated from platinum/8% tungsten and 35NLT (cobalt nickel alloy, which is a low titanium version of MP35N alloy) alloy wires.

Figure 4C:
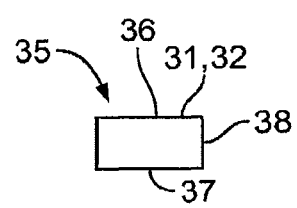
Figure 7:
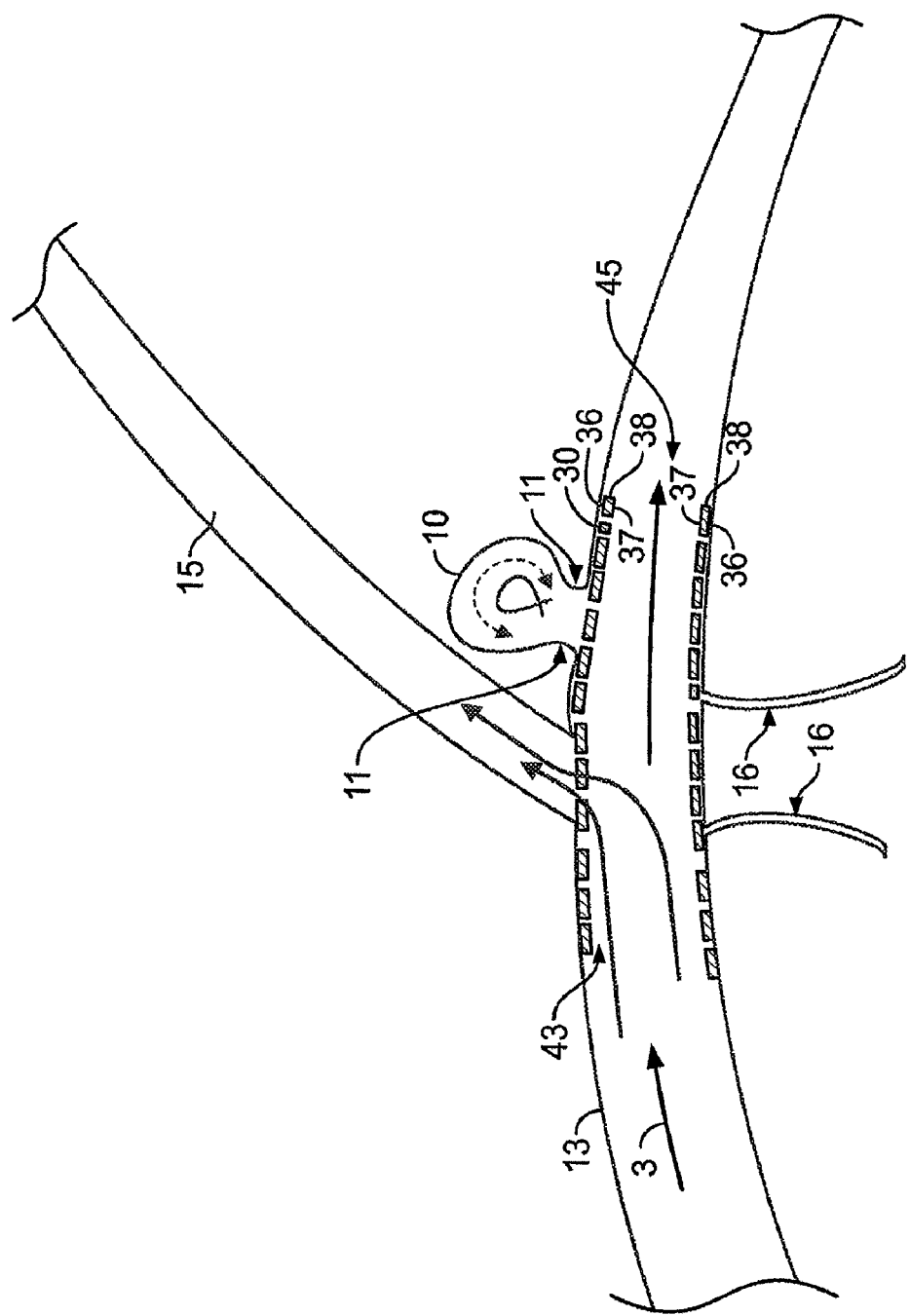
FIG. 7 shows the deployed occluding device inside the lumen of a vessel spanning the neck of the aneurysm, a bifurcation and branch vessels.

The ribbon used as the braiding material for the strands 31, 32 can include a rectangular cross section 35 (FIG. 4C). As shown in FIGS. 4C and 7, the surface 36 that engages an inner surface of the vessel has a longer dimension (width) when compared to the wall 38 that extends between the surfaces 36, 37 (thickness). A ribbon with rectangular cross section has a higher recovery (expansive) force for the same wall thickness when compared to a wire with a circular (round) cross section. Additionally, a flat ribbon allows for more compact compression of the occluding device 200 and causes less trauma to the vascular wall when deployed because it distributes the radial expansion forces over a greater surface area. Similarly, flat ribbons form a more flexible device for a given lattice density because their surface area (width) is greater for a given thickness in comparison to round wire devices.

While the illustrated embodiment discloses a ribbon having a rectangular cross section in which the length is greater than its thickness, the ribbon for an alternative embodiment of the disclosed occluding devices may include a square cross section. In another alternative embodiment, a first portion of the ribbon may include a first form of rectangular cross section and a second portion 39 of the ribbon (FIG. 4B) may include a round, elliptical, oval or alternative form of rectangular cross section. For example, end sections of the ribbons may have substantially circular or oval cross section and the middle section of the ribbons could have a rectangular cross section.

In an alternative embodiment as described above, the occluding device 30 can be formed by winding more than two strands of ribbon. In an embodiment, the occluding device 30 could include as many as sixteen strands of ribbon. In another embodiment, the occluding device 30 can include as many as 32 strands of ribbon, as many as 48 strands of ribbon, as many as 60 strands of ribbon, as many as 80 strands of ribbon, as many as 100 strands of ribbon, as many as 150 strands of ribbon or greater than 150 strands of ribbon, for example. By using standard techniques employed in making radially expanding stents, one can create an occluding device 30 with interstices 34 that are larger than the thickness of the ribbon or diameter of the wire. The ribbons can have different widths. In such an embodiment, the different ribbon(s) can have different width(s) to provide structure support to the occluding device 30 and the vessel wall. The ribbons according to the disclosed embodiments can also be formed of different materials. For example, one or more of the ribbons can be formed of a biocompatible metal material, such as those disclosed herein, and one or more of the ribbons can be formed of a biocompatible polymer.

FIG. 5 shows the intravascular occluding device 30 in a radially compressed state located inside the catheter 25. In one embodiment, the occluding device 30 could be physically attached to the catheter tip. This could be accomplished by constraining the occluding device 30 in the distal segment of the catheter. The catheter 25 is slowly advanced over a guidewire (not shown) by a plunger 50 and when the tip of the catheter 25 reaches the aneurysm, the occluding device is released from the tip. The occluding device 30 expands to the size of the vessel and the surface of the occluding device 30 is now apposed to the vessel wall 15 as shown in FIG. 6.

With reference to FIG. 7, the occluding device 30 is deployed inside the lumen of a cerebral vessel 13 with an aneurysm 10. During its deployment, the proximal end 43 of the occluding device 30 is securely positioned against the lumen wall of the vessel 13 before the bifurcation 15 and the distal end 45 of the occluding device 30 is securely positioned against the lumen wall of the vessel 13 beyond the neck 11 of aneurysm 10. After the occluding device 30 is properly positioned at the desired location within the vessel 13 (for example, see FIG. 7), flow inside the lumen of aneurysm 10 is significantly minimized while the axial flow within the vessel 13 is not significantly compromised, in part due to the minimal thickness of the walls 38.

The flow into the aneurysm 10 will be controlled by the lattice density of the ribbons and the resulting surface coverage. Areas having greater lattice densities will have reduced radial (lateral) flow. Conversely, areas of lesser lattice densities will allow greater radial flow through the occluding device 30. As discussed below, the occluding device 30 can have longitudinally extending (lateral) areas of different densities. In each of these areas, their circumferential densities can be constant or vary. This provides different levels of flow through adjacent lateral areas. The location within a vessel of the areas with greater densities can be identified radiographically so that the relative position of the occluding device 30 to the aneurysm 10 and any vascular branches 15, 16 can be determined. The occluding device 30 can also include radiopaque markers.

Figure 8:
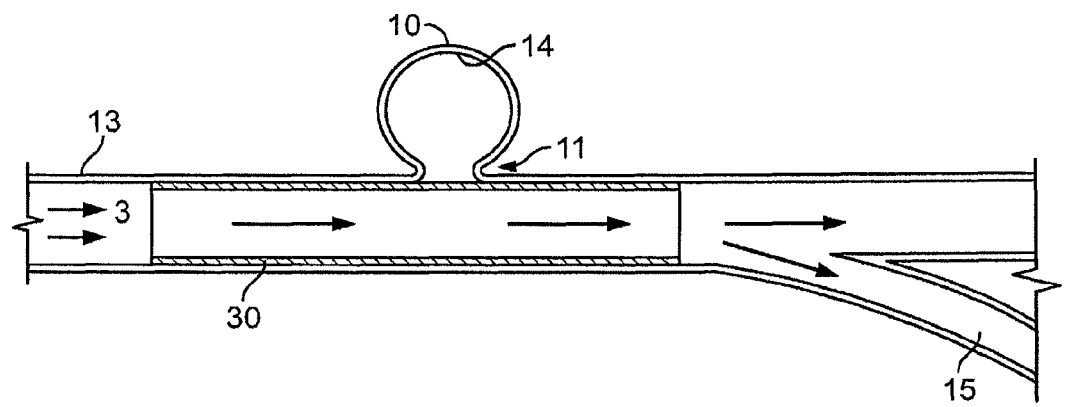
FIG. 8 is a schematic showing the occluding device located in the lumen of a vessel and the change in the direction of the blood flow.

The reduction of blood flow to or within the aneurysm 10 results in a reduction in force against the wall 14 and a corresponding reduction in the risk of vascular rupturing. When the force and volume of blood entering the aneurysm 10 is reduced by the occluding device, the laminar flow into the aneurysm 10 is stopped and the blood within the aneurysm begins to stagnate. Stagnation of blood, as opposed to continuous flow through the lumen 12 of the aneurysm 10, results in thrombosis in the aneurysm 10. This also helps protect the aneurysm from rupturing. Additionally, due to the density of the portion of the occluding device 30 at the bifurcation 15, the openings (interstices) 34 in the occluding device 30 allow blood flow to continue to the bifurcation 15 and the side branches 16 of the vessel. If the bifurcation 15 is downstream of the aneurysm, as shown in FIG. 8, the presence of the occluding device 30 still channels the blood away from the aneurysm 10 and into the bifurcation 15.

In some embodiments, the lattice density of the occluding device 30 may be adjusted so as to result in a delayed occlusion. For example, the lattice density of the occluding device 30 may be configured to gradually reduce the flow of blood into the aneurysm 10 to result in substantial thrombosis in the aneurysm 10 within a time frame after deploying the occluding device 30 to treat the aneurysm. In some embodiments, substantial thrombosis refers to between about 90% and about 95% of the blood within the aneurysm 10 clotting. In some embodiments, substantial thrombosis refers to between about 50% and 99% of the blood within the aneurysm 10 clotting. In some embodiments, substantial thrombosis refers to between about 80% and 95% of the blood within the aneurysm 10 clotting. In some embodiments, substantial thrombosis refers to between about 70% and 98% of the blood within the aneurysm 10 clotting. In some embodiments, substantial thrombosis refers to between about 60% and 99% of the blood within the aneurysm 10 clotting. In some embodiments, substantial thrombosis refers to less than or equal to about 50% of the blood within aneurysm 10 clotting. In some embodiments, substantial thrombosis refers to sufficient clotting of the blood within the aneurysm 10 such that the threat of rupture of the aneurysm 10—for example from the blood flow 3—is reduced or eliminated.

In some embodiments, the time frame associated with the delayed occlusion is about 3 months after deploying the occluding device 30 to treat the aneurysm. In some embodiments, the time frame is between about 2 months and about 4 months. In some embodiments, the time frame is between about 1 month and about 5 months. In some embodiments the time frame is less than or equal to about 1 month or greater than about 5 months. In some embodiments, the time frame is between about 2 weeks and about 4 weeks. In some embodiments, the time frame is between about 3 weeks and about 6 weeks.

The lattice density of the occluding device 30 may be appropriately adjusted to achieve an optimum time frame for delayed occlusion. In some embodiments, the lattice density to achieve an optimum time frame for delayed occlusion is between about 60% and about 95%. In some embodiments, the lattice density to achieve an optimum time frame for delayed occlusion is between about 30% and about 60%. In some embodiments, the lattice density to achieve an optimum time frame for delayed occlusion is less than or equal to about 30% or greater than about 95%. In some embodiments, the lattice density can be combined with other features of the stent to achieve delayed occlusion. For example, the lattice density may be combined with specific features of the individual strands (e.g., cross-section, diameter, perimeter) or the braiding patterns.

Figure 9:
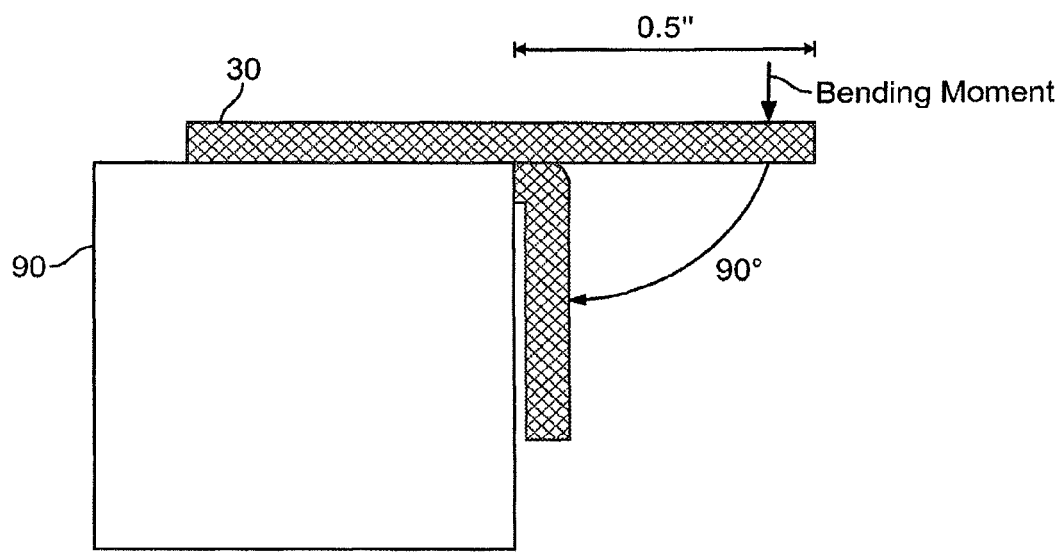
FIG. 9 shows the effect of a bending force on a conventional stent compared to the occluding device of the present disclosure.

The occluding devices described herein have flexibility to conform to the curvature of the vasculature. This is in contrast to coronary stents that cause the vasculature to conform essentially to their shape. The ability to conform to the shape of the vasculature (e.g., in radial compression, bending along an axis of the stent or vasculature, etc.) can be more significant for some neurovascular occluding devices than for some coronary stents, as the vasculature in the brain tends to be smaller and more tortuous. Tables 5 and 6 demonstrate characteristics of the claimed neurovascular occluding device. To demonstrate that the disclosed occluding devices exhibit very desirable bending characteristics, the following experiment was performed. The occluding device made by the inventors was set on a support surface 90 as shown in FIG. 9. About 0.5 inches of the occluding device 30 was left unsupported. Then, a measured amount of force was applied to the unsupported tip until the occluding device was deflected by about 90 degrees from the starting point. A similar length of a coronary stent was subjected to the same bending moment. The results are shown in Table 5. Similar to the reduced compressive force, the occluding device of the present disclosure may require an order of magnitude lower bending moment (0.005 lb-in compared to 0.05 lb-in for a coronary stent). In some embodiments, the braiding pattern, stent diameter, number of ribbons, and other parameters can be adjusted to such that the bending force ranges from about 0.0005 lb-in to about 0.05 lb-in. In some embodiments, the bending force can range from about 0.00025 lb-in to about 0.03 lb-in, from about 0.003 lb-in to about 0.05 lb-in, from about 0.005 lb-in to about 0.01 lb-in, from about 0.01 lb-in to about 0.05 lb-in, from about 0.0025 lb-in to about 0.01 lb-in. In some embodiments, the bending force can range less than about 0.005 lb-in or greater than about 0.05 lb-in.

TABLE 5

Bending Force Required to Bend a 0.5" Cantilever Made by the Occlusion Device

| | |
|---|---|
| Coronary stent | 0.05 lb-in |
| Neurovascular Occluding Device (30) | 0.005 lb-in |

The occluding devices according to the present disclosure also provides enhanced compressibility (i.e., for a given force how much compression could be achieved or to achieve a desired compression how much force should be exerted) compared to coronary stents. An intravascular device that is not highly compressible is going to exert more force on the vessel wall compared to a highly compressible device. This is of significant clinical impact in the cerebral vasculature as it is detrimental to have an intravascular device that has low compressibility. In some embodiments, the braiding pattern, stent diameter, number of ribbons, and other parameters can be adjusted such that the compressive force required to compress the stent 50% of the original diameter ranges from about 0.01 lb to about 0.5 lb. In some embodiments, the compressive force can range from about 0.05 lb to about 0.15 lb, from about 0.07 lb to about 0.1 lb, from about 0.03 lb to about 0.18 lb, from about 0.08 lb to about 0.19 lb, and from about 0.04 lb to about 0.3 lb. In some embodiments, the bending force can range less than about 0.01 lb or greater than about 0.5 lb.

TABLE 6

Figure 10:
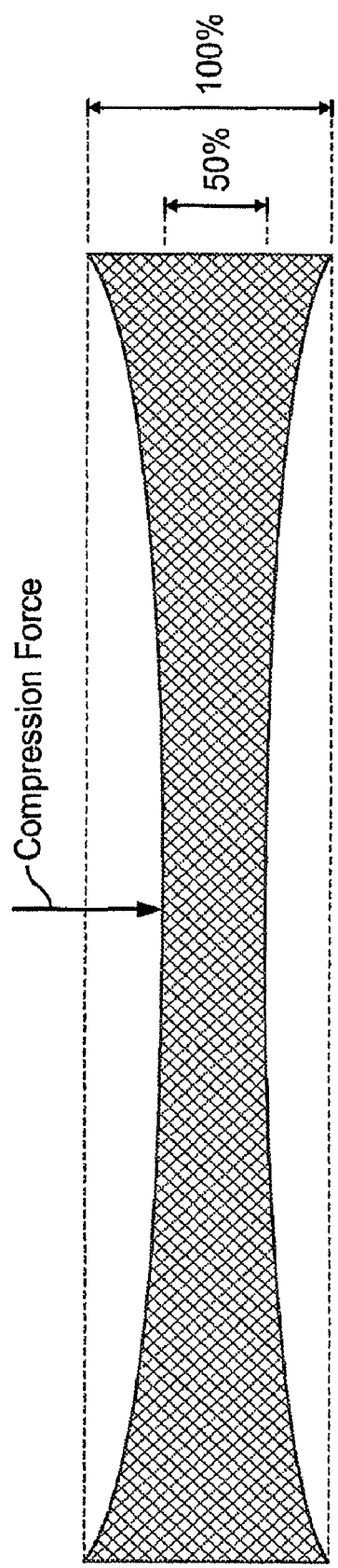
FIG. 10 depicts the flexibility of the occluding device, compared to a traditional stent, by the extent of the deformation for an applied force.

Compressive Force Required to Compress the Occluding device to 50% of the Original Diameter (See FIG. 10)

| | |
|---|---|
| Coronary stent | 0.2 lb |
| Neurovascular Occluding device (30) | 0.02 lb |

FIGS. 33-36 illustrate additional and/or other embodiments of the occluding device 3000. The occluding device 3000 may be expanded or compressed. For example, the entire occluding device 3000, or portions of the occluding device 3000, may be compressed or expanded in an axial direction, radial direction, or both. The occluding device 3000 may be in various configurations or states depending on whether the occluding device 3000 is expanded or compressed. In some embodiments, when the occluding device 3000 is in a certain state, the occluding device 3000 may remain in the same state without any external forces acting on the occluding device 3000. In some embodiments, when the occluding device 3000 is in a certain state, the occluding device 3000 may change to a different state without any external forces acting on the occluding device 3000.

For example, the occluding device 3000 comprises walls 3014 that may change automatically from a compressed configuration (e.g., in a restrained state) to an expanded configuration (e.g., in an unrestrained stated), or vice versa. The walls 3014 may also change from an expanded configuration to a hyperexpanded configuration (e.g., another restrained state), and vice versa. The walls 3014 may exert an expanding force in any direction and/or a compressive force in any direction to allow the occluding device 3000 to change from any one state to another state. In some embodiments, the walls 3014 may have a spring constant k that causes the stent to require a force to change from an expanded, unrestrained state to a compressed state. In some embodiments, the spring constant is of the stent and/or filaments is configured such that the force is between 0.2 lb and about 0.02 lb. For example, the force to change the stent can be between 0.02 lb and 0.1 lb in some embodiments, 0.1 lb and 0.15 lb in some embodiments, and 0.15 lb and 0.2 lb in some embodiments. In some embodiments, the spring constant is such that the force is less than or equal to about 0.02 lb or greater than or equal to about 0.2 lb. The walls 3014 may also have a wall thickness that varies depending on the configuration of the occluding device 3000. In some embodiments, the wall thickness is between about 2 strands and about 4 strands thick when the occluding device 3000 is in the compressed configuration. In some embodiments, the wall thickness is between about 4 strands and about 6 strands thick when the occluding device 3000 is in the compressed configuration. In some embodiments, the occluding device 3000 is less than or equal to about 2 strands or greater than about 6 strands thick when the occluding device 3000 is in the compressed configuration. In some embodiments, the wall thickness is between about 2 strands and about 4 strands thick when the occluding device 3000 is in the expanded configuration. In some embodiments, the wall thickness is less than or equal to about 2 strands or greater than about 4 strands thick when the occluding device 3000 is in the expanded configuration. In some embodiments, the wall thickness is between about 2 strands and about 5 strands thick when the occluding device 3000 is in the hyperexpanded configuration (a configuration beyond the unrestrained, expanded configuration). In some embodiments, the wall thickness is less than or equal to about 2 strands or greater than about 5 strands thick when the occluding device 3000 is in the hyperexpanded configuration.

Figure 33:
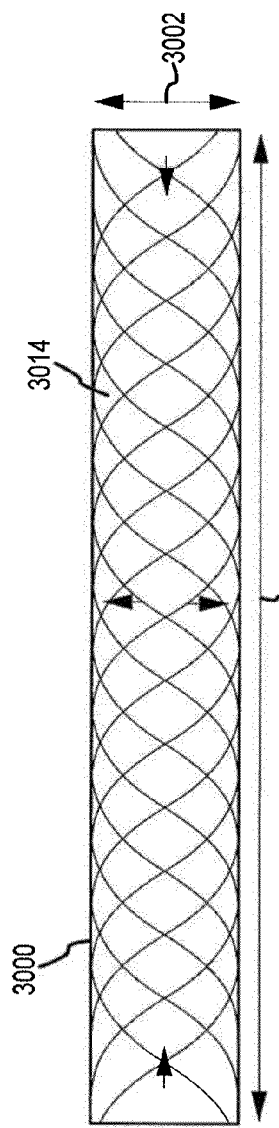
FIG. 33 illustrates an example of an occluding device in a compressed configuration.
Figure 34:
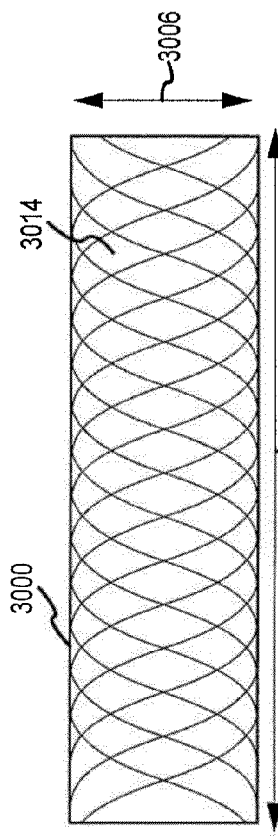
FIG. 34 illustrates an example of an occluding device in an expanded configuration.

In another example, FIG. 33 shows the occluding device 3000 in a compressed configuration. The occluding device 3000 may be in a compressed configuration, for example, when it is stored in the catheter 25 shown in FIG. 5. The walls 3014 of the occluding device 3000, in a compressed configuration, may exert a radially expansive force and an axially compressive force to change from the compressed configuration to an expanded configuration. FIG. 34 illustrates the occluding device 3000 in an expanded configuration. Thus, after deploying the occluding device 3000 from a catheter into a vessel, the occluding device may change from a compressed configuration, as illustrated in FIG. 33, to an expanded configuration, as illustrated in FIG. 34.

Figure 35:
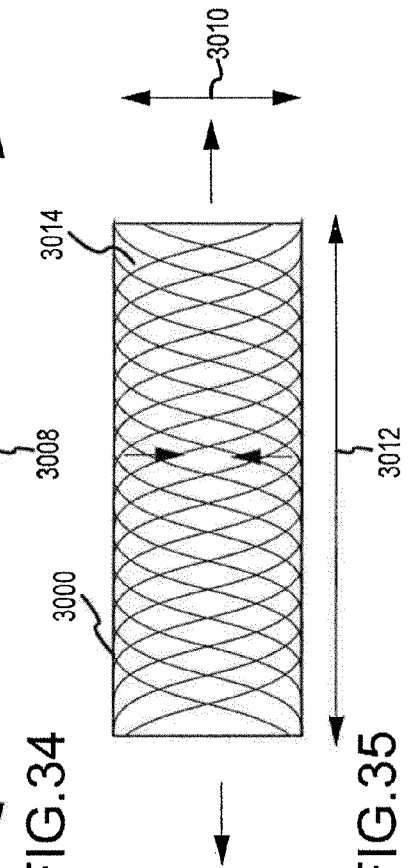
FIG. 35 illustrates an example of an occluding device in a hyperexpanded configuration.

The occluding device 3000 may further be changed from the expanded configuration into a hyperexpanded configuration, as illustrated in FIG. 35. The walls 3014 of the occluding device 3000, in a hyperexpanded configuration, may exert an axially expansive force to change the occluding device 3000 from the hyperexpanded configuration back to the expanded configuration. In some embodiments, the lattice density of the occluding device 3000 is increased when the occluding device 3000 changes from the expanded configuration to the hyperexpanded configuration. In some embodiments, the lattice density of the occluding device 3000 in the expanded configuration is between about 25% and about 35%. In some embodiments, the lattice density of the occluding device 3000 in the expanded configuration is between about 35% and about 50%. In some embodiments, the lattice density of the occluding device 3000 in the expanded configuration is less than or equal to about 25% or greater than about 50%. Correspondingly, the lattice density of the occluding device 3000 in the hyperxpanded configuration, in some embodiments, is between about 50% and about 70%. In some embodiments, the lattice density of the occluding device 3000 in the hyperexpanded configuration is between about 70% and about 95%. In some embodiments, the lattice density of the occluding device 3000 in the hyperexpanded configuration is less than or equal to about 50% or greater than about 95%.

Furthermore, the entire occluding device 3000 or portions of the occluding device 3000 may expand or compress. Correspondingly, the lattice density of the entire occluding device 3000 or the lattice density of portions of the occluding device 3000 may decrease or increase depending on whether an expansive or compressive force, respectively, is applied to the occluding device 3000.

Additionally, the length of the occluding device 3000 may change depending on whether the occluding device 3000 is expanded or compressed in the axial direction. The length of the occluding device 3000 may decrease when the occluding device 3000 is compressed in the axial direction. Alternatively, the length of the occluding device 3000 may increase when the occluding device 3000 is expanded in the axial direction. For example, the length 3008 of the occluding device 3000 in the expanded configuration (FIG. 34) may be less than or about equal to the length 3004 of the occluding device 3000 in the compressed configuration (FIG. 33). This may occur because the walls 3014 of the occluding device 3000 in a compressed configuration are exerting an axially compressive force to change into the expanded configuration. Similarly, the length 3008 of the occluding device 3000 in the expanded configuration (FIG. 34) may be greater than or about equal to the length 3012 of the occluding device 3000 in the hyperexpanded configuration (FIG. 35). This may occur because the walls 3014 of the occluding device 3000 in the hyperexpanded configuration are exerting an axially expansive force to change into the expanded configuration.

The diameter of the occluding device 3000 may also change depending on whether the occluding device 3000 is expanded or compressed in the radial direction. The diameter indicates the cross-sectional open area of the occluding device 3000. Correspondingly, the cross-sectional open area of the occluding device 3000 changes depending on whether the occluding device 3000 is expanded or compressed in the radial direction. The diameter of the occluding device 3000 may decrease when the occluding device 3000 is compressed in the radial direction. Alternatively, the diameter of the occluding device 3000 may increase when the occluding device 3000 is expanded in the radial direction. For example, the diameter 3006 of the occluding device 3000 in the expanded configuration (FIG. 34) may be greater than or about equal to the diameter 3002 of the occluding device 3000 in the compressed configuration (FIG. 33). This may occur because the walls 3014 of the occluding device 3000 in the compressed configuration are exerting a radially expansive force to change into the expanded configuration. Similarly, the diameter 3006 of the occluding device 3000 in the expanded configuration (FIG. 34) may be less than or about equal to the diameter 3010 of the occluding device 3000 in the hyperexpanded configuration (FIG. 35). This may occur because the walls 3014 of the occluding device 3000 in the hyperexpanded configuration are exerting a radially compressive force to change into the expanded configuration.

Figure 36A:
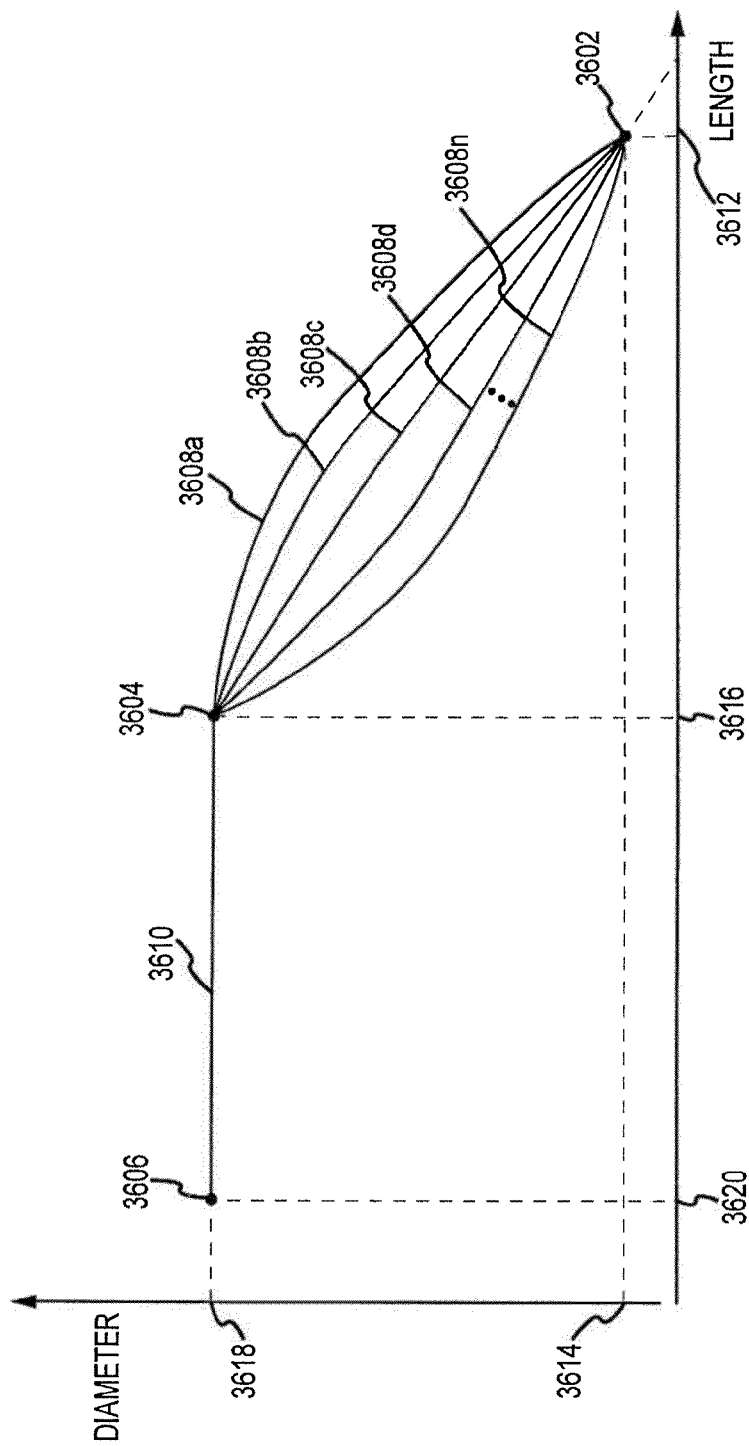
FIGS. 36A, 36B and 36C illustrate various examples of relationships between the length and the diameter of the occluding device.
Figure 36B:
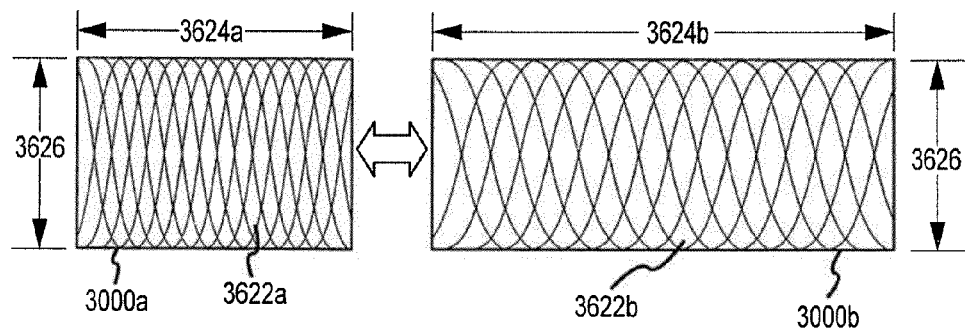
Figure 36C:
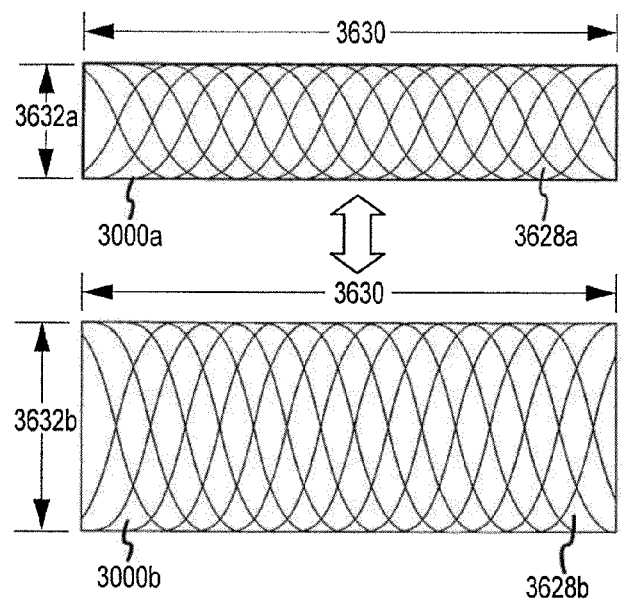

In some embodiments, the diameter of the occluding device 3000 does not increase when changing from the expanded configuration into the hyperexpanded configuration. For example, applying an axially compressive force to the occluding device 3000 in the expanded configuration (thus, decreasing the length 3008) to change into the hyperexpanded configuration does not cause the diameter of the occluding device 3000 to increase. In some embodiments, changing the length of the occluding device 3000, such as by applying an axially compressive or expansive force, does not change the diameter of the occluding device 3000. In some embodiments, changing the diameter of the occluding device 3000, such as by applying a radially compressive or expansive force, does not change the length of the occluding device 3000. FIGS. 36A, 36B and 36C illustrate various examples of relationships between the length and the diameter of the occluding device 3000. As shown in FIG. 36A, point 3602 represents the greater length and the lesser diameter of the occluding device 3000. Point 3602 represents the greater length 3612 and the lesser diameter 3614 that the occluding device 3000 can be "stretched" to. That is, by applying an axially expansive force and/or a radially compressive force on the occluding device 3000, occluding device 3000 may reach this point 3602.

The greater length 3612 or the lesser diameter 3614 of the occluding device 3000 may vary depending on the treatment that the occluding device 3000 is used for, the materials used in making occluding device 3000, the size of any storage or deployment devices utilizing the occluding device 3000, or other factors. In some embodiments, the greater length 3612 of the occluding device 3000 is between about 2 times and about 5 times the unrestrained length 3616. In some embodiments, the greater length 3612 is between about 5 times and about 10 times the unrestrained length 3616. In some embodiments, the greater length 3612 is less than or equal to about 2 times or greater than about 10 times the unrestrained length 3616. In some embodiments, the greater length 3612 may be when the occluding device 3000 is placed within a catheter. The greater length 3612 may be longer or shorter than the catheter. In some embodiments, the greater length 3612 when the occluding device 3000 is placed within a catheter is between about 40 mm and about 60 mm. In some embodiments, the greater length 3612 when the occluding device 3000 is placed within a catheter, the greater length 3612 is between about 25 mm and about 75 mm. In some embodiments, the greater length 3612 when the occluding device 3000 is placed within a catheter, the greater length 3612 is less than or equal to about 25 mm or greater than about 75 mm.

In some embodiments, the lesser diameter 3614 of the occluding device 3000 is between about 1% and about 5% of the unrestrained diameter 3618. In some embodiments, the lesser diameter 3614 is between about 0.5% and about 10% of the unrestrained diameter 3618. In some embodiments, the lesser diameter 3614 is between about 2% and about 15% of the unrestrained diameter 3618. In some embodiments, the lesser diameter 3614 is between about 3% and about 20% of the unrestrained diameter 3618. In some embodiments, the lesser diameter 3614 is less than or equal to about 0.5% or greater than about 20% of the unrestrained diameter 3618. In some embodiments, the lesser diameter 3614 may be when the occluding device 3000 is placed within a catheter. In some embodiments, the lesser diameter 3614 when the occluding device 3000 is placed within a catheter is between about 0.026 inches and about 0.027 inches. In some embodiments, the lesser diameter 3614 when the occluding device 3000 is placed within a catheter is between about 0.020 inches and about 0.03 inches. In some embodiments, the lesser diameter 3614 when the occluding device 3000 is placed within a catheter is less than or equal to about 0.020 inches or greater than about 0.03 inches.

Intervals 3608 (as represented by intervals 3608a, 3608b, 3608c, 3608d, 3608e through 3608n in FIG. 36A) represent any of the states of the occluding device 3000 when the occluding device 3000 is in a compressed configuration and/or changing from a compressed configuration into an expanded configuration or vice versa. In some embodiments, the length of the occluding device 3000 does not vary with the diameter of the occluding device 3000. In some embodiments, the length of the occluding device 3000 varies with the diameter of the occluding device 3000 in any manner, such as linearly, inversely, exponentially, or logarithmically.

Point 3604 represents the unrestrained length 3616 and the unrestrained diameter 3618 of the occluding device 3000 when the occluding device 3000 is in the expanded configuration. The unrestrained length 3616 or the unrestrained diameter 3618 of the occluding device 3000 may also vary depending on the treatment that the occluding device 3000 is used for, the materials used in making occluding device 3000, the size of any storage or deployment devices utilizing the occluding device 3000, or other factors. For example, the unrestrained length 3616 may be appropriately long enough for the treatment of aneurysms, such as being at least being longer than the neck of an aneurysm. In some embodiments, the unrestrained length 3616 is between about 8 mm and about 10.5 mm. In some embodiments, the unrestrained length 3616 is between about 5 mm and about 15 mm. In some embodiments, the unrestrained length 3616 is less than or equal to about 5 mm or greater than about 15 mm.

The unrestrained diameter 3618 of the occluding device 3000 may at least be approximately greater than the diameter of the blood vessel in which the occluding device 3000 is deployed in. That is, the unrestrained diameter 3618 may be greater than the diameter of the vessel such that a frictional force created between the contact of the occluding device 3000 and the walls of the vessel is great enough to prevent or reduce the likelihood the occluding device 3000 from migrating through the vessel. In some embodiments, the unrestrained diameter 3618 is between about 2.25 mm and about 5.25 mm. In some embodiments, the unrestrained diameter 3618 is between about 1.75 mm and about 6.5 mm. In some embodiments, the unrestrained diameter 3618 is less than or equal to about 1.75 mm or greater than about 6.5 mm.

In some embodiments, the number of strands that may be used for occluding device 3000 depends on the unrestrained diameter 3618. In some embodiments, about 48 strands may be used for occluding device 3000 for an unrestrained diameter 3618 between about 2.75 mm and about 4.25 mm. In some embodiments, about 64 strands may be used for occluding device 3000 for an unrestrained diameter 3618 between about 4.5 mm and about 6.0 mm. In some embodiments, about 72 strands may be used for occluding device 3000 for an unrestrained diameter 3618 greater than or equal to about 6.0 mm. In some embodiments, about 32 strands may be used for occluding device 3000 for an unrestrained diameter 3618 less than or equal to about 2.5 mm. These ranges and values can vary depending on desired properties, such as diameters and porosity.

Interval 3610 represents any of the states of the occluding device 3000 when the occluding device 3000 is in a hyperexpanded configuration and/or changing from an expanded configuration into a hyperexpanded configuration or vice versa. In some embodiments, decreasing the length of the occluding device 3000, for example by applying an axially compressive force, does not cause the diameter of the occluding device 3000 to increase. Rather, the diameter may remain substantially the same as illustrated by interval 3610.

Point 3606 represents the lesser length 3620 and a greater diameter 3618 of the occluding device 3000. The lesser length 3620 and the greater diameter 3618 of the occluding device 3000 may also vary depending on the treatment that the occluding device 3000 is used for, the materials used in making occluding device 3000, or other factors. For example, the lesser length 3620 may be small enough to allow for the greater lattice density needed to treat an aneurysm or other diseases. In some embodiments, the lesser length 3620 is between about 30% and about 50% of the unrestrained length 3616. In some embodiments, the lesser length 3620 is between about 50% and about 75% of the unrestrained length 3616. In some embodiments, the lesser length 3620 is less than or equal to about 30% or greater than about 75% of the unrestrained length 3616. In some embodiments, the greater diameter 3618 is the same as the unrestrained diameter 3618. In some embodiments, the greater diameter 3618 is 110% of the unrestrained diameter 3618. In some embodiments, the greater diameter 3618 is between about 101% and about 115% of the unrestrained diameter 3618. In some embodiments, the greater diameter 3618 is less than or equal to about 101% or greater than about 115% of the unrestrained diameter 3618.

FIG. 36B illustrates an example of a relationship between the length 3624 (as shown by lengths 3624a and 3624b) and the diameter 3626 of the occluding device 3000 (as shown by occluding devices 3000a and 3000b). The occluding device 3000a may be in a first configuration, and comprises a first length 3624a, a diameter 3626, and a first lattice density 3622a. An axially expansive force may be applied to the occluding device 3000a. In some embodiments, applying an axially expansive force decreases the lattice density and increases the length. For example, by applying an axially expansive force to the occluding device 3000a in the first configuration, the occluding device 3000a may expand into a second configuration of the occluding device 3000b. Thus, the second lattice density 3622b may be lower than the first lattice density 3622a, and the second length 3624b may be greater than the first length 3624a.

Similarly, in some embodiments, applying an axially compressive force increases the lattice density and decreases the length. For example, by applying an axially compressive force to the occluding device 3000b in the second configuration, the occluding device 3000b may compress into the first configuration of the occluding device 3000a. Thus, the first lattice density 3622a may be greater than the second lattice density 3622b, and the first length 3624a may be lower than the second length 3624b. In some embodiments, applying an axially compressive or expansive force does not change the diameter 3626 of the occluding device 3000. For example, the diameter 3626 remains substantially the same between the occluding device 3000a in the first configuration and the occluding device 3000b in the second configuration.

FIG. 36C illustrates an example of a relationship between the length 3630 and the diameter 3632 (as shown by diameters 3632a and 3632b) of the occluding device 3000 (as shown by occluding devices 3000a and 3000b). The occluding device 3000a may be in a first configuration, and comprises a length 3630, a first diameter 3632a, and a first lattice density 3628a. A radially expansive force may be applied to the occluding device 3000a. In some embodiments, applying a radially expansive force decreases the lattice density and increases the diameter. For example, by applying a radially expansive force to the occluding device 3000a in the first configuration, the occluding device 3000a may expand into a second configuration of the occluding device 3000b. Thus, the second lattice density 3628b may be lower than the first lattice density 3628a, and the second diameter 3632b may be greater than the first diameter 3632a.

Similarly, in some embodiments, applying a radially compressive force increases the lattice density and decreases the diameter. For example, by applying a radially compressive force to the occluding device 3000b in the second configuration, the occluding device 3000b may compress into the first configuration of the occluding device 3000a. Thus, the first lattice density 3628a may be greater than the second lattice density 3628b, and the first diameter 3632a may be lower than the second diameter 3632b. In some embodiments, applying a radially compressive or expansive force does not change the length 3630 of the occluding device 3000. For example, the length 3630 remains substantially the same between the occluding device 3000a in the first configuration and the occluding device 3000b in the second configuration.

Figure 11A:
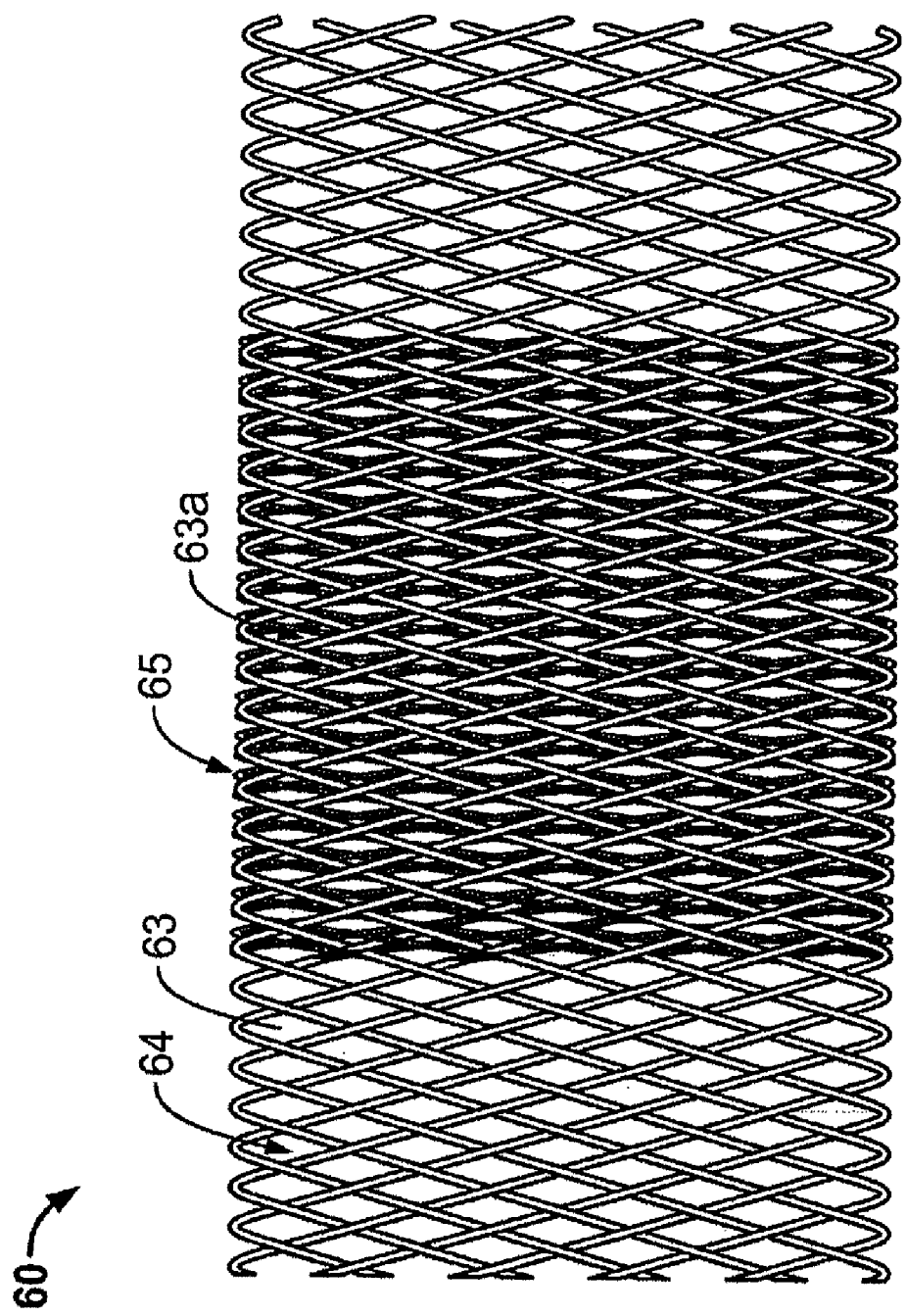
Figure 12:
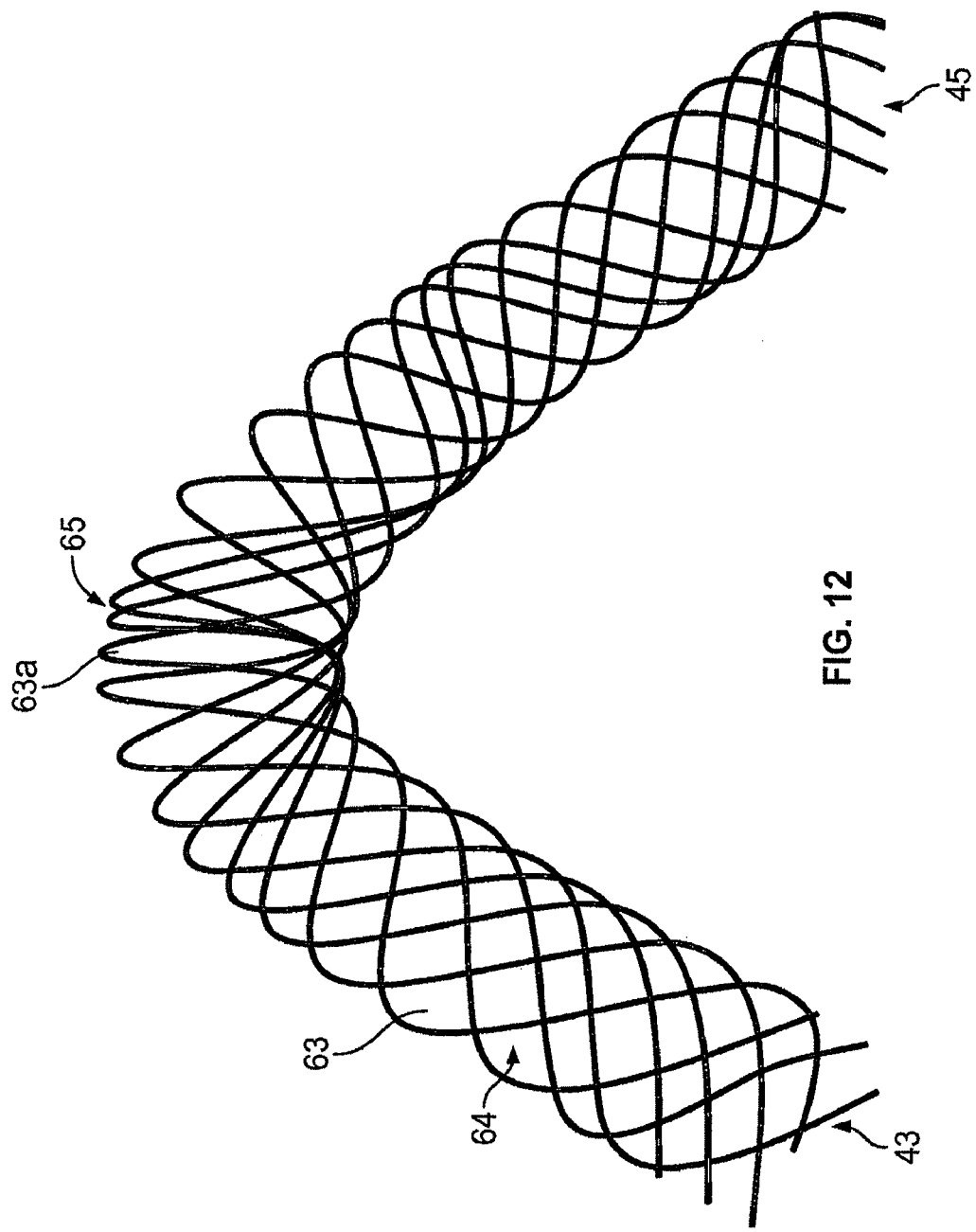
FIG. 12 illustrates the difference in lattice density due to the non-uniform density of the braiding of the occluding device.
Figure 13:
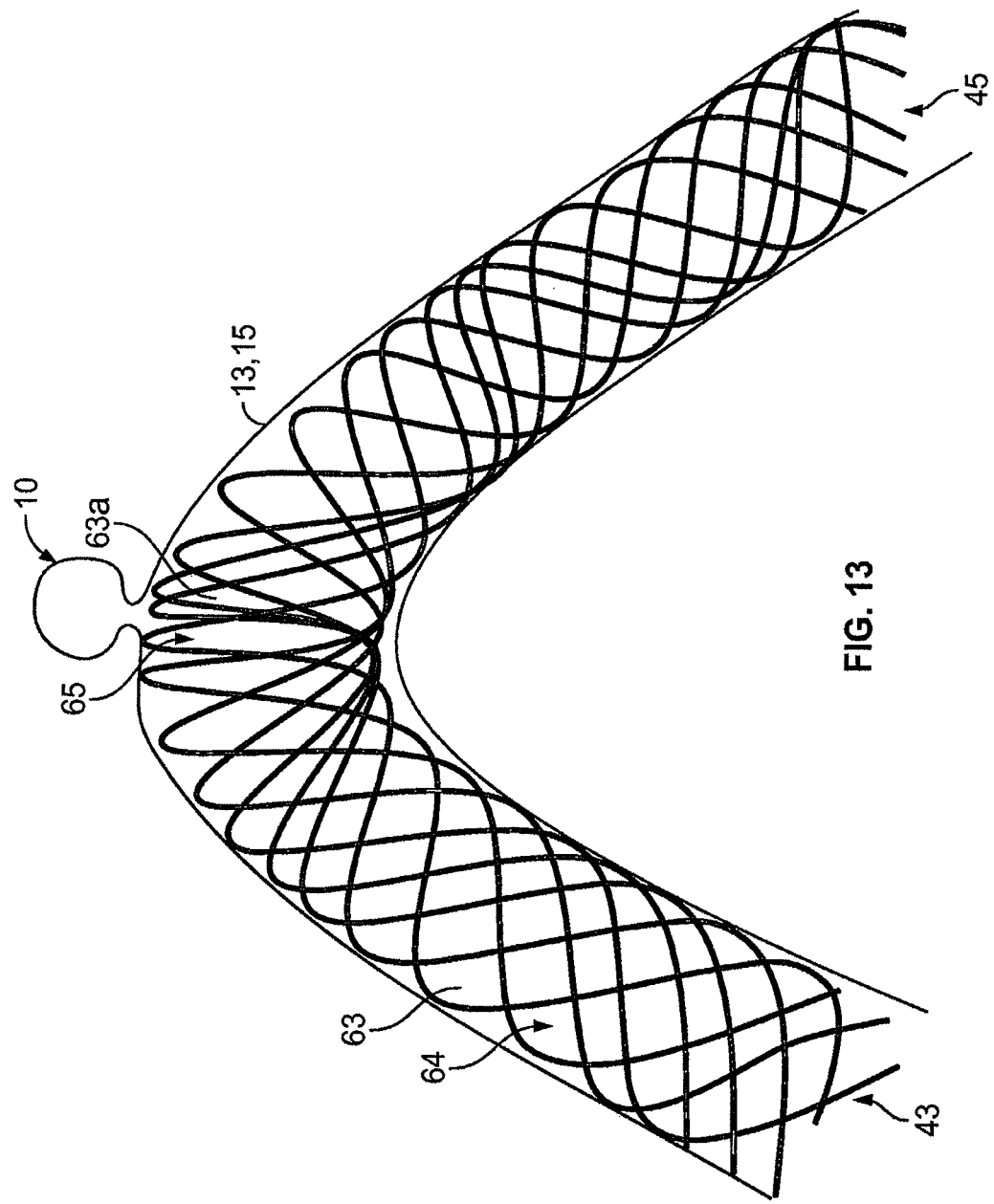
FIG. 13 shows the varying lattice density occluding device covering the neck of an aneurysm.

FIGS. 11-13 show an embodiment of the occluding device 60 in which the lattice structure 63 of the occluding device 60 is non-uniform across the length of the occluding device 60. In the mid-section 65 of the occluding device 60, which is the section likely to be deployed at the neck of the aneurysm, the lattice density 63a is intentionally increased to a value significantly higher than the lattice density elsewhere in the occluding device 60. For example, as seen in FIG. 11A, lattice density 63a is significantly higher than the lattice density 63 in adjacent section 64. FIGS. 11B-11G illustrates other examples in which the lattice density varies across the length of the occluding device 60. In some examples, the sections of the occluding device 60 with higher lattice densities 63a may be at the end, the middle, or other locations of the occluding device 60. The occluding device 60 may also have different lattice densities across the length of the occluding device 60. For example, as shown in FIGS. 11F and 11G, the occluding device 60 may have a section with a lattice density 63b which is higher than lattice density 63 and lower than lattice density 63a. At one extreme, the lattice density could be 100%, i.e., the occluding device 60 is completely impermeable. In another embodiment, the lattice density 63A in mid-section 65 could be about 50%, while the lattice density in the other sections 64 of the occluding device is about 25%. FIG. 12 shows such an occluding device 60 in a curved configuration and FIG. 13 shows this occluding device 60 deployed in the lumen of a vessel. FIG. 13 also illustrates the part of the occluding device 60 with increased lattice density 63A positioned along the neck of aneurysm 10. As with any of the disclosed occluding devices, the lattice density of at least one portion of occluding device 60 can be between about 20% and about 30%. In some embodiments, the lattice density of at least one portion of occluding device 60 can be between about 30% and 65%. In some embodiments, the lattice density of at least one portion of occluding device 60 can be between about 65% and 95%. In some embodiments, the lattice density of at least one portion of occluding device 60 can be less than or equal to about 20% or greater than about 95%.

In some embodiments, increasing the lattice density of a portion of the stent decreases a porosity of stent portion. Conversely, decreasing the lattice density of a stent portion increases the porosity of the stent portion. In some embodiments, the changing of the lattice density, or porosity, is called packing or dynamic packing.

The occluding device 60 may also be described in terms of porosity. According to one embodiment, the porosity of occluding device 60 may be equal to a ratio of an open surface area of the occluding device 60 to a total surface area of the occluding device 60. Occluding device 60 may comprise a plurality of braided strands, which forms pores in open areas between the strands.

In some embodiments, the pores have an average pore length. The average pore length may be any pore length suitable for aneurysm treatment or other types of treatments. In some embodiments, the average pore length is about 0.43 mm. In some embodiments, the average pore length is between about 0.15 mm and about 0.40 mm. In some embodiments, the average pore length is between about 0.4 mm and about 0.65 mm. In some embodiments, the average pore length is less than or equal to about 0.15 mm or greater than about 0.65 mm.

The pores may either increase or decrease in size depending on the structure of the occluding device 60. For example, the porosity of a portion of the occluding device 60 can be reduced by axially compressing the portion of the occluding device 60. By axially compressing the portion of the occluding device 60, the open surface area decreases as the braided strands are compressed closer together, resulting in a reduced porosity.

When the axially compressed portion of the occluding device 60 is unrestrained, the occluding device 60 may expand, resulting in an increased porosity. In some embodiments, the porosity of occluding device 60 can be between about 70% and about 80%. In some embodiments, the porosity of occluding device 60 can be between about 35% and 70%. In some embodiments, the porosity of occluding device 60 can be between about 5% and 35%. In some embodiments, the porosity of occluding device 60 can be less than or equal to about 5% or greater than about 80%.

In some embodiments, the porosity is related to the pore length. For example, in some embodiments, the porosity multiplied by the average pore length is about 0.3 mm. In some embodiments, the porosity multiplied by the average pore length is between about 0.15 mm and about 0.3 mm. In some embodiments, the porosity multiplied by the average pore length is between about 0.3 mm and about 0.45 mm. In some embodiments, the porosity multiplied by the average pore length is less than or equal to about 0.15 mm or greater than about 0.45 mm. In one example, the porosity at 70% multiplied by the average pore length at 0.43 mm gives 0.3 mm.

In some embodiments, the porosity is related to the thickness of the braided strands. The braided strands may have an average strand thickness. In some embodiments, the average strand thickness is about 0.003 inches. In some embodiments, the average strand thickness is between about 0.001 inches and about 0.003 inches. In some embodiments, the average strand thickness is between about 0.003 inches and about 0.005 inches. In some embodiments, the average strand thickness is less than or equal to about 0.001 inches or greater than about 0.005 inches. The braided strands may comprise a ribbon having a width greater than its thickness. In other examples, the ribbon may have a width less than or equal to its thickness. In some embodiments, the porosity multiplied by the average strand thickness is about 0.002 inches. In some embodiments, the porosity multiplied by the average strand thickness is between about 0.001 inches and about 0.002 inches. In some embodiments, the porosity multiplied by the average strand thickness is between about 0.002 inches and about 0.004 inches. In some embodiments, the porosity multiplied by the average strand thickness is less than or equal to about 0.001 inches or greater than about 0.004 inches. For example, the porosity at 70% multiplied by the average strand thickness at 0.003 inches gives 0.002 inches.

In some embodiments, the pore size is related to the thickness of the braided strands. In some embodiments, the average pore length multiplied by the average strand thickness is about $9.4 \times 10^{-5}$ in$^2$. In some embodiments, the average pore length multiplied by the average strand thickness is between about $4 \times 10^{-5}$ in and about $14 \times 10^{-5}$ in$^2$. In some embodiments, the average pore length multiplied by the average strand thickness is less than or equal to about $4 \times 10^{-5}$ in or greater than about $14 \times 10^{-5}$ in$^2$. For example, the average pore length at 0.6 mm multiplied by the average strand thickness at 0.004 inches results in a value of $9.4 \times 10^{-5}$ in$^2$.

In some embodiments, the porosity of occluding device 60 is related to the volume of the pore and is configured to facilitate endotheliazation of the stented vessel. In such embodiments, that pore area can be multiplied by the average or actual stent thickness to determine the volume of space defined by each stent pore. By selecting a desired stent pore volume, endotheliazation of the stented vessel can be enhanced. In some embodiments, other parameters may be used to optimize or enhance functions of the stent, such as the average pore length, the average strand thickness, the average pore size, or other dimensions.

Figure 14:
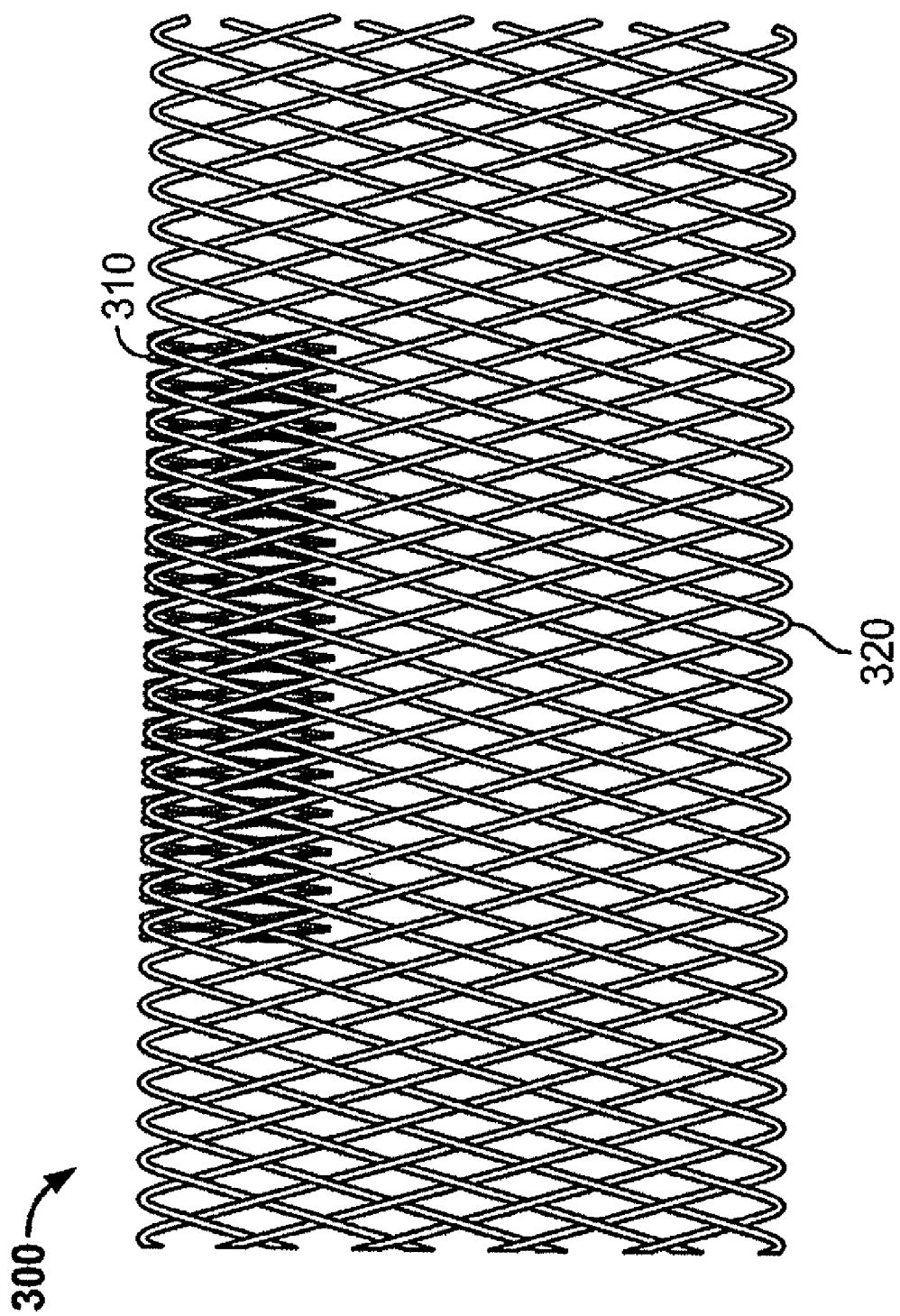
FIGS. 14 and 15 show embodiments of the vascular occluding device where the lattice density is asymmetrical about the longitudinal axis near the aneurysm neck.
Figure 15:
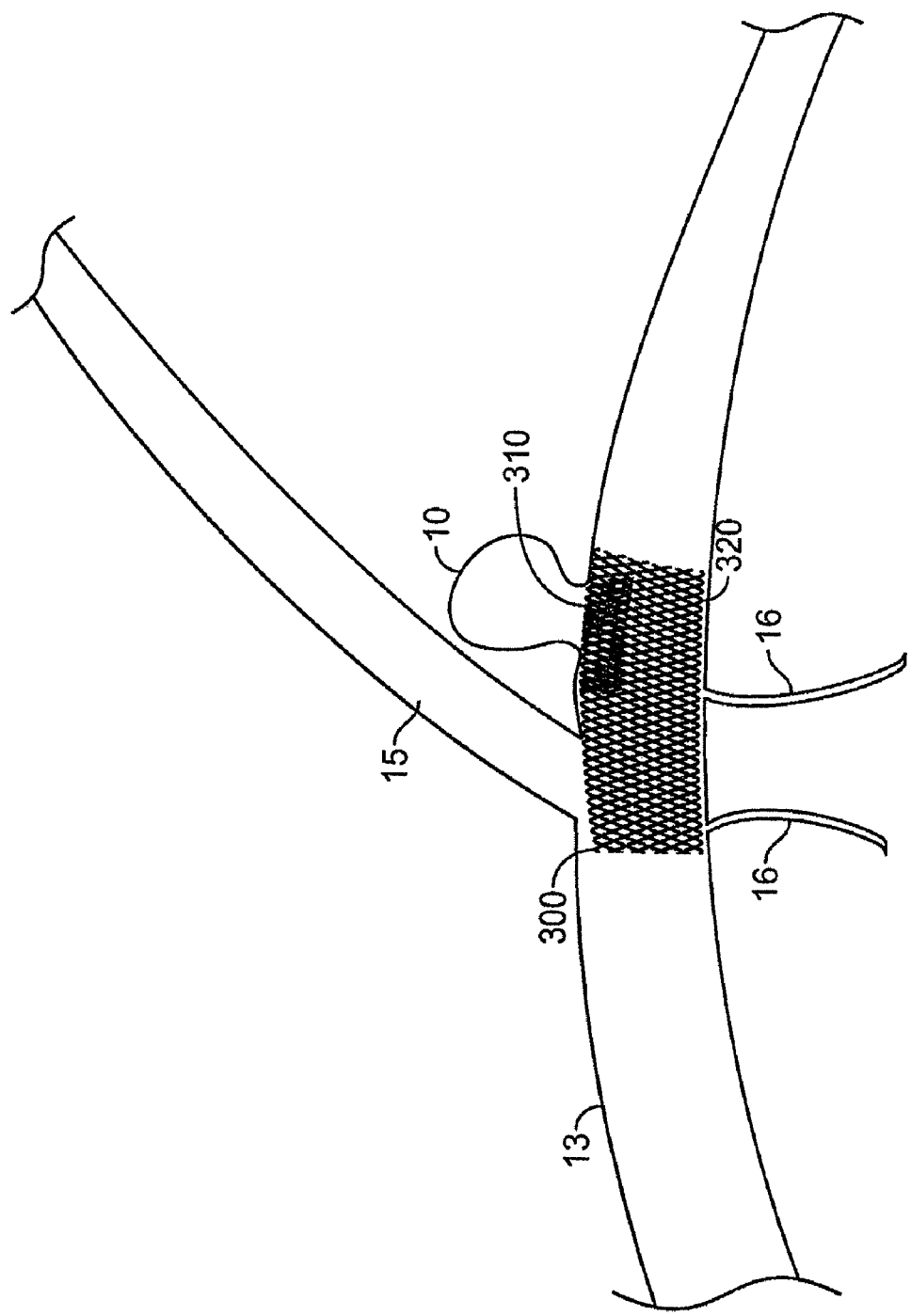

Another embodiment of the occluding device 300 is shown in FIGS. 14 and 15. In this embodiment, the occluding device 300 is deployed in lumen of a vessel with an aneurysm. The occluding device 300 includes a surface 310 that faces the lumen of the aneurysm. This surface 310 has a significantly higher lattice density (smaller and/or fewer interstices) compared to the diametrically opposite surface 320. Due to the higher lattice density of surface 310, less blood flows into the lumen of the aneurysm. However, there is no negative impact on the blood flow to the side branches as the lattice density of the surface 320 facing the side branches is not reduced.

As set forth in the examples above, different portions of the occluding device may have different lattice densities such that flow of fluids or blood may be controlled based on the location within the occluding device. The lattice densities may further be controlled by an input received at the occluding device. The input for controlling the lattice densities of different portions of the occluding device may include, for example, a pressure or motion force applied to a portion of the occluding device. The occluding device in this example may include helically-wound material such as strands or ribbons in a lattice structure as described herein. The strands that are helically wound may be movable relative to each other. For example, a first strand and a second strand may be helically wound to form a lattice structure that includes crossing strands (the first strand and the second strand may cross over each other) interspersed with openings between the strands.

In another example, the lattice structure formed by crossing strands of the occluding device may be adjustable based on the input as described (e.g., motion, pressure or force input). When the input is received at the occluding device, the strands may move relative to each other. For example, a portion of the first strand may move closer to a corresponding portion of the second strand and a second portion of the first strand may also move farther from a corresponding first portion of the second strand. Hence, in this example, the spacing between the first and second strands of helically wound material forming the lattice structure of the occluding device may vary to create different lattice densities. Different portions of an occluding device may have different lattice densities when strands in one portion of the occluding device move closer to each other while strands in another portion of the occluding device move farther away from each other.

Also, the relative movement of the strands may be controlled based on an input received at the occluding device. As set forth above, the input may include any type of input for moving or adjusting the occluding device including, for example, pressure, force, motion, rotation, or other similar input.

The occluding device, or stent, may be placed into a blood vessel and a certain portion of the occluding device may contain a high lattice density while retaining a lower lattice density in a different portion of the occluding device. The received input may control the placement and/or lattice density of the occluding device to achieve a desired lattice density at a selected portion of the occluding device. Thus, the input received at the occluding device may cause a first portion of the occluding device to have a first lattice density and a second portion of the occluding device to have a second lattice density in which the first lattice density and the second lattice density are different.

In one example, a user may insert the occluding device into the blood vessel and may apply pressure on the occluding device to cause an adjustment of the lattice density of the occluding device. In another example, a motion force may be applied to the occluding device such that the strands of the occluding device forming the lattice structure may move relative to one another in at least one portion of the occluding device. The strands may also be rearranged differently at different portions of the occluding device such that the lattice density may vary from one portion of the occluding device to another portion of the occluding device.

Figure 31:
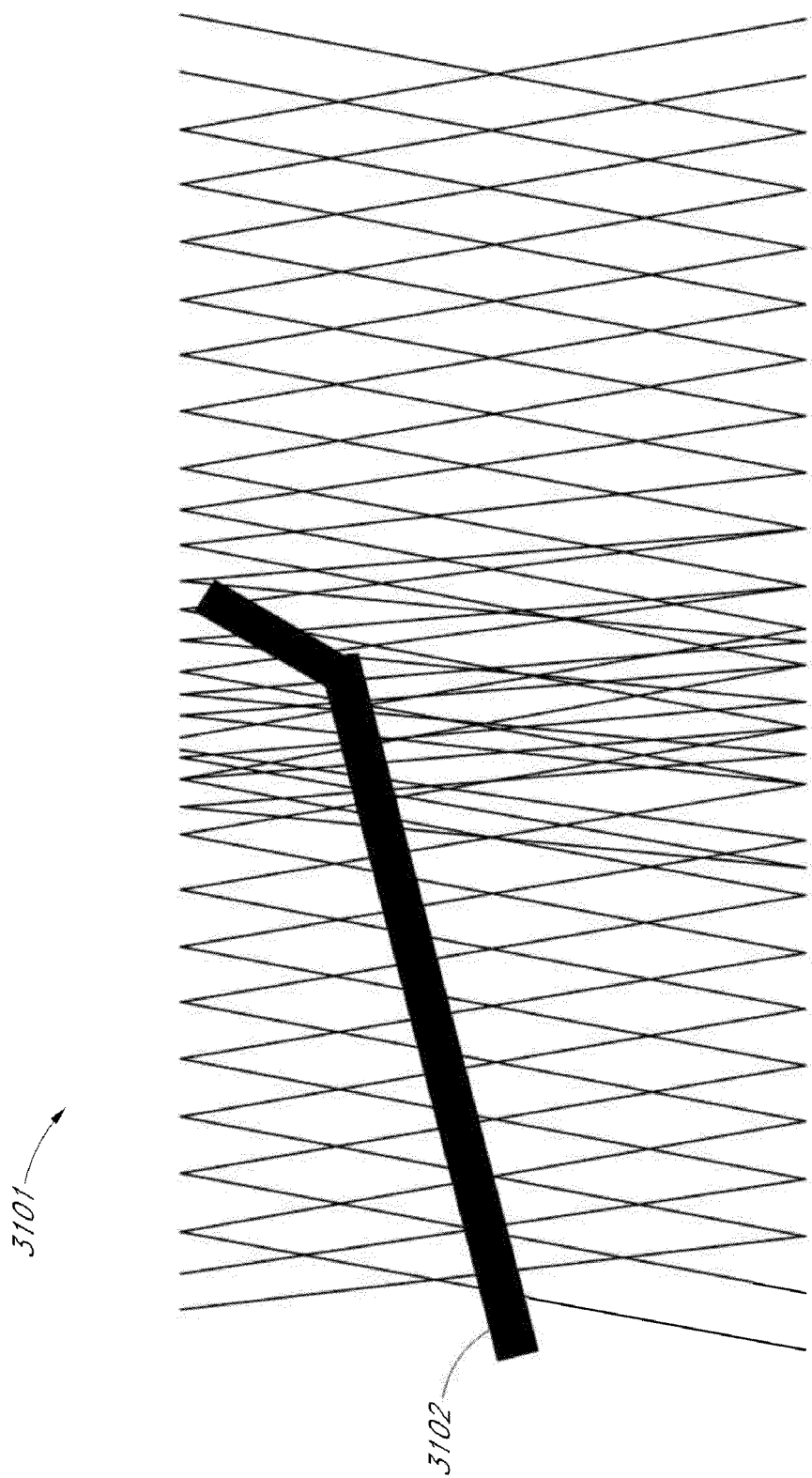
FIG. 31 illustrates an example of a lattice density adjusting implement for adjusting lattice density in an occluding device.

For example, the occluding device may include a lattice density adjusting implement such that pressure exerted by the lattice density adjusting implement on a portion of the occluding device may cause the lattice density of the portion of the occluding device acted upon by the lattice density adjusting implement to obtain a desired lattice density. FIG. 31 illustrates an example of an occluding device 3101 containing a lattice density adjusting implement 3102 for adjusting the lattice density at any desired portion of the occluding device 3101. The user may exert a force on a proximal end of the lattice density adjusting implement 3102 which may cause a distal end of the lattice density adjusting implement to adjust the lattice material for altering the lattice density. In addition, movement of the lattice density adjusting implement 3102 may enable a user to adjust the lattice density of any desired portion of the occluding device. In some embodiments, the lattice density adjusting implement 3102 is not required to adjust the lattice density.

The occluding device may further be administered and positioned into a vessel via a delivery device. For example, a delivery device may include a tubular structure such as a catheter through which the occluding device may be placed into a vessel. The delivery device may further include the lattice density adjusting implement 3102 that may be used to adjust the lattice density of the occluding device. The lattice density adjusting implement 3102 may further adjust the lattice density only at one portion of the occluding device while not affecting other portions of the occluding device, if desired. Alternatively, the lattice density adjusting implement 3102 may be used to increase the lattice density at one portion of the occluding device while decreasing the lattice density at another portion of the occluding device. The lattice density adjusting implement 3102 may be controlled by pressure or motion forces applied via the delivery device.

In one example, the lattice density adjusting implement 3102 may be connected to a wire to a proximal end of the delivery device. The user may apply a force to the proximal end of the wire at the proximal end of the delivery device. The force applied which may be a pressure or motion force, for example, may cause corresponding movement of the lattice density adjusting implement 3102. The movement of the lattice density adjusting implement 3102 may further contact strands of the occluding device to move the strands. The movement of the strands of the occluding device may cause a change in the lattice density in at least one portion of the occluding device. Hence, user input may control a lattice density adjusting implement 3102 to cause varying lattice densities in selected portions of the occluding device.

In another example, the lattice density of the occluding device may be adjusted based on movement of the occluding device, or part of the device, in a blood vessel. For example, the occluding device may be placed and moved within a blood vessel. As the occluding device is moved in the blood vessel, the lattice density in selected portions of the occluding device may be adjusted accordingly. The lattice density in one portion of the occluding device may increase while the lattice density in another portion of the occluding device may increase, decrease or stay the same. In one example, the occluding device contacts a wall of the blood vessel and a force is applied to a proximal end of the occluding device. For example a user may apply a force to a proximal end of the occluding device. This force, which may be a pressure or motion force, for example, may be applied at a proximal end of a delivery device through which the occluding device may be positioned in a vessel and may be adjusted in the vessel. The applied force causes the strands or ribbons of the occluding device to adjust such that the lattice density in the occluding device varies based on the portion of the occluding device.

As one example, the occluding device contains intertwining ribbons forming a lattice structure with a lattice density. The occluding device is introduced to a site in a blood vessel of an aneurysm. The occluding device is further applied to the portion of the blood vessel at and around the aneurysm as illustrated in FIG. 7. The outer sides of the occluding device may be in contact with at least a portion of the blood vessel in areas surrounding the aneurysm, however, the outer side of the occluding device at the site of the aneurysm does not contact a wall of the blood vessel. This may be because the aneurysm is situated such that the wall of the aneurysm protrudes outward from the wall of the surround blood vessel such that the outer sides or surface of the occluding device does not directly contact the inner surface of the wall of the aneurysm.

Pressure may be applied to, for example, a proximal end of the occluding device. In this example, the lattice structure of the occluding device is freely adjustable such that the pressure may cause movement of the lattice structure of the occluding device in a distal direction. Frictional forces acting on the occluding device from the inner surface of the walls of the blood vessel in contact with the outer sides or surfaces of the occluding device may impede movement of the lattice structure in areas of the occluding device in contact with the wall of the blood vessel. However, gradual movement of the occluding device in the blood vessel can be accomplished by application of pressure or force at the proximal end of the occluding device.

In some embodiments, a portion of the occluding device overlying the neck of the aneurysm does not contact the walls of the blood vessel. Because this portion of the occluding device subject to less frictional forces as compared to the portion of the occluding device in direct contact with the inner wall of the blood vessel, the lattice structure of the occluding device overlying the aneurysm may change as the applied force causes the portion of the occluding device proximal to the aneurysm to move distally to cause an increase in force applied to the portion of the occluding device overlying the aneurysm. Also, the section of the occluding device overlying the blood vessel wall distal to the aneurysm may be subject to higher frictional forces than that applied to the portion of the occluding device overlying the aneurysm. As a result, in some embodiments, the lattice density of the occluding device overlying the aneurysm is increased. In some embodiments, the lattice density of the occluding device either does not increase or increases to a lesser degree than the portion of the occluding device overlying the aneurysm.

Figure 32:
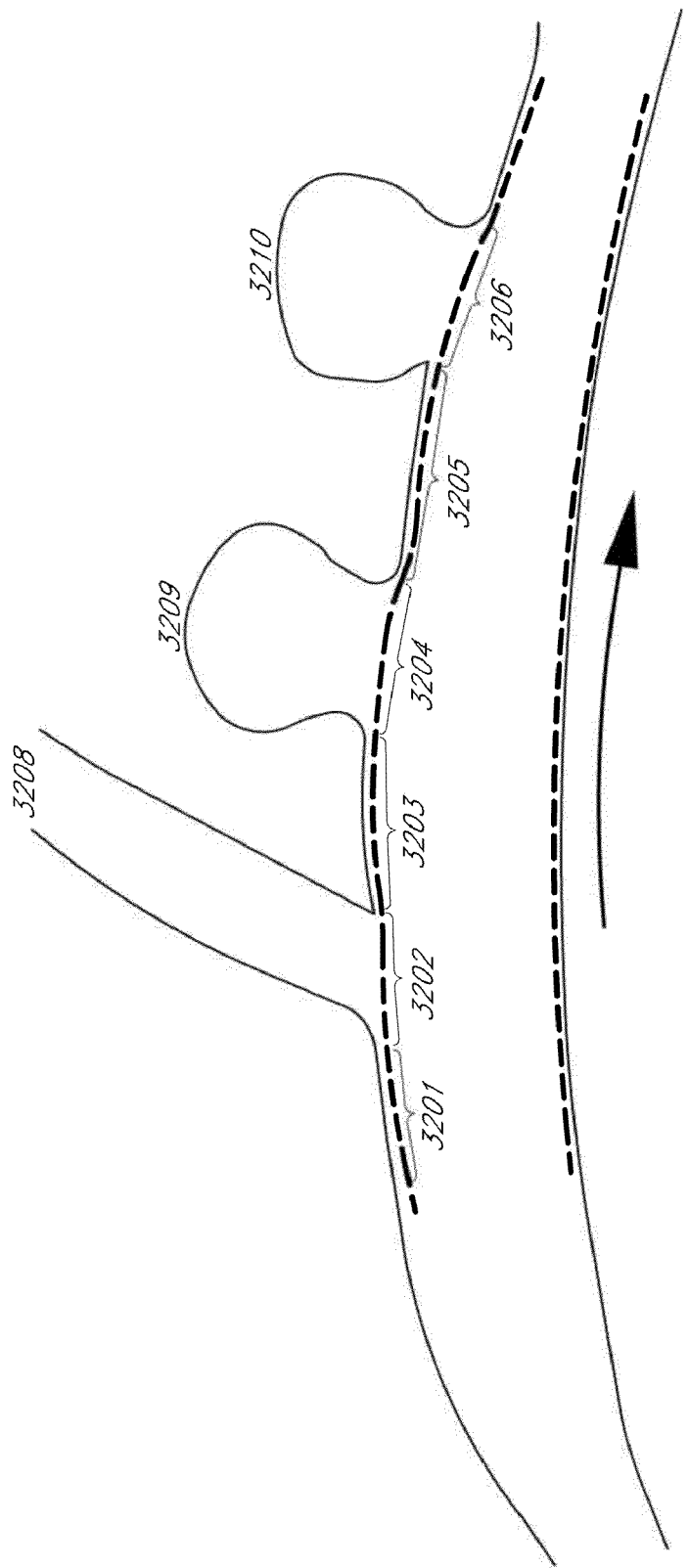
FIG. 32 shows an example of a deployed occluding device inside the lumen of a vessel spanning the neck of aneurysms, a bifurcation and branch vessels.

In another example, an aneurysm may be located at a branching of a blood vessel as illustrated in FIG. 32. The occluding device is placed such that a first portion 3201 of the occluding device may be located proximal to a blood vessel branch and aneurysms. A second portion 3202 of the occluding device may be located overlying the blood vessel branch 3208, a third portion of the occluding device may be located overlying a portion of the blood vessel distal to the blood vessel branch 3208 and proximal to a first aneurysm 3209, a fourth portion of the occluding device may be located overlying the first aneurysm 3209, a fifth portion of the occluding device may overlie the portion of the blood vessel distal to the first aneurysm 3209 and proximal to a second aneurysm 3210. A sixth portion of the occluding device may overlie the second aneurysm 3210. Blockage of blood flow to the aneurysms may be desired, however, blockage of blood flow to the branched blood vessel may not be desired.

In this example, a user may apply a pressure or force to a proximal end of an occluding device to cause a portion of the occluding device to advance in the blood vessel in a distal direction. The first portion 3201 of the occluding device (proximal to the blood vessel branch 3208 and the aneurysms 3209 and 3210) may transmit the force to more distal portions of the occluding device, including the second portion 3202 of the occluding device located over the blood vessel branch 3208. The frictional force impeding advancement of the occluding device in the second portion 3202 of the occluding device is low because the second portion 3202 of the occluding device does not contact the wall (or contacts it less than the first portion) of the blood vessel directly. Rather, the second portion 3202 of the occluding device overlies a blood vessel branch 3208 as illustrated in FIG. 32. Hence, the lattice density in the second portion 3202 of the occluding device increases as the first portion 3201 of the occluding device transfers the force to the second portion 3202 of the occluding device. Also a negative force applied to the occluding device may cause the lattice density in the second portion 3202 of the occluding device to decrease, thus permitting flow of blood into the blood vessel branch 3208.

The second portion 3202 of the occluding device also transfers the force to the third portion 3203 of the occluding device overlying the portion of blood vessel distal to the blood vessel branch 3208. However, the frictional forces acting on the third portion 3203 of the occluding device is higher than those frictional forces acting on the second portion 3202 because the third portion 3203 of the occluding device is in contact with the wall of the blood vessel. Hence, the lattice density of the occluding device in the third portion 3203 is initially lower than the lattice density of the occluding device in the second portion 3202.

The force applied to the third portion 3203 of the occluding device (overlying and in contact with the portion of the blood vessel distal to the blood vessel branch 3208 and first aneurysm 3209) is transferred to the fourth portion 3204 of the occluding device, which is the portion of the occluding device overlying the first aneurysm 3209. The frictional forces acting on the fourth portion 3204 of the occluding device is lower than the frictional forces acting on the third portion 3203 of the occluding device because the fourth portion 3204 of the occluding device is not in direct contact with the inner wall of the blood vessel. Hence, the pressure applied to the fourth portion 3204 of the occluding device causes the lattice density in the fourth portion 3204 of the occluding device to increase.

Also, the force applied to the fourth portion 3204 of the occluding device may be transferred to the fifth portion 3205 of the occluding device, which is in contact with the portion of the blood vessel between the first aneurysm 3209 and the second aneurysm 3210. The frictional force acting on the fifth portion 3205 of the occluding device is greater than the frictional force acting on the fourth portion 3204 of the occluding device because at least a portion of the fifth portion 3205 of the occluding device is in contact with the inner wall of the blood vessel. However, the fourth portion 3204 of the occluding device overlies the second aneurysm 3209 and is not in contact with the wall of the blood vessel. Hence, the difference in the frictional forces applied to the portions of the occluding device results in controlled changes in the lattice density of different portions of the occluding device in this example.

Also illustrated in FIG. 32 is the sixth portion 3206 of the occluding device that overlies the second aneurysm 3210. The frictional forces acting upon the sixth portion 3206 of the occluding device is less than the frictional force acting on the fifth portion of the occluding device 3205 because the sixth portion 3206 of the occluding device does not contact a wall of the blood vessel directly. Therefore, the force transferred from the fifth portion 3205 of the occluding device to the sixth portion 3206 of the occluding device may cause the lattice density of the sixth portion 3206 to increase. Hence, the lattice density of the fourth portion and the sixth portion of the occluding device may be increased by application of a pressure or motion force at the occluding device. Also, retraction of the occluding device such as by pulling a proximal end of the occluding device proximally may cause the lattice density of the second portion of the occluding device to decrease. This may cause increased flow of blood and/or fluids into the blood vessel branch 3208 while impeding flow of blood and/or fluids into the first or second aneurysms (3209, 3210).

FIG. 37 illustrates another embodiment of the occluding device 3700. The occluding device 3700 may be utilized to treat various forms of aneurysms. For example, the occluding device 3700 may be used to treat an aneurysm 3702 (as shown by aneurysm portions 3702a, 3702b and 3702c), which is a fusiform aneurysm. The occluding device 3700 may be deployed such that a distal portion 3710 of the occluding device 3700 arrives at a target site to treat the aneurysm 3702. The occluding device 3700 may be deployed using any number of methods. For example, a catheter can store the occluding device 3700 in a compressed configuration and advance occluding device 3700 to the target site, upon which the distal portion 3710 of the occluding device 3700 is deployed. As the occluding device 3700 is deployed from the catheter, the occluding device 3700 may expand into the expanded configuration. At the distal portion 3710, the occluding device 3700 makes contact with the vessel wall distal to the aneurysm 3702. The catheter may further be retracted to deploy the rest of the occluding device 3700, for example, allowing a middle portion 3714 (as shown by 3714a and 3714b) and a proximal portion 3712 (as shown by 3712a and 3712b) to expand. The middle portion 3714, because of a greater diameter of the occluding device 3700 may not expand all the way to make contact with the aneurysm walls 3716. The proximal portion 3712 of the occluding device 3700 may make contact with the vessel walls proximal to the aneurysm 3702 after expanding from the compressed configuration into the expanded configuration.

The porosity of middle portion 3714 may be adjusted to reduce the blood flow 3704 into the aneurysm 3702. For example, the porosity of the middle portion 3714 can be reduced by applying an axially compressive force to the proximal portion 3712 of the occluding device 3700 towards the direction of the distal portion 3710. The axially compressive force may be greater than the frictional force caused by the contact between the proximal portion 3712 and the vessel walls. The axially compressive force may continue to be applied until the porosity of the middle portion 3714 has been reduced appropriately to treat the aneurysm 3702. The porosity of the middle portion 3714 may be adjusted by applying either an axially compressive force to the proximal portion 3712 or an axially expansive force to the proximal portion 3712 (e.g., by pulling proximal portion 3712 against the direction of the blood flow 3704). A similar technique may be applied to the distal portion 3710 as well.

The porosity of middle portion 3714b, specifically, may be adjusted so that it is higher than the porosity of the middle portion 3714a in order to allow sufficient blood flow 3706 into branch vessel 3708 while at the same time reducing blood flow to the aneurysm portion 3702a. This can be achieved by applying a lower axially compressive force to the proximal portion 3712b relative to the proximal portion 3712a. Alternatively, the porosity of the middle portion 3714b can be adjusted alone by applying either an axially compressive force to the proximal portion 3712b or an axially expansive force to the proximal portion 3712b. For example, if the porosity of middle portion 3714b is too low to allow blood flow 3706 into branch vessel 3708, an axially expansive force may be applied to proximal portion 3712b (e.g., pulling on proximal portion 3712b). This may result in the middle portion 3714b expanding to increase the porosity of the middle portion 3714b, allowing more blood to flow into branch vessel 3708. Furthermore, the porosity of middle portion 3714b may be adjusted by using an adjusting implement (such as adjusting implement 3102 of FIG. 31), as described above.

The porosity of the middle portion 3714b may be adjusted such that substantial thrombosis may occur within aneurysm 3702 while at the same time allowing blood flow 3706 into branch vessel 3708. In some embodiments, the porosity of the middle portion 3714b may be adjusted such that endotheliazation may occur outlining the blood flow 3706 through the aneurysm 3702. For example, the porosity of the middle portion 3714b may be adjusted such that substantial thrombosis may occur within aneurysm 3702, particularly within aneurysm portions 3702a, 3702b and 3702c, while at the same time allowing an endothelium 3718 to develop around the aneurysm portions 3702b and 3702c, outlining the blood flow 3706. In some embodiments, the porosity of the middle portion 3714b to achieve this endotheliazation effect is between about 5% and 35%. In some embodiments, the porosity of the middle portion 3714b to achieve this endotheliazation effect is between about 35% and about 70%. In some embodiments, the porosity of the middle portion 3714b to achieve this endotheliazation effect is between about 70% and 80%. In some embodiments, the porosity of the middle portion 3714b to achieve this endotheliazation effect is less than or equal to about 5% or greater than about 80%.

This endotheliazation effect may be achieved depending on the foregoing factors or other factors. For example, in some embodiments, applying a delayed occlusion as described above may result in such an endotheliazation effect. In some embodiments, the wall thickness of middle portion 3714b as described above may result in such an endotheliazation effect. In some embodiments, the pore size of the pores of middle portion 3714b as described above may result in such an endotheliazation effect. In some embodiments, the width of the strands or the thickness of the strands of middle portion 3714b as described above may result in such an endotheliazation effect. In some embodiments, the shape of the strand as described above may result in such an endotheliazation effect. In some embodiments, the endotheliazation effect may be achieved based on any of the foregoing factors alone or in combination with any of the other factors.

Figure 16:
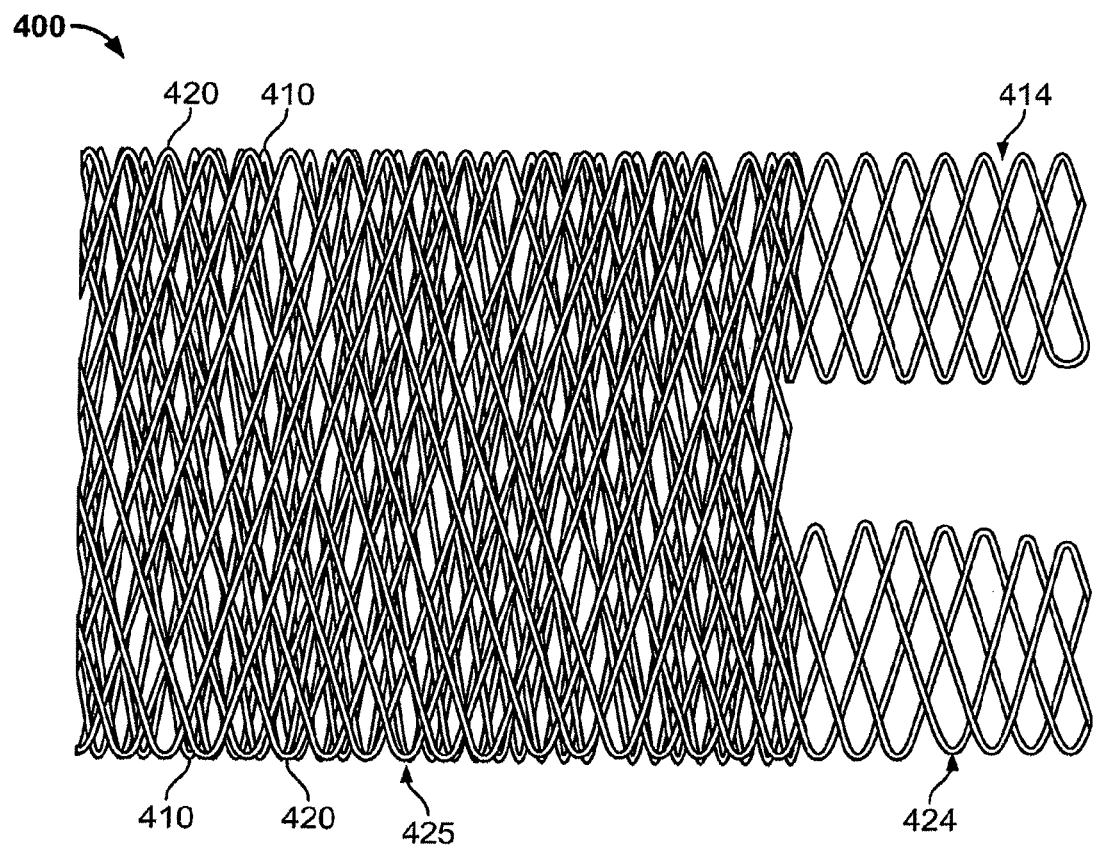
FIG. 16 illustrates a bifurcated occluding device according to embodiments of the disclosure in which two occluding devices of lesser densities are combined to form a single bifurcated device.

Any of the occluding devices disclosed herein can be used with a second occluding device to create a bifurcated occluding device 400 as shown in FIG. 16. This device could be created in vivo. In forming the occluding device 400, a portion of a first occluding device 410 having a low density can be combined with a portion of a second occluding device 410 that also has a low density. The occluding devices 410, 420 can be any of those discussed herein. After these portions of the two occluding devices 410, 420 are combined in an interwoven fashion to form an interwoven region 425, the remaining portions 414, 424 can branch off in different directions, thereby extending along two branches of the bifurcation. Areas outside of the interwoven region 425 can have greater lattice density for treating an aneurysm or lesser lattice density for allowing flow to branches 15, 16 of the vessel.

Figure 41:
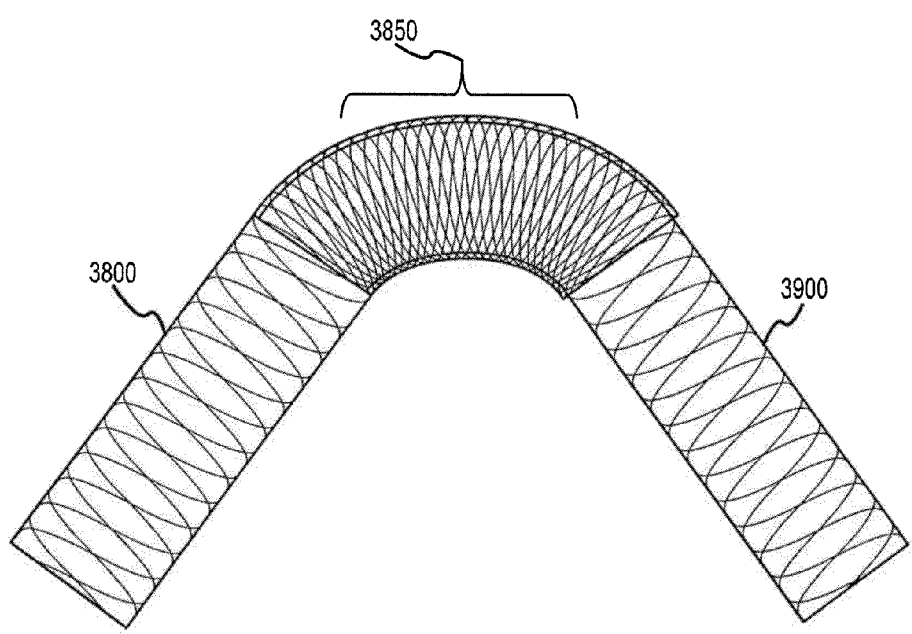
FIG. 41 illustrates an example of two occluding devices with an overlapping portion.

Additional and/or other embodiments of the occluding device are illustrated in FIGS. 38-42. Multiple occluding devices may be utilized wherein at least a portion of each of the occluding devices overlap with each other. Example occlusion devices, deployment devices, and deployment methods are described in U.S. Provisional Patent App. No. 60/574,429 and U.S. patent application Ser. Nos. 11/136,395, 11/136,398, 11/420,023, 11/420,025, and 11/420,027, each of which is incorporated by reference in its entirety. For example, FIG. 38 illustrates a first occluding device 3800. A second occluding device 3900 may be deployed within the first occluding device 3800. In some embodiments, the first occluding device 3800 and the second occluding device 3900 may be identical occluding devices. Thus, the porosity of the first occluding device 3800 and the second occluding device 3900 may be the same when both devices are unrestrained. The overlapping portion 3850 of the first occluding device 3800 and the second occluding device 3900 may provide a combined porosity that is less than the porosity of the same portion of the first occluding device 3800 or the second occluding device 3900 alone. The second occluding device 3800 may be deployed completely within the first occluding device 3900 or a portion of the occluding device 3800 may be deployed within the first occluding device 3800, as shown in FIGS. 39 and 41. Although two occluding devices are illustrated, more occluding devices may be used in combination with each other to provide various combined porosities that may be substantially lower than the porosity an individual occluding device may provide.

In some embodiments, the first occluding device 3800 may be deployed within a vessel 3806, as shown in FIG. 40 in a cross sectional view. For example, the first occluding device 3800 may be in a compressed configuration before deployment. Upon deploying the first occluding device 3800 within the vessel 3806, the first occluding device 3800 expands into the expanded configuration with a first diameter 3804, thus creating contact between the first occluding device 3800 and the walls of the vessel 3806. The second occluding device 3900 may similarly be deployed with at least a portion of the second occluding device 3900 within the first occluding device 3800. For example, the second occluding device 3900 may be in a compressed configuration before deployment. Upon deploying the second occluding device 3900 within the first occluding device 3800 (which is already in the expanded configuration), the second occluding device 3900 expands into the expanded configuration, thus creating contact between the second occluding device 3900 and either the inner wall 3802 of the first occluding device 3800, the walls of the vessel 3806, or both. This process may be repeated with more occluding devices to provide an appropriate combined porosity for aneurysm treatment or other types of treatments.

Figure 42:
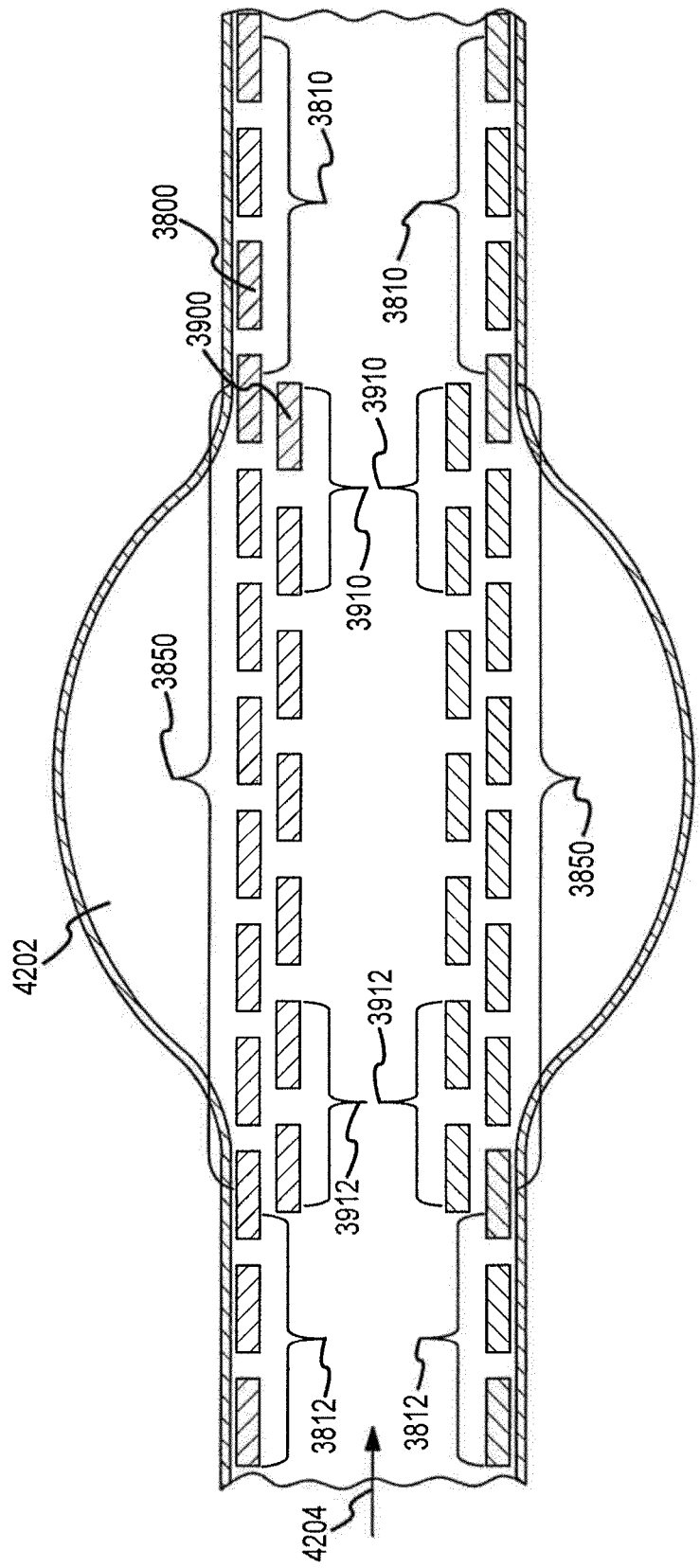
FIG. 42 illustrates embodiments of multiple occluding devices in treating an aneurysm.

Multiple occluding devices may be utilized to treat aneurysms as illustrated in FIG. 42. For example, the first occluding device 3800 may be deployed to treat the aneurysm 4202 using similar techniques as described above. The first occluding device 3800 comprises a distal portion 3810 and a proximal portion 3812, and extends such that the proximal portion 3812 is proximal to the aneurysm 4202 while the distal portion 3810 is distal to the aneurysm 4202. The second occluding device 3900 may be deployed within the first occluding device 3800. The second occluding device 3900 comprises a distal portion 3910 and a proximal portion 3912. The second occluding device 3900 may be positioned such that the second occluding device 3900 is substantially adjacent to the aneurysm 4202. For example, the proximal portion 3912 of the second occluding device 3900 is positioned distal to the proximal portion 3812 of the first occluding device 3800 and the distal portion 3910 of the second occluding device 3900 is positioned proximal to the distal portion 3810 of the first occluding device 3800.

The first occluding device 3800 and the second occluding device 3900 may have substantially the same porosity or different porosities when unrestrained. The overlapping portion 3850 may result in a combined porosity that is lower than the porosity of the first occluding device 3800 or the porosity of the second occluding device 3900, resulting in reduced blood flow 4204 into aneurysm 4202. The combined porosity may be adjusted in various ways, for example by individually adjusting the porosity of the first occluding device 3800, the second occluding device 3900, or by adding more occluding devices to decrease the combined porosity. At one extreme, the combined porosity may be adjusted to substantially 0%, or any other porosity resulting in little to no blood flow 4204 into aneurysm 4202, inducing substantial thrombosis within the aneurysm 4202 over time.

In one example, the porosity of the first occluding device 3800 may be adjusted before the second occluding device 3900 is deployed, using similar techniques as described above. Subsequently, the porosity of the second occluding device 3900 may be adjusted upon deployment of the second occluding device 3900. For example, the distal portion 3910 of the second occluding device 3900 may be in a compressed configuration and advanced to an area proximal to the distal portion 3810 of the first occluding device 3800. The distal portion 3910 of the second occluding device 3900 may be allowed to expand to make contact with the first occluding device 3800. The rest of the second occluding device 3900 may be deployed such that the porosity of the second occluding device 3900 is decreased by allowing more portions of the second occluding device 3900 to expand closer to the distal portion 3910 of the second occluding device 3900. Alternatively, the porosity of the second occluding device 3900 can be increased by allowing more portions of the second occluding device 3900 to expand farther from the distal portion 3910 of the second occluding device 3900. Thus, the combined porosity may be adjusted by first adjusting the porosity of the first occluding device 3800 and then adjusting the porosity of the second occluding device 3900 upon deployment.

In some embodiments, the combined porosity may be adjusted after both the first occluding device 3800 and the second occluding device 3900 have been deployed. For example, an axially compressive force may be applied to the proximal portion 3812 of the first occluding device 3800 towards the direction of the distal portion 3810. The axially compressive force may be greater than the frictional force caused by the contact between the proximal portion 3712 and the vessel walls. The axially compressive force may continue to be applied until the combined porosity of the overlapping portion 3850 has been reduced appropriately to treat the aneurysm 4202. In some embodiments, the second occluding device 3900 may expand and make contact with the first occluding device 3800 such that the axially compressive force applied to the first occluding device 3800 is less than or equal to the frictional force caused by the contact between the first occluding device 3800 and the second occluding device 3900. As a result, applying the axially compressive force to the first occluding device 3800 also causes the portion of the second occluding device 3900 in contact with first occluding device 3800 to compress, resulting in a combined reduced porosity. The combined porosity of the overlapping portion 3850 may be adjusted by applying either an axially compressive force to the proximal portion 3812 or an axially expansive force to the proximal portion 3812 (e.g., by pulling proximal portion 3812 against the direction of the blood flow 4204). A similar result can be achieved by applying the same technique to the proximal portion 3912 of the second occluding device 3900. Furthermore, similar techniques may also be applied to the distal portions 3810 and 3910 as well.

In some embodiments, the second occluding device 3900 may expand and make contact with the first occluding device 3800 such that the axially compressive force applied to the first occluding device 3800 is greater than the frictional force caused by the contact between the first occluding device 3800 and the second occluding device 3900. In such a case, the porosity of the first occluding device 3800 or the porosity of the second occluding device 3900 may be adjusted independent of each other. For example, the porosity of any portion of the first occluding device 3800 may be adjusted applying either an axially compressive force to the proximal portion 3812 or an axially expansive force to the proximal portion 3812. Similarly, the porosity of any portion of the second occluding device 3900 may be adjusted by applying either an axially compressive force to the proximal portion 3912 or an axially expansive force to the proximal portion 3912. By individually adjusting the porosity of the first occluding device 3800 or the second occluding device 3900, the combined porosity of the overlapping portion 3850 may also be adjusted. Furthermore, the porosity of the overlapping portion 3850 may be adjusted by using an adjusting implement (such as adjusting implement 3102 of FIG. 31) and applying an axially compressive or expansive force to the portions of the first occluding device 3800 or the second occluding device 3900.

The density of the lattice for each of the disclosed occluding devices can be about 20% to about 80% of the surface area of its occluding device. In an embodiment, the lattice density can be about 20% to about 50% of the surface area of its occluding device. In yet another embodiment, the lattice density can be about 20% to about 30% of the surface area of its occluding device.

In another example, the lattice density of an occluding device may be adjusted or altered by user input such as a user input motion. The input motion may be in a longitudinal orientation. For example, an input force or pressure may in a direction along a longitudinal axis of the occluding device may be received at a portion of the occluding device. The portion of the occluding device may have a lattice density prior to the application of the force, pressure or movement of the strands of the occluding device in the portion of the occluding device receiving the input force. The lattice density in the portion of the occluding device may change based on the received input. For example, the strands of the occluding device may move in a longitudinal direction in the occluding device. Also, the longitudinal movement of strands of the occluding device may occur at a portion of the occluding device or may occur at the entire occluding device. In the example of longitudinal movement of strands of the occluding device at a portion of the occluding device, the strands at the portion of the occluding device may move based on the received input such that the lattice density of the occluding device at the portion of the occluding device receiving the input may increase. Alternatively, the lattice in a portion of the occluding device may also decrease in response to the input force, pressure or motion. Also, based on the input force, pressure, or motion, the lattice density in a first portion of the occluding device may increase while the lattice density in a second portion of the occluding device may decrease or stay the same. Hence, different portions of the occluding device may have a different movement based on an input received at the occluding device such that one portion of the occluding device may have an increase or decrease in lattice density while any other portion of the occluding device may have a decrease or increase in the lattice density. Alternatively, the lattice density in any of the portions of the occluding device may stay the same.

A typical occluding device having sixteen strand braids with about 0.005 inch wide ribbon, 30 picks per inch (PPI) (number of crosses/points of contact per inch), and about 0.09 inch outer diameter has approximately 30% of lattice density (surface covered by the ribbon). In the embodiments disclosed herein, the ribbon can be about 0.001 inch thick with a width of between about 0.002 inch to about 0.005 inch. In an embodiment, the ribbon has a thickness of about 0.004 inch. For a 16-strands ribbon that is about 0.001 inch thick and about 0.004 inch wide, the coverage for 50 PPI, 40 PPI, and 30 PPI will have 40%, 32% and 24% approximate surface coverage, respectively. For a 16-strands ribbon that is about 0.001 inch thick and about 0.005 inch wide, the coverage for 50 PPI, 40 PPI, and 30 PPI will be about 50%, 40% and 30% approximate surface coverage, respectively.

In choosing a size for the ribbon, one may consider whether, when the ribbons are bundled up, they will slide through a delivery catheter. For example, sixteen strands of a 0.006 inch wide ribbon may not slide through a catheter having an internal diameter of about 0.027 inch or less as well as stents having a smaller contracted configuration.

While other strand geometry may be used, these other geometries, such as round, will limit the device due to their thickness dimension. For example, a round wire with about a 0.002 inch diameter may occupy up to about 0.008 inch in cross sectional space within the vessel. This space can impact and disrupt the blood flow through the vessel. The flow in the vessel can be disrupted with this change in diameter.

Delivering and Deploying an Occluding Device within a Vessel

Figure 43:
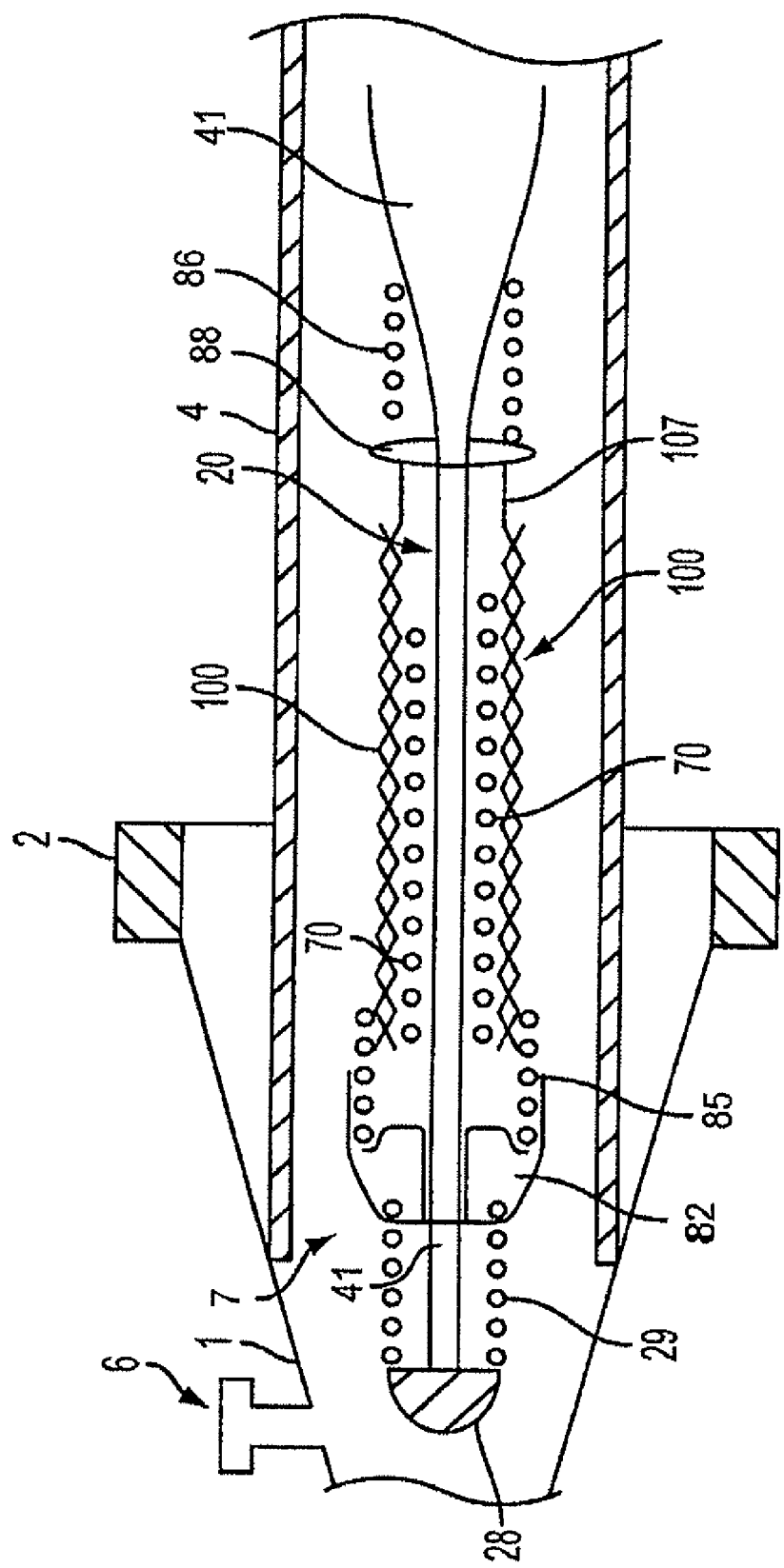
FIG. 43 is a cross section of an occluding device delivery assembly and occluding device according to an aspect of the disclosure.

An occluding device delivery assembly having portions with small cross section(s) and which is highly flexible is described herein. FIG. 43 illustrates an introducer sheath 4 according to an aspect of the disclosure that receives, contains and delivers an occluding device 100 to a flexible catheter 1 for positioning within the vasculature of an individual.

Figure 44:
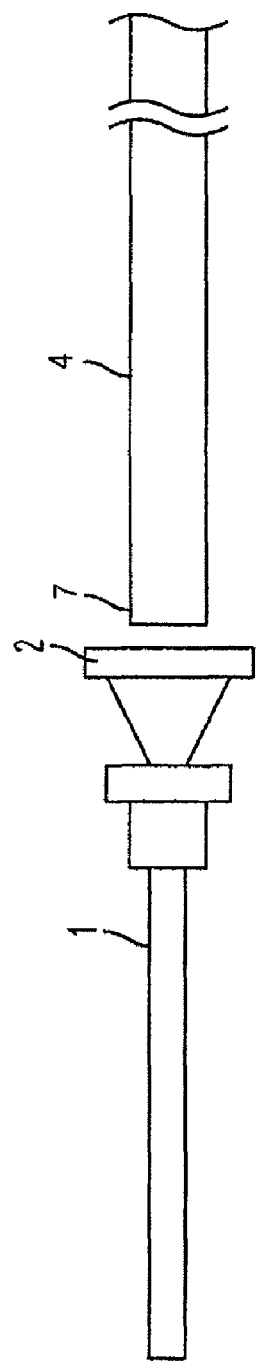
FIG. 44 illustrates a catheter and introducer sheath shown in FIG. 43.

A distal end 7 of the introducer sheath 4 is sized and configured to be received within a hub 2 of the catheter 1, as shown in FIGS. 43 and 44. The hub 2 can be positioned at the proximal end of the catheter 1 or at another location spaced along the length of the catheter 1. The catheter 1 can be any known catheter that can be introduced and advanced through the vasculature of a patient. In an embodiment, the catheter has an inner diameter of about 0.047 inch or less. In another embodiment, the catheter has an inner diameter of about 0.027 inch to about 0.021 inch. In an alternative embodiment, the catheter could have an inner diameter of about 0.025 inch. However, it is contemplated that the catheter 1 can have an inner diameter that is greater than about 0.047 inch or less than about 0.021 inch. After the introducer sheath 4 is positioned within the catheter hub 2, the occluding device 100 can be advanced from the introducer sheath 4 into the catheter 1 in preparation for deploying the occluding device 100 within the vasculature of the patient.

The catheter 1 may have at least one fluid introduction port 6 located adjacent the hub 2 or at another position along its length. The port 6 is preferably in fluid communication with the distal end of the catheter 1 so that a fluid, e.g., saline, may be passed through the catheter 1 prior to insertion into the vasculature for flushing out air or debris trapped within the catheter 1 and any instruments, such as guidewires, positioned within the catheter 1. The port 6 may also be used to deliver drugs or fluids within the vasculature as desired.

Figure 45:
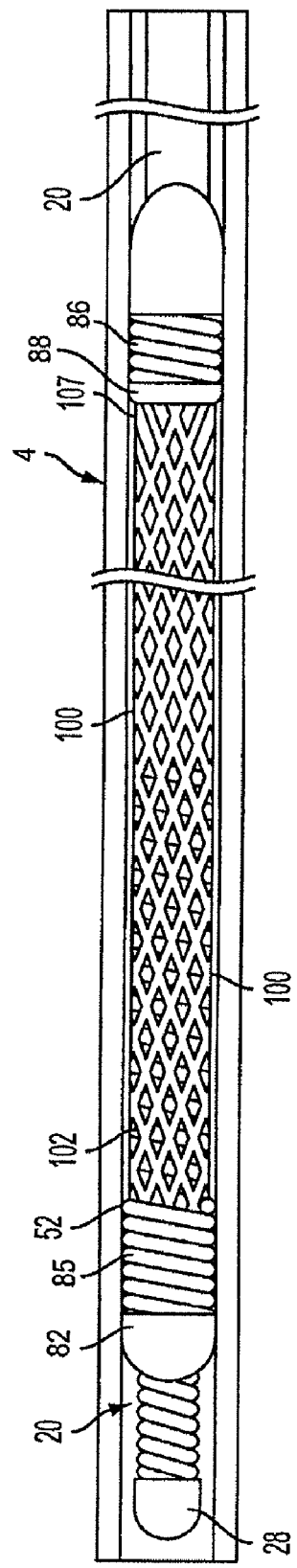
FIG. 45 is a partial cut away view of the introducer sheath of FIG. 44 carrying a guidewire assembly loaded with an occluding device.

FIG. 45 illustrates the introducer sheath 4, an elongated flexible delivery guidewire assembly 20 that is movable within the introducer sheath 4 and the occluding device 100. As shown, the guidewire assembly 20 and the occluding device 100, carried by the guidewire assembly 20, have not been introduced into the catheter 1. Instead, as illustrated, they are positioned within the introducer sheath 4. The introducer sheath 4 may be made from various thermoplastics, e.g., PTFE, FEP, HDPE, PEEK, etc., which may optionally be lined on the inner surface of the sheath or an adjacent surface with a hydrophilic material such as PVP or some other plastic coating. Additionally, either surface may be coated with various combinations of different materials, depending upon the desired results.

The introducer sheath 4 may include drainage ports or purge holes (not shown) formed into the wall near the area covering the occluding device 100. There may be a single hole or multiple holes, e.g., three holes, formed into introducer sheath 4. These purge holes allow for fluids, e.g., saline, to readily escape from in between the introducer sheath 4 and the guidewire assembly 20 when purging the sheath prior to positioning the introducer sheath 4 in contact with the catheter hub 2, e.g., to remove trapped air or debris.

Figure 46:
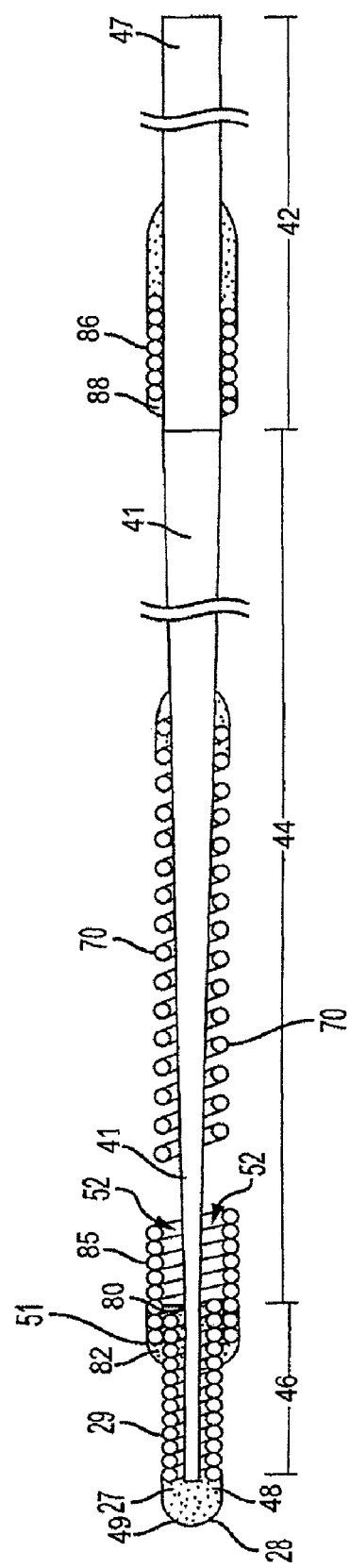
FIG. 46 is a cross section of the guidewire assembly illustrated in FIG. 45.

As shown in FIG. 46, the guidewire assembly 20 includes an elongated flexible guidewire 41. The flexibility of the guidewire 41 allows the guidewire assembly 20 to bend and conform to the curvature of the vasculature as needed for positional movement of the occluding device 100 within the vasculature. The guidewire 41 may be made of a conventional guidewire material and have a solid cross section. Alternatively, the guidewire 41 can be formed from a hypotube. In either embodiment, the guidewire 41 has a diameter D5 ranging from about 0.010 inch to about 0.020 inch. In an embodiment, the largest diameter of the guidewire 41 is about 0.016 inch. The material used for the guidewire 41 can be any of the known guidewire materials including superelastic metals, e.g., Nitinol. Alternatively, the guidewire 41 can be formed of metals such as stainless steel. Length L4 of the guidewire can be from about 125 to about 190 cm. In an embodiment, the length L4 is about 175 cm.

The guidewire assembly 20 can have the same degree of flexion along its entire length. In an alternative embodiment, the guidewire assembly 20 can have longitudinal sections, each with differing degrees of flexion/stiffness. The different degrees of flexions for the guidewire assembly 20 can be created using different materials and/or thicknesses within different longitudinal sections of the guidewire 41. In another embodiment, the flexion of the guidewire 41 can be controlled by spaced cuts (not shown) formed within the delivery guidewire 41. These cuts can be longitudinally and/or circumferentially spaced from each other. The cuts can be formed with precision within the delivery guidewire 41. Different sections of the delivery guidewire 41 can include cuts formed with different spacing and different depths to provide these distinct sections with different amounts of flexion and stiffness. In any of the above embodiments, the guidewire assembly 20 and the guidewire 41 are responsive to torque applied to the guidewire assembly 20 by the operator. As discussed below, the torque applied to the guidewire assembly 20 via the guidewire 41 can be used to release the occluding device 100 from the guidewire assembly 20.

The size and shape of the cuts formed within the delivery guidewire 41 may be controlled so as to provide greater or lesser amounts of flexibility. Because the cuts can be varied in width without changing the depth or overall shape of the cut, the flexibility of the delivery guidewire 41 may be selectively altered without affecting the torsional strength of the delivery guidewire 41. Thus, the flexibility and torsional strength of the delivery guidewire 41 may be selectively and independently altered.

Advantageously, longitudinally adjacent pairs of cuts may be rotated about 90 degrees around the circumference of the delivery guidewire 41 from one another to provide flexure laterally and vertically. However, the cuts may be located at predetermined locations to provide preferential flexure in one or more desired directions. Of course, the cuts could be randomly formed to allow bending (flexion) equally, non-preferentially in all directions or planes. In one embodiment, this could be achieved by circumferentially spacing the cuts.

The flexible delivery guidewire 41 can include any number of sections having the same or differing degrees of flexion. For example, the flexible delivery guidewire 41 could include two or more sections. In the embodiment illustrated in FIG. 46, the flexible delivery guidewire 41 includes three sections, each having a different diameter. Each section can have a diameter of about 0.003 inch to about 0.025 inch. In an embodiment, the diameter of one or more sections can be about 0.010 inch to about 0.020 inch. A first section 42 includes a proximal end 47 that is located opposite the position of the occluding device 100. The first section 42 can have a constant thickness along its length. Alternatively, the first section 42 can have a thickness (diameter) that tapers along its entire length or only a portion of its length. In the tapered embodiment, the thickness (diameter) of the first section 42 decreases in the direction of a second, transition section 44. For those embodiments in which the guidewire 41 has a circular cross section, the thickness is the diameter of the section.

The second, transition section 44 extends between the first section 42 and a third, distal section 46. The second section 44 tapers in thickness from the large diameter of the first section 42 to the smaller diameter of the third section 46. As with the first section 42, the second section 44 can taper along its entire length or only a portion of its length.

The third section 46 has a smaller thickness compared to the other sections 42, 44 of the delivery guidewire 41. The third section 46 extends away from the tapered second section 44 that carries the occluding device 100. The third section 46 can taper along its entire length from the second section 44 to the distal end 27 of the delivery guidewire 41. Alternatively, the third section 46 can have a constant diameter or taper along only a portion of its length. In such an embodiment, the tapering portion of the third section 46 can extend from the second section 44 or a point spaced from the second section 44 to a point spaced from distal end 27 of the delivery guidewire 41. Although three sections of the delivery guidewire 41 are discussed and illustrated, the delivery guidewire 41 can include more than three sections. Additionally, each of these sections can taper in their thickness (diameter) along all or only a portion of their length. In any of the disclosed embodiments, the delivery guidewire 41 can be formed of a shape memory alloy such as Nitinol.

Figure 47:
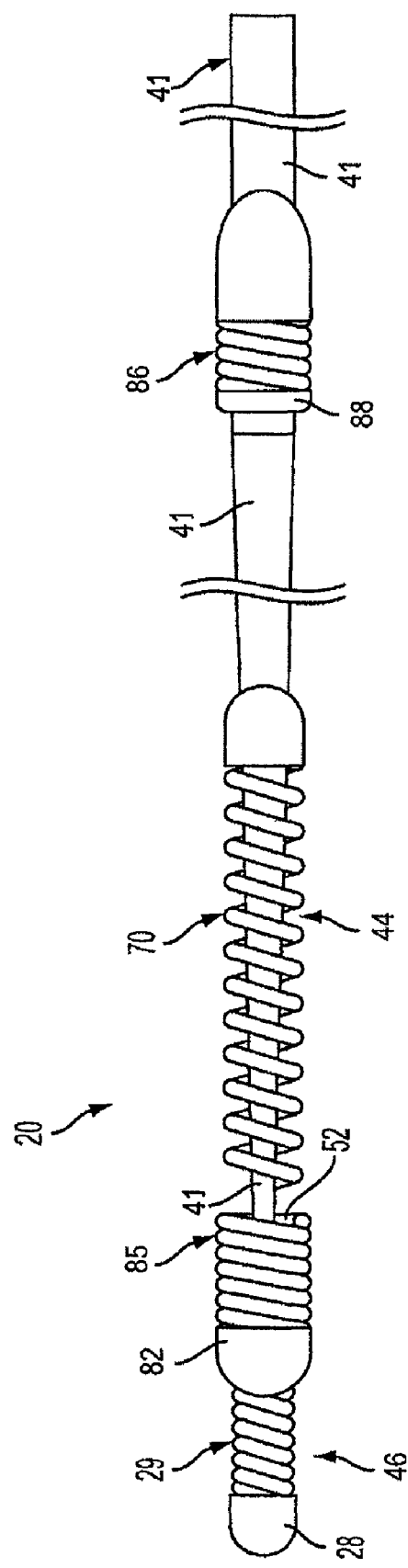
FIG. 47 is a schematic view of the guidewire assembly of FIG. 46.
Figure 48:
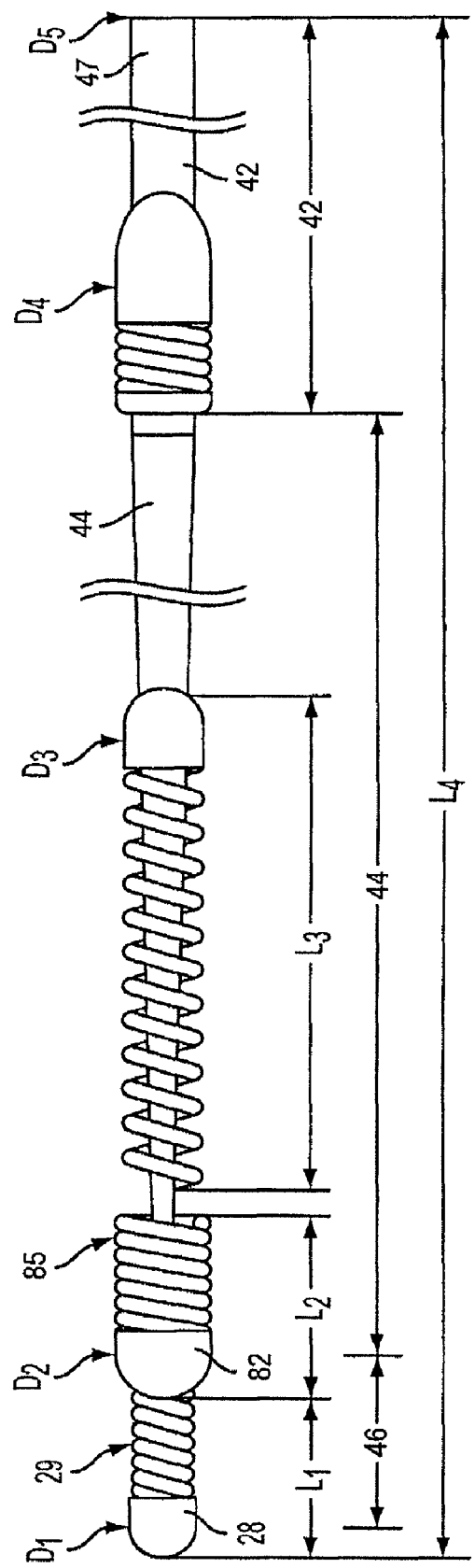
FIG. 48 is a second schematic view of the guidewire assembly of FIG. 46.

A tip 28 and flexible tip coil 29 are secured to the distal end 27 of the delivery guidewire 41 as shown in FIGS. 46 and 47. The tip 28 can include a continuous end cap or cover as shown in the figures, which securely receives a distal end of the tip coil 29. Flexion control is provided to the distal end portion of the delivery guidewire 41 by the tip coil 29. However, in an embodiment, the tip 28 can be free of the coil 29. The tip 28 has a non-percutaneous, atraumatic end face. In the illustrated embodiment, the tip 28 has a rounded face. In alternative embodiments, the tip 28 can have other non-percutaneous shapes that will not injure the vessel in which it is introduced. As illustrated in FIG. 46, the tip 28 includes a housing 49 that securely receives the distal end of the guidewire 41 within an opening 48 in the interior surface of the housing 49. The guidewire 41 can be secured within the opening by any known means.

As shown in FIG. 46, the tip coil 29 surrounds a portion of the guidewire 41.

The tip coil 29 is flexible so that it will conform to and follow the path of a vessel within the patient as the tip 28 is advanced along the vessel and the guidewire 41 bends to follow the tortuous path of the vasculature. The tip coil 29 extends rearward from the tip 28 in the direction of the proximal end 47, as shown.

The tip 28 and coil 29 have an outer diameter D1 of about 0.010 inch to about 0.018 inch. In an embodiment, their outer diameter D1 is about 0.014 inch. The tip 28 and coil 29 also have a length L1 of about 0.1 cm to about 3.0 cm. In an embodiment, they have a total length L1 of about 1.5 cm.

A proximal end 80 of the tip coil 29 is received within a housing 82 at a distal end 44 of a protective coil 85, as shown in FIGS. 43 and 46. The housing 82 and protective coil 85 have an outer diameter D2 of about 0.018 inch to about 0.038 inch. In an embodiment, their outer diameter D2 is about 0.024 inch. The housing 82 and protective coil 85 have a length L2 of about 0.05 cm to about 0.2 cm. In an embodiment, their total length L2 is about 0.15 cm.

The housing 82 has a non-percutaneous, atraumatic shape. For example, as shown in FIG. 47, the housing 82 has a substantially blunt profile. Also, the housing 82 can be sized to open/support the vessel as it passes through it. Additionally, the housing 82 can include angled sidewalls sized to just be spaced just off the inner surface of the introducer sheath 4.

The housing 82 and protective coil 85 form a distal retaining member that maintains the position of the occluding device 100 on the flexible guidewire assembly 20 and helps to hold the occluding device 100 in a compressed state prior to its delivery and deployment within a vessel of the vasculature. The protective coil 85 extends from the housing 82 in the direction of the proximal end 47 of the delivery guidewire 41, as shown in FIG. 46. The protective coil 85 is secured to the housing 82 in any known manner. In a first embodiment, the protective coil 85 can be secured to the outer surface of the housing 82. In an alternative embodiment, the protective coil 85 can be secured within an opening of the housing 82 so that the housing 82 surrounds and internally receives the distal end 51 of the protective coil 85 (FIG. 46). As shown in FIGS. 45 and 46, the distal end 102 of the occluding device 100 is retained within the proximal end 52 so that the occluding device 100 cannot deploy while positioned in the sheath 4 or the catheter 1.

At the proximal end of the occluding device 100, a bumper coil 86 and cap 88 prevent or limit lateral movement of the occluding device 100 along the length of the guidewire 41 in the direction of the proximal end 47, see FIG. 45. The bumper coil 86 and cap 88 have an outer diameter D4 of about 0.018 inch to about 0.038 inch. In an embodiment, their outer diameter D4 is about 0.024 inch. The cap 88 contacts the proximal end 107 of the occluding device 100 and prevents or limits it from moving along the length of the guidewire 41 away from the protective coil 85. The bumper coil 86 can be in the form of a spring that contacts and pressures the cap 88 in the direction of the protective coil 85, thereby creating a biasing force against the occluding device 100. This biasing force (pressure) aids in maintaining the secured, covered relationship between the distal end 102 of the occluding device 100 and the protective coil 85. As with any of the coils positioned along the delivery guidewire 41, the bumper coil 86 can be secured to the delivery guidewire 41 by soldering, welding, RF welding, glue, and/or other known adhesives.

Figure 52:
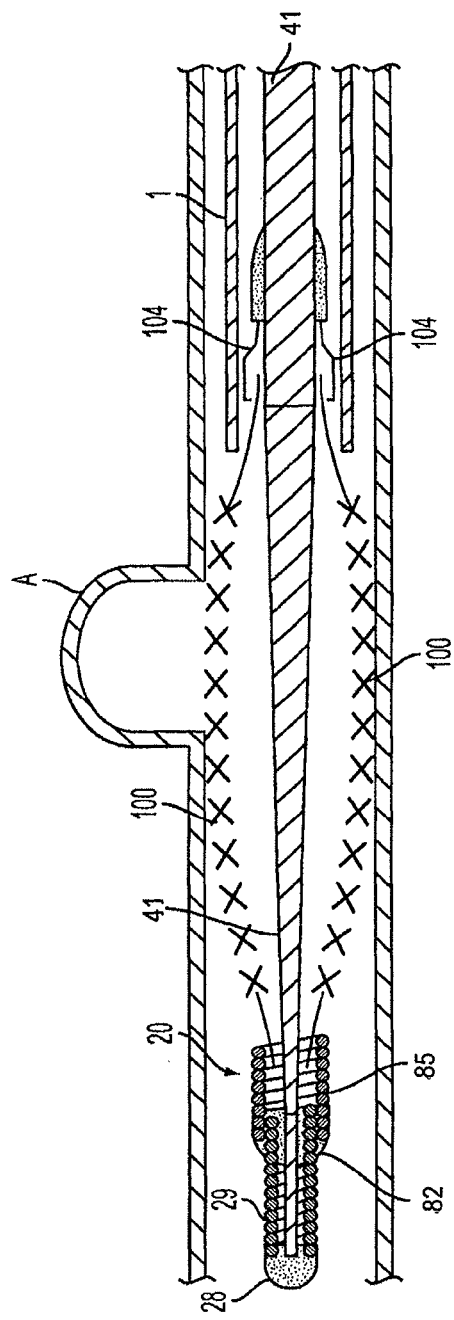
FIG. 52 is a schematic view of a guidewire assembly according to another embodiment of the disclosure.
Figure 53:
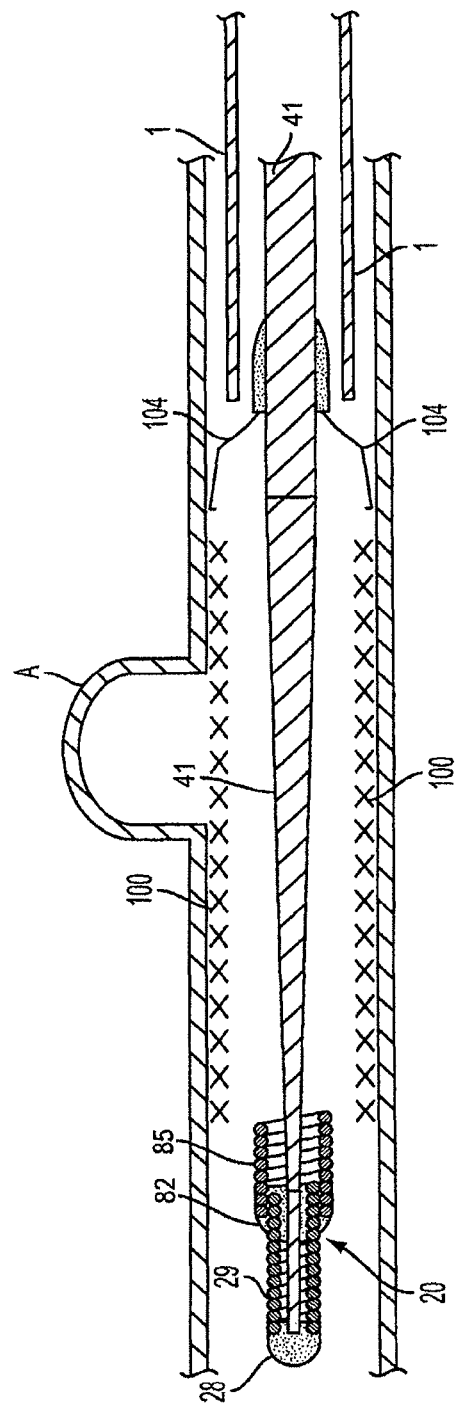
FIG. 53 is a schematic view of the deployed occluding device after having been deployed by the guidewire assembly of FIG. 52.

In an alternative embodiment illustrated in FIG. 52, the bumper coil 86 is not utilized. Instead, a proximal end 107 of the occluding device 100 is held in position by a set of spring loaded arms (jaws) 104 while positioned within the introducer sheath 4 or the catheter 1. The inner surfaces of the catheter 1 and the introducer sheath 4 limit the radial expansion of the arms 104. When the proximal end of the occluding device passes out of the catheter 1, the arms 104 would spring open and release the occluding device as shown in FIG. 53.

In another example, the occluding device 100 in the introducer sheath 4 or the catheter 1 may expand within a vessel under pressure. FIG. 54 illustrates an example of an expanded occluding device 100 that expands responsive to pressure. Pressure may be applied through the catheter 1 or the introducer sheath 4 as the occluding device 100 passes out of the catheter 1. The pressure may be exerted through application of air, fluid, or any material for increasing the internal pressure of the occluding device. The increase in pressure within the occluding device 100 when the occluding device 100 passes out of the catheter 1 may cause the occluding device to expand within the vessel. Conversely, a negative pressure may be exerted at the occluding device 100. FIG. 55 illustrates the occluding device 100 of FIG. 54 after a negative pressure is applied to the occluding device 100. The negative pressure may be applied via the catheter 1 or the introducer sheath 4 and may cause the occluding device 100 to retract or decrease in size. In one example, a negative pressure is exerted at the occluding device 100 after the occluding device 100 is passed out of the catheter 1 and expanded in the vessel. The negative pressure causes the occluding device 100 to retract. Upon retraction, the occluding device 100 may be reduced in size. In another example, the occluding device 100 may be replaced back into the catheter 1 after retraction. The negative pressure may be applied in a variety of ways. For example, the negative pressure may be applied by suction of air from the catheter 1 or by removal or suction of fluid from the catheter 1.

Also, in another example, the occluding device 100 may be expanded, for example, by application of increased pressure within the occluding device. The increased pressure may be administered via the delivery device by, for example, injecting air or fluid via the delivery device to the occluding device 100. The occluding device 100 may thus be expanded in a vessel such that the occluding device 100 may come into contact with the internal aspect of the wall of the vessel. In this way, at least a portion of the occluding device 100, while in the expanded state, may contact the wall of the vessel.

While in the expanded state, the occluding device 100 may be repositioned within the vessel. FIG. 60 illustrates an example of an expanded occluding device 100. FIG. 61 illustrates the example of FIG. 60 after the occluding device is repositioned within a blood vessel. In this example, the occluding device 100 may be expanded in a longitudinal axis along the vessel such that the occluding device 100 may move within the vessel while expanded. Pressure may be exerted by a user at a proximal end of the occluding device 100 such that the proximal end is moved distally within the vessel lumen. At the same time, frictional forces between the wall of the vessel and the more distal portions of the occluding device may prevent or limit immediate movement of the more distal portions of the occluding device. When the pressure or force exerted at the proximal end exceeds a threshold level, the force may be transmitted to the more distal portions of the occluding device to cause the more distal portions of the occluding device to more distally in the lumen of the vessel. In this way, the occluding device may move distally in the vessel lumen and may be repositioned at a desired location within the vessel by the user. FIG. 61 illustrates distal repositioning of the occluding device in a blood vessel.

Similarly, the occluding device may be repositioned more proximally in the vessel lumen by the user. For example, the user may provide a force or pressure at a distal portion of the occluding device in a proximal direction. The distal portion of the occluding device may move proximally while frictional forces between the more proximal portions of the occluding device prevent or limit initial movement of the more proximal portions of the occluding device. Hence, in this example, the occluding device compresses at a portion intermediate between the distal portion and the more proximal portions of the occluding device. When the pressure or force exerted by the user at the distal portion of the occluding device exceeds a threshold level that exceeds the frictional force preventing or limiting movement of the more proximal portions of the occluding device, the more proximal portions of the occluding device may move in a proximal direction responsive to the applied pressure or force. In this way, the occluding device may be repositioned proximally in the vessel.

Figure 62:
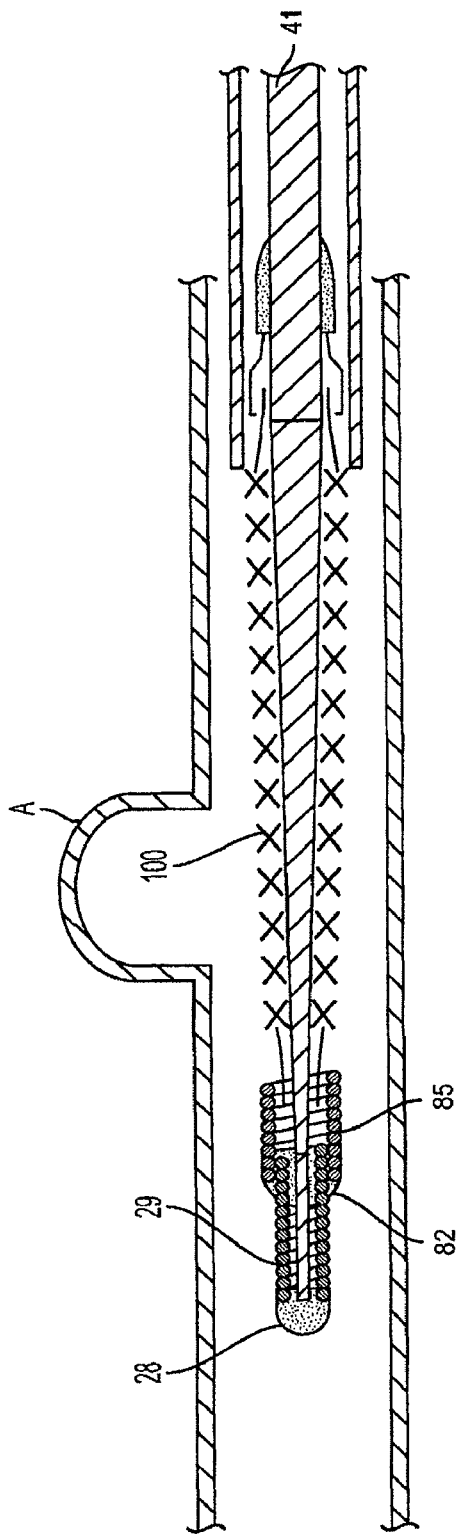
FIG. 62 illustrates an example of the occluding device in a retracted state.
Figure 63:
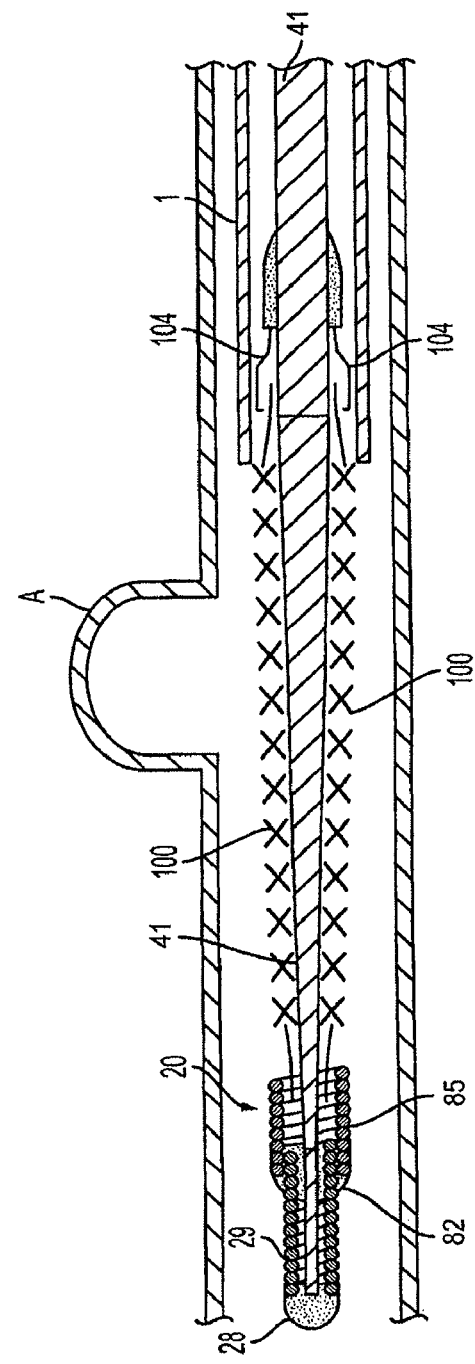
FIG. 63 illustrates an example of repositioning the occluding device while the occluding device is retracted.

In another example, the occluding device 100 may be repositioned in a blood vessel while the occluding device 100 is in a retracted state. FIG. 62 illustrates an example of the occluding device 100 in a retracted state. For example, negative pressure may be exerted at the occluding device 100 of FIG. 54 to cause the occluding device 100 to decrease in size as illustrated in FIG. 62. The occluding device 100 as illustrated in FIG. 62 is retracted and approximates the delivery device. FIG. 63 illustrates an example of repositioning the occluding device 100 while the occluding device is retracted. As FIG. 63 illustrates, the occluding device is moved in a distal direction. Similarly, the occluding device may also be repositioned in a proximal direction (not shown).

Also, deployment of the occluding device may be performed in parts. For example, the occluding device 100 may have a distal end and a proximal end. Deployment of the occluding device may include release of a distal end followed by release of the proximal end of the occluding device. Alternatively, deployment of the occluding device may include release of the proximal end followed by release of the distal end. Also, deployment of the occluding device may include release of the proximal end and the distal end of the occluding device 100 at approximately the same time.

Figure 56:
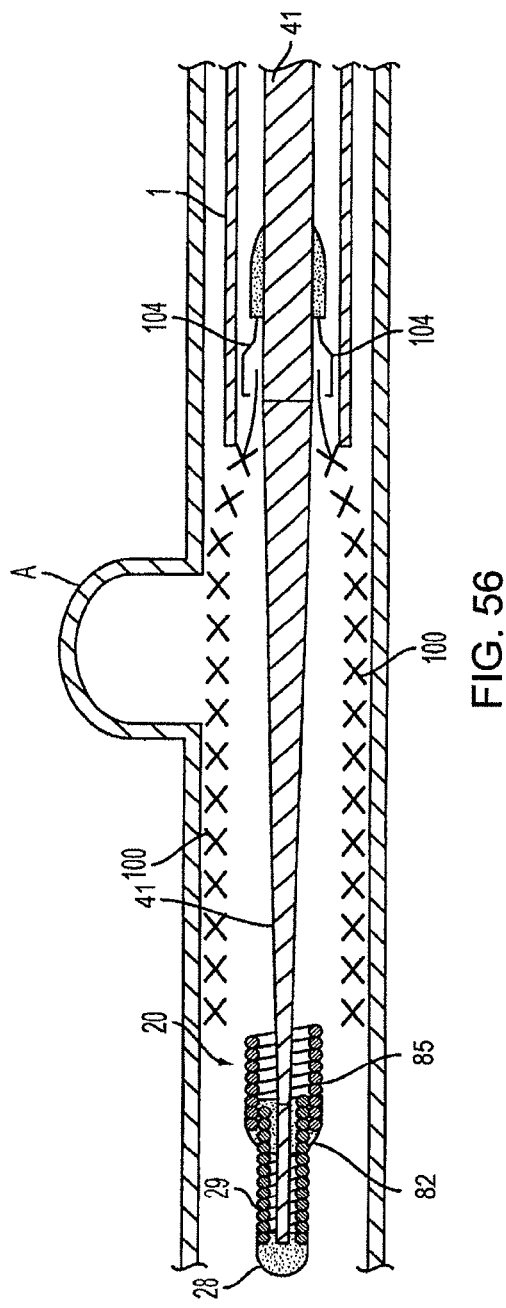
FIG. 56 illustrates an example of release of the distal end of the occluding device while the proximal end of the occluding device remains attached to the delivery device.

FIG. 56 illustrates an example of release of the distal end of the occluding device 100 while the proximal end of the occluding device remains attached to the delivery device. As FIG. 56 shows, the distal end of the occluding device 100 is deployed and abuts the wall of the blood vessel. The proximal end of the occluding device 100 is still attached to the delivery device. Release of the proximal end of the occluding device may be accomplished in a variety of ways as described herein.

Figure 57:
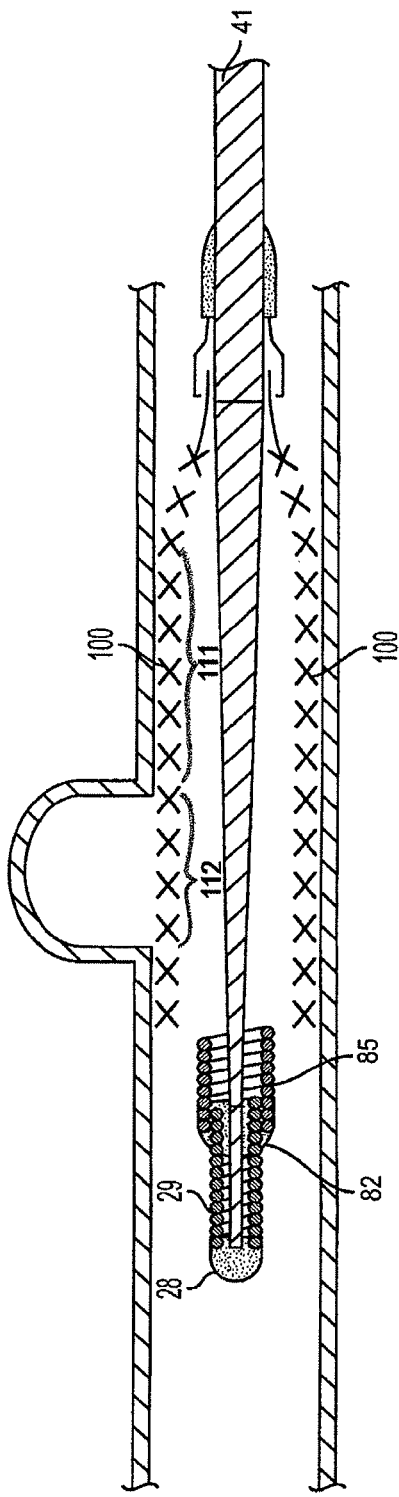
FIG. 57 illustrates an example of a partially deployed occluding device.

In addition, the partially deployed occluding device 100 as illustrated in FIG. 56 may be repositioned in the blood vessel. FIG. 57 illustrates an example of a partially deployed occluding device 100 in which the distal end of the occluding device 100 has been released from the delivery device while the proximal end of the occluding device 100 remains attached and non-deployed to the delivery device. In addition, FIG. 57 demonstrates repositioning of the occluding device while partially deployed. As FIG. 57 shows, the delivery device and occluding device 100 has been moved proximally in the blood vessel. Also, FIG. 57 illustrates that the occluding device is partially deployed in the blood vessel such that the distal end of the occluding device is released from the delivery device while the proximal end of the occluding device 100 remains attached to the delivery device.

As shown in FIGS. 56 and 57, the proximal end of the occluding device 100 remains in a compressed configuration while the rest of the occluding device 100 is in the expanded configuration. In addition to repositioning the occluding device 100, the porosity of any portion of the occluding device 100 may be decreased by applying an axially compressive force to the occluding device 100, for example by advancing the proximal end of the occluding device 100 towards the distal end of the occluding device 100 such that the middle portions of the occluding device 100 are axially compressed. In one example, an axially compressive force may be applied to the proximal end of the occluding device 100 where the axially compressive force is greater than a frictional force between the contact of a first portion 111 of the occluding device 100 and the vessel wall. The axially compressive force may continue to be applied such that a second portion 112 of the occluding device 100 is axially compressed, resulting in a decrease in porosity. Note that the second portion 112 is substantially adjacent to the aneurysm A, which presents less frictional force between the contact of the second portion 112 of the occluding device 100 and the surrounding vessel wall.

Additionally, the porosity of any portion of the occluding device 100 may be increased by applying an axially expansive force to the occluding device 100, for example by withdrawing the proximal end of the occluding device 100 away from the distal end of the occluding device 100 such that the middle portions of the occluding device 100 are axially expanded. For example, an axially expansive force may be applied to the proximal end of the occluding device 100 where the axially expansive force is greater than a frictional force between the contact of the first portion 111 of the occluding device 100 and the vessel wall. The axially expansive force may continue to be applied such that the second portion 112 of the occluding device 100 is axially expanded, resulting in an increase in porosity. Thus, the porosity of the second portion 112 of the occluding device 100 may be increased by withdrawing the proximal end of the occluding device 100 away from the distal end of the occluding device 100. The porosity of any portion of the occluding device 100 may be adjusted similarly by advancing or withdrawing the occluding device 100.

The occluding device 100 may also be retracted or removed from the vessel by withdrawing the proximal end of the occluding device 100, which remains attached to the delivery device, into the catheter 1. By continually withdrawing the proximal end of the occluding device 100 into the catheter 1, any expanded portions of the occluding device 100 may be drawn into the catheter 1 and compressed such that the occluding device 100 may fit within the catheter 1.

Figure 58:
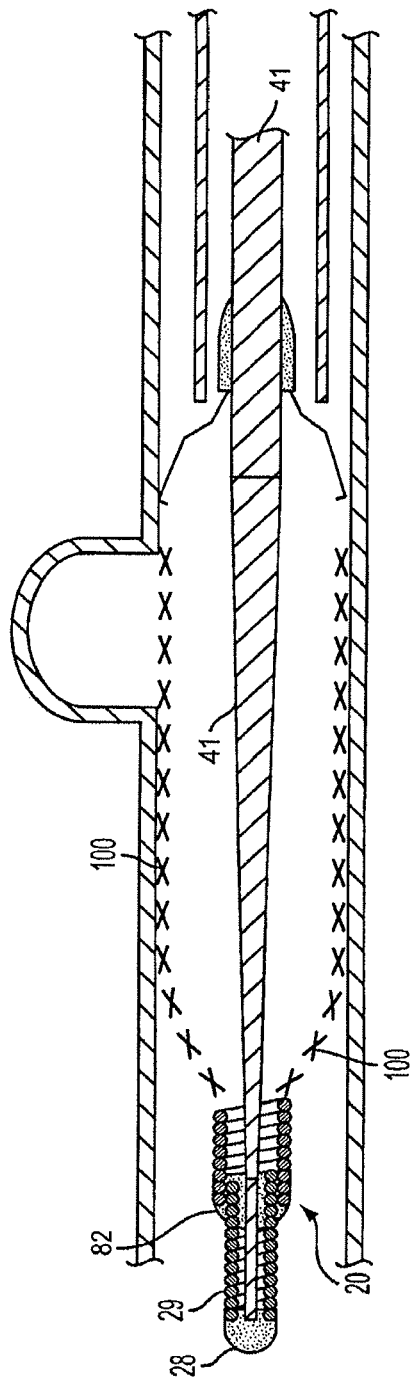
FIG. 58 illustrates another example of a partially deployed occluding device.

Alternatively, the proximal end of the occluding device may be released from the delivery device while the distal end of the occluding device remains attached to the delivery device. The distal end of the occluding device may then be deployed or released from the delivery device at a subsequent time. FIG. 58 illustrates an example of a partially deployed occluding device 100 in a blood vessel in which the proximal end of the occluding device 100 is released from the delivery device while the distal end of the occluding device remains attached to the delivery device. The proximal end of the occluding device 100 thus approximates the walls of the blood vessel.

Figure 59:
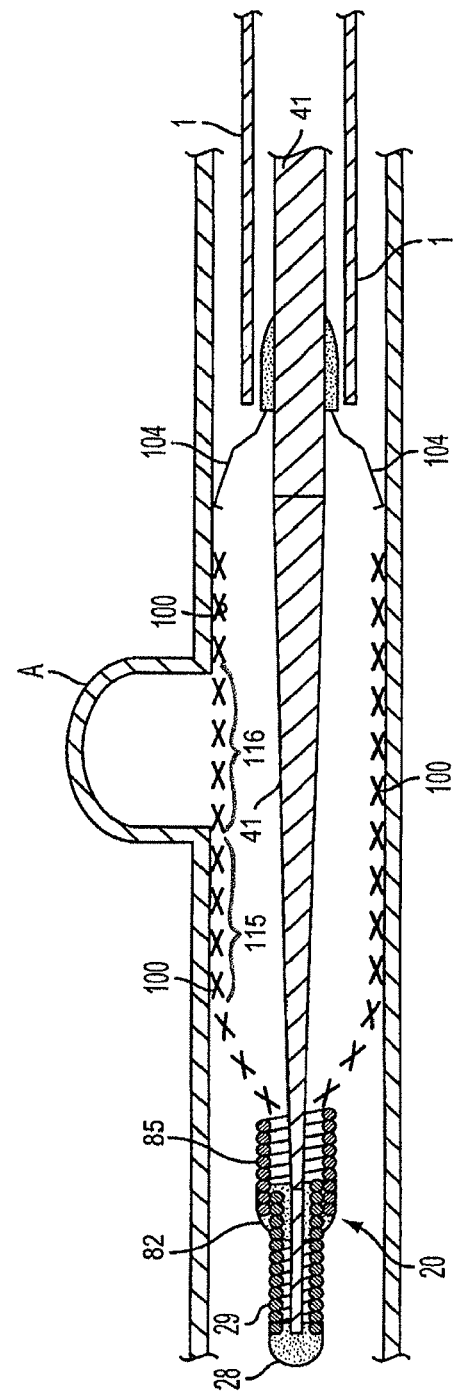
FIG. 59 illustrates the example of FIG. 58 in which the occluding device is repositioned proximally in the blood vessel.

FIG. 59 illustrates the example of FIG. 58 in which the occluding device 100 is repositioned proximally in the blood vessel. In this example, the occluding device is partially deployed such that the proximal end of the occluding device 100 is released from the delivery device while the distal end of the occluding device 100 is attached. The occluding device is then moved or repositioned to a more proximal location within the blood vessel. Alternatively, the occluding device may also be moved or repositioned to a more distal location within the blood vessel (not shown).

As shown in FIGS. 58 and 59, the distal end of the occluding device 100 remains in a compressed configuration while the rest of the occluding device 100 is in the expanded configuration. In addition to repositioning the occluding device 100, the porosity of any portion of the occluding device 100 may be decreased by applying an axially compressive force to the occluding device 100, for example by withdrawing the distal end of the occluding device 100 towards the proximal end of the occluding device 100 such that the middle portions of the occluding device 100 are axially compressed. In one example, an axially compressive force may be applied to the distal end of the occluding device 100 where the axially compressive force is greater than a frictional force between the contact of a first portion 115 of the occluding device 100 and the vessel wall. The axially compressive force may continue to be applied such that a second portion 116 of the occluding device 100 is axially compressed, resulting in a decrease in porosity. Note that the second portion 116 is substantially adjacent to the aneurysm A, which presents less frictional force between the contact of the second portion 116 of the occluding device 100 and the surrounding vessel wall.

Additionally, the porosity of any portion of the occluding device 100 may be increased by applying an axially expansive force to the occluding device 100, for example by advancing the distal end of the occluding device 100 away from the proximal end of the occluding device 100 such that the middle portions of the occluding device 100 are axially expanded. For example, an axially expansive force may be applied to the distal end of the occluding device 100 where the axially expansive force is greater than a frictional force between the contact of the first portion 115 of the occluding device 100 and the vessel wall. The axially expansive force may continue to be applied such that the second portion 116 of the occluding device 100 is axially expanded, resulting in an increase in porosity. Thus, the porosity of the second portion 116 of the occluding device 100 may be increased by advancing the distal end of the occluding device 100 away from the proximal end of the occluding device 100. The porosity of any portion of the occluding device 100 may be adjusted similarly by advancing or withdrawing the occluding device 100 relative to the proximal end of the occluding device 100.

In an alternative embodiment, the bumper coil 86 and cap 88 can be eliminated and the proximal end of the occluding device 100 can be held in position relative to the protective coil 85 by a tapered section of the guidewire 41. In such an embodiment, the enlarged cross section of this tapered section can be used to retain the occluding device 100 in position along the length of the delivery guidewire 41 and prevent or limit movement of the occluding device 100 in the direction of the proximal end 47.

As shown in FIG. 46, the guidewire assembly 20 includes a support 70 for the occluding device 100. In a first embodiment, the support 70 can include an outer surface of the delivery guidewire 41 that is sized to contact the inner surface of the occluding device 100 when the occluding device 100 is loaded on the guidewire assembly 20. In this embodiment, the outer surface of the delivery guidewire 41 supports the occluding device 100 and maintains it in a ready to deploy state. In another embodiment, illustrated in the Figures, the support 70 comprises a mid-coil 70 that extends from a location proximate the protective coil 85 rearward toward the bumper coil 86. The mid-coil 70 extends under the occluding device 100 and over the delivery guidewire 41, as shown in FIG. 43. The mid-coil 70 can be coextensive with one or more sections of the delivery guidewire 41. For example, the mid-coil 70 could be coextensive with only the second section 44 of the delivery guidewire 41 or it could extend along portions of both the third section 46 and the second section 44 of the delivery guidewire 41.

The mid-coil 70 provides the guidewire assembly 20 with an outwardly extending surface that is sized to contact the inner surface of the occluding device 100 in order to assist in supporting the occluding device and maintaining the occluding device 100 in a ready to deploy state. Like the other coils discussed herein and illustrated in the figures, the coiled form of the mid-coil 70 permits the mid-coil 70 to flex with the delivery guidewire 41 as the delivery guidewire 41 is advanced through the vasculature of the patient. The mid-coil 70 provides a constant diameter along a length of the delivery guidewire 41 that is covered by the occluding device 100 regardless of the taper of the delivery guidewire 41 beneath the occluding device 100. The mid-coil 70 permits the delivery guidewire 41 to be tapered so it can achieve the needed flexibility to follow the path of the vasculature without compromising the support provided to the occluding device 100. The mid-coil 70 provides the occluding device 100 with constant support regardless of the taper of the delivery guidewire 41 prior to the occluding device 100 being deployed. The smallest diameter of the occluding device 100 in its compressed state is also controlled by the size of the mid-coil 70. Additionally, the diameter of the mid-coil 70 can be chosen so that the proper spacing, including no spacing, is established between the occluding device 100 and the inner wall of the catheter 1 prior to deployment of the occluding device 100. The mid-coil 70 can also be used to bias the occluding device 100 away from the delivery guidewire 41 during its deployment.

In either embodiment, the support 70 can have an outer diameter D3 of about 0.010 inch to about 0.018 inch. In an embodiment, the outer diameter D3 is about 0.014 inch. The support 70 can also have a length L3 of about 2.0 cm to about 30 cm. In an embodiment, the length L3 of the support 70 is about 7 cm.

The occluding device 100 may also be placed on the mid-coil 70 between an optional pair of radio-opaque marker bands located along the length of the guidewire assembly 20. Alternatively, the protective coil 85, bumper coil 86 and or mid-coil 70 can include radio-opaque markers. In an alternative embodiment, the guidewire assembly 20 may include only a single radio-opaque marker. The use of radio-opaque markers allows for the visualization of the guidewire assembly 20 and the occluding device 100 during placement within the vasculature. Such visualization techniques may include conventional methods such as fluoroscopy, radiography, ultra-sonography, magnetic resonance imaging, etc.

The occluding device 100 can be delivered and deployed at the site of an aneurysm according to the following method and variations thereof. The delivery of the occluding device 100 includes introducing the catheter 1 into the vasculature until it reaches a site that requires treatment. The catheter 1 is introduced into the vasculature using a conventional technique such as being advanced over or simultaneously with a conventional vascular guidewire (not shown). The positioning of the catheter 1 can occur before it receives the guidewire assembly 20 or while it contains the guidewire assembly 20. The position of the catheter 1 within the vasculature can be determined by identifying radio-opaque markers positioned on or in the catheter 1.

After the catheter 1 is positioned at the desired location, the guidewire is removed and the distal end of the introducer sheath 4 is inserted into the proximal end of the catheter 1, as shown in FIG. 43. In an embodiment, the distal end of the introducer sheath 4 is introduced through the hub 2 at the proximal end of the catheter 1. The introducer sheath 4 is advanced within the catheter 1 until a distal tip of the introducer sheath 4 is wedged within the catheter 1. At this position, the introducer sheath 4 cannot be advanced further within the catheter 1. The introducer sheath 4 is then securely held while the delivery guidewire assembly 20 carrying the occluding device 100 is advanced through the introducer sheath 4 until the occluding device 100 is advanced out of the introducer sheath 4 and into the catheter 1.

The guidewire assembly 20 and the occluding device 100 are advanced through the catheter 1 until the tip coil 29 is proximate the distal end of the catheter 1. At this point, the position of the catheter 1 and guidewire assembly 20 can be confirmed. The guidewire assembly 20 is then advanced out of the catheter 1 and into the vasculature of the patient so that the proximal end 107 of the occluding device 100 is positioned outside the distal end of the catheter 1 and adjacent the area to be treated. At any point during these steps, the position of the occluding device 100 can be checked to determine that it will be deployed correctly and at the desired location. This can be accomplished by using the radio-opaque markers discussed above.

Figure 49:
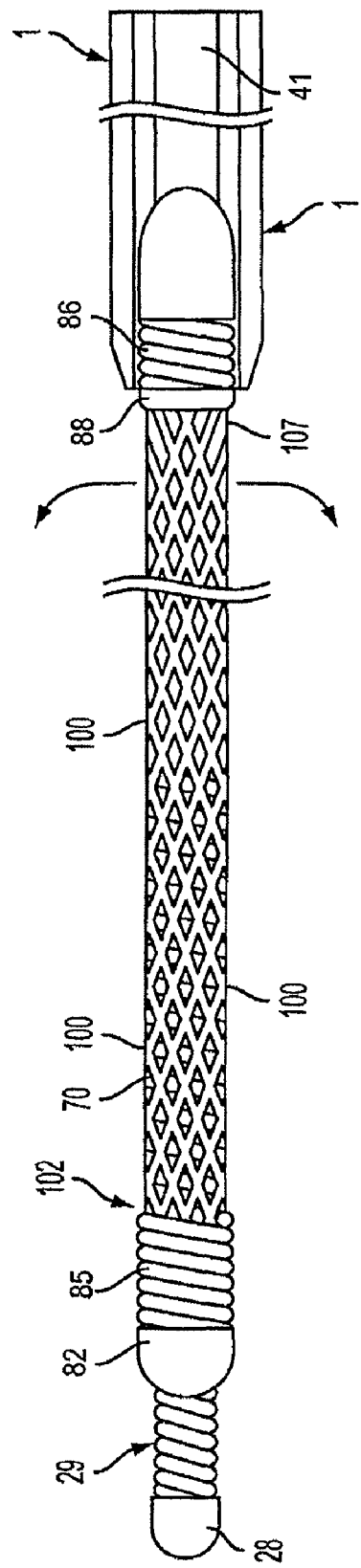
FIG. 49 illustrates the occluding device and a portion of the guidewire assembly positioned outside the catheter, and how a proximal end of the occluding device begins to deploy within a vessel.
Figure 50:
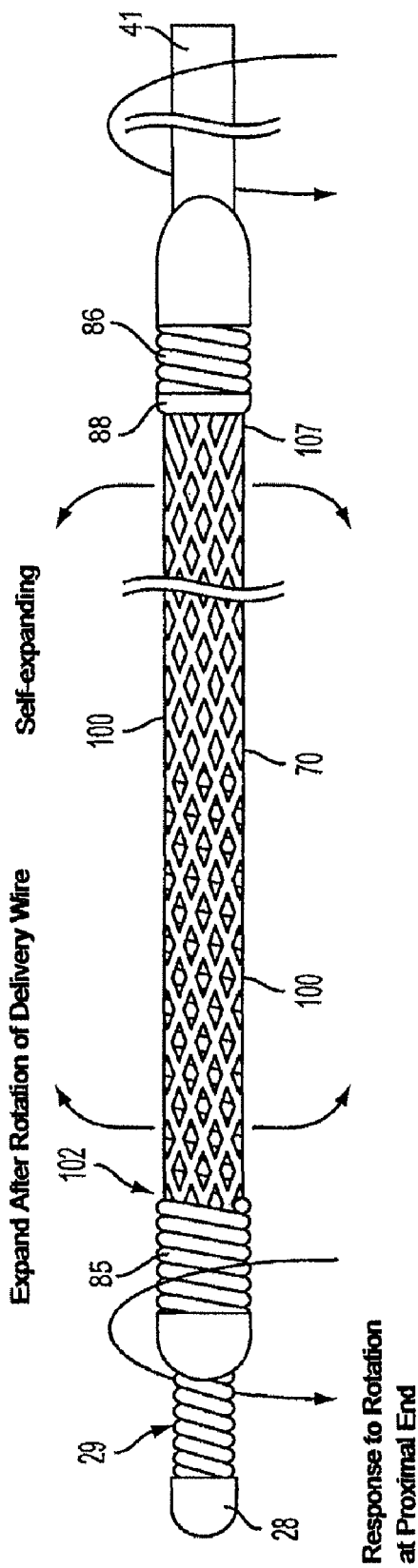
FIG. 50 illustrates a step in the method of deploying the occluding device.

When the distal end 102 of the occluding device 100 is positioned outside the catheter 1, the proximal end 107 will begin to expand, in the direction of the arrows shown in FIG. 49, within the vasculature while the distal end 102 remains covered by the protective coil 85. When the occluding device 100 is in the proper position, the delivery guidewire 41 is rotated (See FIG. 50) until the distal end 102 of the occluding device 100 moves away from the protective coil 85 and expands within the vasculature at the desired location. The delivery guidewire 41 can be rotated either clockwise or counter clockwise as needed to deploy the occluding device 100. In an embodiment, the delivery guidewire 41 may be rotated, for example, between about two and ten turns in either or both directions. In another example, the occluding device may be deployed by rotating the delivery guidewire 41 clockwise for less than about five turns, for example, three to five turns. After the occluding device 100 has been deployed, the delivery guidewire 41 can be retracted into the catheter 100 and removed from the body.

In one alternative or additional deployment method, the distal end 102 of the occluding device 100 may be passed outside of the catheter 1. The occluding device 100 may be further advanced so that the proximal end 107 of the occluding device 100 passes outside of the catheter. However, in this example, the proximal end 107 of the occluding device 100 expands responsive to the application of pressure to the inner surfaces of the occluding device 100. The applied pressure may be from any source. Examples of pressure exerted in the occluding device 100 include, but are not limited to, infusion of fluid or air into the lumen of the occluding device.

The increase in pressure in the occluding device may cause the occluding device 100 to expand. Expansion of the occluding device 100 may cause a disconnection of the proximal end 107 of the occluding device 100 and/or the distal end 102 of the occluding device 100 such that the occluding device may substantially fill the lumen of the vessel. Alternatively, the increase in pressure in the occluding device may expand the occluding device 100 without detachment of either the proximal end 107 or the distal end 102 of the occluding device 100. In this example, the occluding device 100 may be expanded without detaching the occluding device 100 from the delivery system. The expanded occluding device 100 may be adjusted and moved within the vessel in the expanded state while connected to the delivery system. When the occluding device 100 is at a desired location in the vessel, the occluding device 100 may be released from the delivery system. Release of the occluding device 100 from the delivery system may be accomplished in a variety of ways as described herein.

In addition, the coverage of the occluding device 100 may be adjusted while the occluding device is expanded and connected to the delivery system. For example, the occluding device 100 may be unsheathed from the catheter 1 and expanded under pressure (e.g., from fluid or air) such that the occluding device 100 is expanded in the vessel. The position of the occluding device 100 may be further adjusted. Also, the pressure applied within the occluding device 100 may be adjusted to increase the size of the expanded occluding device 100 in the vessel. Relative adjustments of the size of the expanded occluding device 100 (i.e., by adjusting the amount of pressure applied to the occluding device 100) and of the position or location of the occluding device 100 permit control of coverage of the occluding device when placed in the vessel.

Also, a negative pressure may be applied (e.g., air suction or removal of fluid from within the occluding device 100) to cause the occluding device to retract. The retracted occluding device 100 may further be placed back into the catheter 1. In one example, the occluding device 100 may be expanded and retracted as desired for movement or placement of the occluding device 100 within the vessel.

Figure 51:
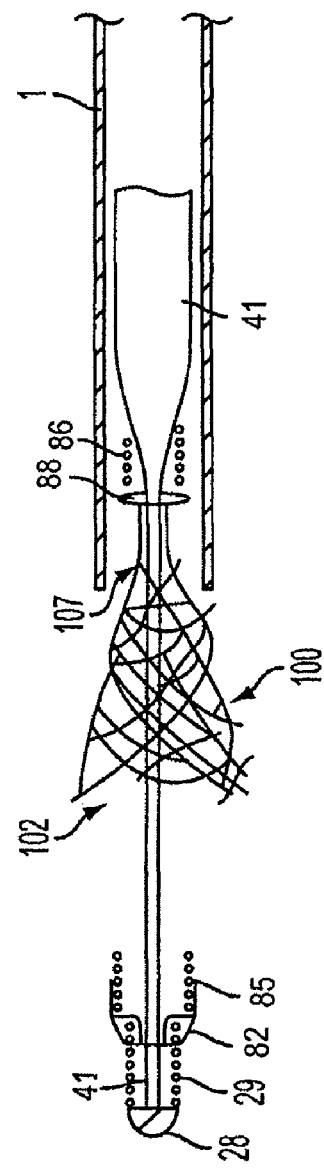
FIG. 51 illustrates the deployment of the occluding device according to an aspect of the disclosure.

In an alternative or additional deployment step shown in FIG. 51, friction between the occluding device 100 and inner surface of the catheter 1 cause the distal end of the occluding device 100 to separate from the protective coil 85. The friction can be created by the opening of the occluding device 100 and/or the mid-coil 70 biasing the occluding device 100 toward the inner surface of the catheter 1. The friction between the catheter 1 and the occluding device 100 will assist in the deployment of the occluding device 100. In those instances when the occluding device 100 does not open and separate from the protective coil 85 during deployment, the friction between occluding device 100 and the inner surface of the catheter 1 will cause the occluding device 100 to move away from the protective coil 85 as the delivery guidewire 41 and the catheter 1 move relative to each other. The delivery guidewire 41 can then be rotated and the occluding device 100 deployed within the vessel.

After the occluding device 100 radially self-expands into gentle, but secure, contact with the walls of the vessel so as to occlude the neck of the aneurysm A, the catheter 1 may be removed entirely from the body of the patient. Alternatively, the catheter 1 may be left in position within vasculature to allow for the insertion of additional tools or the application of drugs near the treatment site.

Known materials can be used in the subject technology. One common material that can be used with the occluding device 100 and the guidewire 41 is Nitinol, a nickel-titanium shape memory alloy, which can be formed and annealed, deformed at a low temperature, and recalled to its original shape with heating, such as when deployed at body temperature in the body. The radio-opaque markers can be formed of radio-opaque materials including metals, such as platinum, or doped plastics including bismuth or tungsten to aid in visualization.

Treatment of Lumens in the Body

Systems and methods for treating lumens within the body of a patient are provided below. Although the description may be presented in the context of one or more embodiments, it is understood that such systems and methods can be used in various lumens of the body and in various ways that would be appreciated by one of ordinary skill in the art. For example, systems and methods for treating atherosclerosis in a blood vessel and providing embolic protection during treatment are described according to embodiments of the disclosure.

Atherosclerosis is characterized by plaque buildup in a blood vessel (e.g., carotid artery). The plaque may be made up of cholesterol, cells and other fatty substances. Over time, the plaque can restrict or block blood flow through the affected blood vessel. If left untreated, a portion of the plaque can break off as plaque debris that travels downstream through the blood vessel to smaller blood vessels. The plaque debris can block blood flow to the smaller blood vessels resulting in death of tissue receiving blood from the smaller blood vessels. For example, blockage of vessels supplying blood to the heart or brain can result in heart attack or stroke.

Numerous minimally invasive procedures have been developed to treat atherosclerosis in a blood vessel. In one procedure, a catheter with an inflatable balloon is advanced through the blood vessel to an occlusion site in the blood vessel caused by plaque buildup. The balloon is then inflated to compress the plaque against the inner wall of the blood vessel, thereby opening up the occluded blood vessel. In another procedure, a catheter with a cutting tool is advanced through the blood vessel to the occlusion site. The cutting tool is then used to cut away the plaque to open up the occluded blood vessel. The catheter may include an aspirator located near the cutting tool to remove plaque debris caused by cutting away the plaque. After the blood vessel is opened, a stent or other device can be deployed in the blood vessel at the treatment site to strengthen the wall of the blood vessel and prevent or reduce the likelihood of reclosure.

During treatment of atherosclerosis, plaque debris can be released into the blood stream and cause embolization. Embolization occurs when the released plaque debris travel downstream from the treatment site and block blood flow to smaller blood vessels. Embolization can result in heart attack, stroke or other ailment depending on the tissue being fed blood by the blocked blood vessels.

To prevent or limit embolization during treatment of atherosclerosis, in some embodiments, a stent is at least partially deployed in the blood vessel downstream from the treatment site. The partially deployed stent acts as a filter that captures plaque debris released during treatment, preventing or limiting the plaque debris from traveling downstream to smaller blood vessels. In some embodiments, after treatment, the stent is fully deployed in the blood vessel, including the treatment site, to strengthen the wall of the blood vessel and prevent or reduce the likelihood of reclosure.

Figure 64:
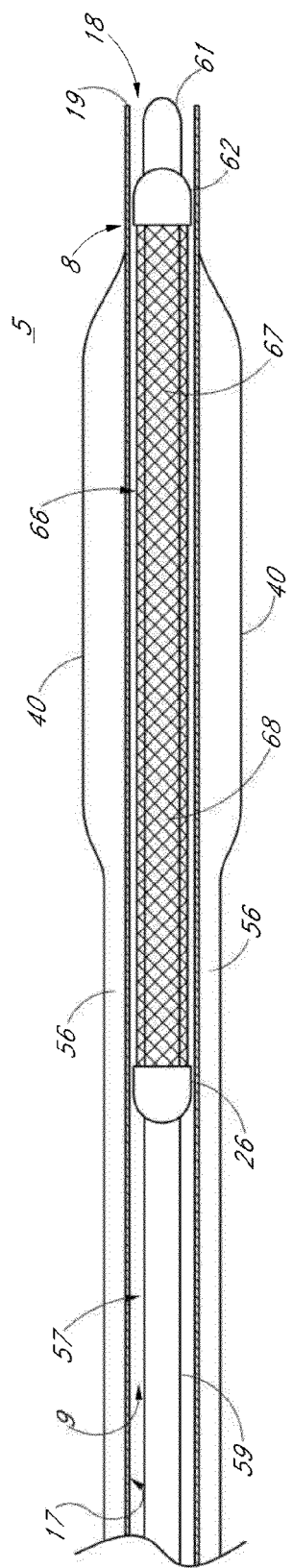
FIG. 64 is a cutaway view of a catheter carrying a guidewire assembly loaded with a stent according to an embodiment of the disclosure.

FIG. 64 illustrates a system 5 for treating atherosclerosis and providing embolic protection according to embodiments described herein. The system 5 comprises a catheter 8, a guidewire assembly 57 within the catheter 8, and a stent 66 loaded onto the guidewire assembly 57. FIG. 64 shows a cutaway view of the catheter 8 with the guidewire assembly 57 within a lumen 9 of the catheter 8. The guidewire assembly 57, which is used to deploy the stent 66 in a blood vessel, is slidable received within the lumen 9 of the catheter 8.

The catheter 8 comprises an inflatable balloon 40 and one or more lumens 56 fluidly coupled to the balloon 40. The lumens 56 extend from the balloon 40 to a proximal portion of the catheter 8 (not shown), where inflation fluid can be injected into the lumens 56 through a fluid injection port to inflate the balloon 40 from a deflated state to an inflated state. FIG. 64 shows the balloon 40 in the deflated state. In some embodiments, the balloon 40 has a tubular shape that expands radially when inflated. In these embodiments, the lumen 9 carrying the guidewire assembly 57 runs through the balloon 40.

The catheter 8 has a distal opening 18 through which the guidewire assembly 57 can be advanced beyond the distal end 19 of the catheter 8 to deploy the stent in a blood vessel. The lumen 56 extends from the distal opening 18 to a proximal opening (not shown), through which the guidewire assembly 57 can be inserted into the catheter 8, as shown in FIG. 43.

The guidewire assembly 57 may have the same or similar structure as the guidewire assemblies described above. The guidewire assembly 57 comprises a delivery guidewire 59 having a flexible distal tip portion 61. The delivery guidewire 59 is configured to transmit torque from a proximal portion of the delivery guidewire 59 to the distal portion while being flexible so that the delivery guidewire 59 can bend along a tortuous path of a blood vessel. The guidewire assembly 57 also includes one or both of a distal retaining member 62 and a proximal retaining member 26, which are configured to retain the stent 66 therebetween and hold the stent 66 in position on the guidewire assembly 57. The distal and proximal retaining members 62 and 26 may be implemented using the distal and proximal retaining members illustrated in FIG. 49. For example, the distal retaining member 62 may be implemented using the distal retaining illustrated in FIG. 50 so that the distal end of the stent 66 can be released by rotating the distal retaining member 62 via the delivery guidewire 59. The guidewire assembly 57 may also comprise a support coil 70 (shown in FIG. 47) to support the delivery guidewire 59 on the delivery guidewire 59 and maintain the stent 66 in a ready to deploy state.

In some embodiments, the stent 66 is a self-expanding stent comprising a tubular lattice structure having a compressed state and an expanded state. The stent 66 includes a distal portion 67 and a proximal portion 68. The stent 66 is loaded onto the guidewire assembly 57 in the compressed state, as shown in FIG. 64. The stent 66 may be maintained in the compressed state within the catheter 8 by the inner surface 17 of the lumen 9 and the retaining members 62 and 26. The stent 66 is configured to automatically expand radially from the compressed state to the expanded stated when deployed in a blood vessel, as discussed in further detail below.

A procedure for treating atherosclerosis and preventing, reducing, or limiting embolization from the treatment is described below with reference to FIGS. 65-69 according to an embodiment of the disclosure. The procedure may be performed using the system 5 illustrated in FIG. 64.

Referring to FIG. 65, the catheter 8 is percutaneously introduced into a blood vessel 69 and advanced to a treatment site 53 in the blood vessel 69. The treatment site 53 may be characterized by a narrowing (stenotic) of the blood vessel 53 caused by plaque buildup due to atherosclerosis. The blood vessel 69 may be the carotid artery or other artery. In one embodiment, the stenotic region 54 at the treatment site 53 is treated using balloon angioplasty and stenting. Other forms of angioplasty may also be used.

The catheter 8 may guided to the treatment site 53 using fluoroscopic imaging, in which one or more radio-opaque markers (not shown) are placed on the distal portion of the catheter 8 to indicate a position of the catheter 8 in a fluoroscopic image. The catheter 8 may also be guided using other imaging techniques including ultrasound and magnetic resonance imaging. In one embodiment, the catheter 8 is positioned so that the balloon 40 of the catheter 8 is positioned within the stenotic region 54. At this stage, the balloon 40 is in the deflated state, as shown in FIG. 65.

After the catheter 8 is positioned at the treatment site 53, the guidewire assembly 57 is advanced through the distal opening 18 of the catheter 8. A distal portion 67 of the stent 66 is advanced beyond the distal end 19 of the catheter 8 while a proximal portion 68 of the stent 66 remains within the lumen 9 of the catheter 8. The distal portion of the stent 66 is positioned downstream or distally from the stenotic region 54. The direction of blood flow through the blood vessel is indicated by the arrows in FIG. 65.

Referring to FIG. 66, the distal end of the stent 66 is released, allowing the distal portion 67 of the stent 66 to self expand. This may be done, for example, by rotating the distal retaining member 62 or other mechanism. A portion of the distal portion 67 of the stent 66 contacts the vessel wall 55 in the expanded state. The proximal portion of the 68 within the catheter 8 remains in the compressed state. In this configuration, the distal portion 67 of the stent 66 forms a filter between the vessel wall 55 and the distal end 19 of the catheter 8 for capturing plaque debris.

Pores in the lattice structure of the stent 66 allow blood to flow through the distal portion 67 of the stent 66 while capturing plaque debris. Thus, the stent 66 is partially deployed in the blood vessel 69 to act as a filter for preventing or limiting embolization while allowing blood flow. In some embodiments, the porosity of the filter formed by the distal portion 67 of the stent 66 can be adjusted after the distal portion 67 is deployed. For example, the distal portion 67 of the stent 66 may be compressed axially to increase the lattice density and hence decrease the porosity of the distal portion 67 of the stent 66. This may be done to filter smaller plaque debris. In another example, the distal portion 67 of the stent 66 may be expanded axially to decrease the lattice density and hence increase the porosity of the distal portion 67 of the stent 66. This may be done to allow greater blood flow through the filter. FIG. 36B shows examples of axial compression and axial expansion of a stent to adjust porosity of the stent.

The distal portion 67 of the catheter 8 may be compressed axially by advancing the distal end 18 of the catheter 8 after the distal portion 67 is deployed in the blood vessel 69. Advancement of the catheter 8 causes the distal end 19 of the catheter 8 to engage and apply a compressive force on the distal portion 67 in the axial direction. Alternatively, the distal portion 67 of the stent 66 may be compressed axially by advancing the guidewire assembly 57 after the distal portion 67 is deployed in the blood vessel 67. Advancement of the guidewire assembly 57 causes the proximal retaining member 26 to apply a compressive force on the stent 66 in the axial direction. In both implementations, contact between the distal portion 67 of the stent 66 and the vessel wall 55 holds the stent 66 in place during axial compression.

The stent 66 may be partially deployed in the blood vessel 69 to form the filter using other techniques. For example, the distal end 19 of the catheter 8 may be advanced to a position in the blood vessel 69 distal from the stenotic region 54. The catheter 8 may then be retracted relative to the guidewire assembly 57 to uncover the distal portion 67 of the stent 66. In this example, the stent 66 may be retained in the compressed state by the lumen 9 of the catheter so that the distal portion 67 of the stent 66 automatically expand when the catheter 8 is retracted. In another example, a pusher 50 that engages the proximal end of the stent 66 (shown in FIG. 5) may be used to partially deploy the stent 66 by pushing the distal portion 67 of the stent 66 out of the distal opening 18 of the catheter 8.

Figure 67:
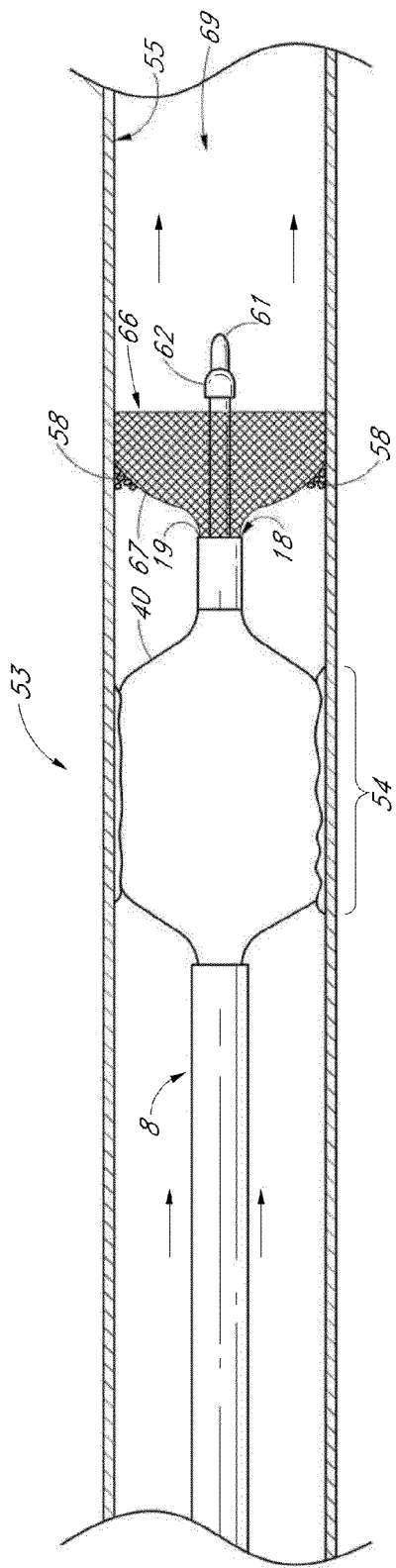
FIG. 67 illustrates an example of a balloon inflated in the blood vessel to treat a stenotic region with the partially deployed stent acting as a filter to capture plaque debris from the treatment.

Referring to FIG. 67, the balloon 40 is expanded radially to the expanded state by the injection of fluid into the balloon 40 through the lumens 56 (shown in FIG. 64). The expansion of the balloon 40 causes the balloon 40 to compresses the plaque in the stenotic region 54 against the vessel wall 55, thereby increasing the diameter of the blood vessel 69 in the stenotic region 54. During treatment, the distal portion 67 of the stent 66 captures plaque debris 58 released from the treatment. The capture of the plaque debris 58 limits the plaque debris from traveling downstream to smaller blood vessels and blocking blood to the smaller blood vessels.

Figure 68:
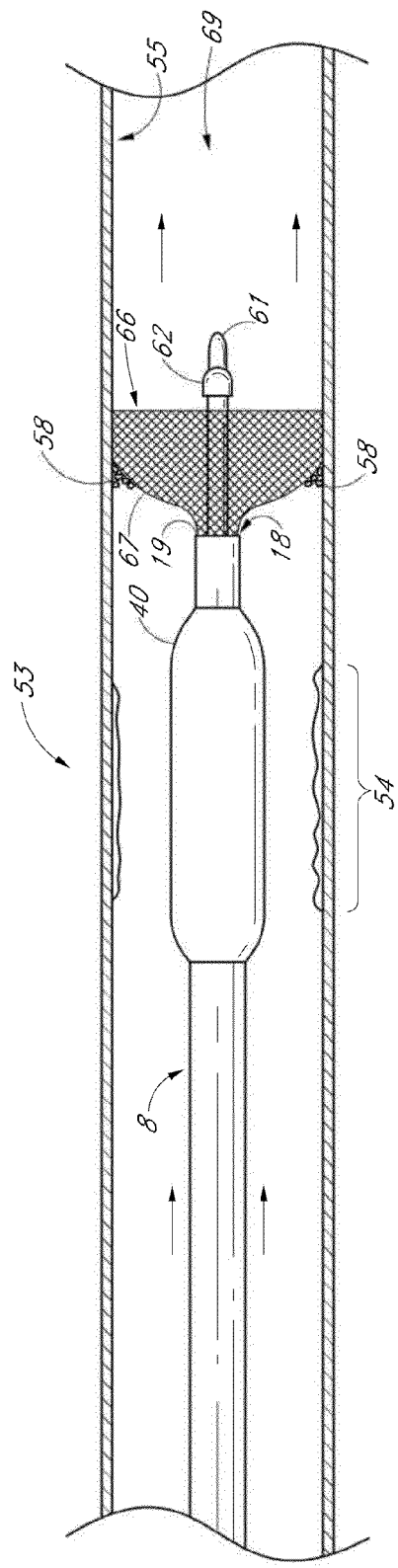
FIG. 68 illustrates an example of the balloon deflated back to a deflated state.

Referring to FIG. 68, the balloon 40 is deflated to the deflated state after the diameter of the blood vessel is increased. The plaque debris 58 released from the treatment are trapped in the distal portion 67 of the stent 66.

Figure 69:
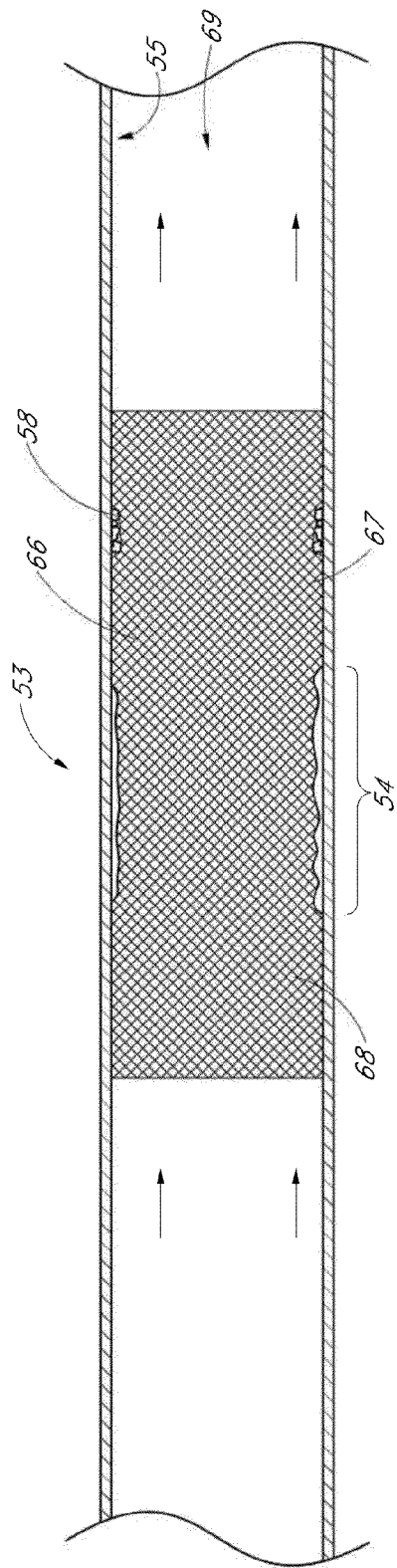
FIG. 69 illustrates an example of the stent fully deployed in the blood vessel.

Referring to FIG. 69, the catheter 8 is retracted relative to the stent 66 to fully deploy the stent 66 in the blood vessel 69, including the stenotic region 54. The rest of the stent 66 expands radially contacting the vessel wall 55. As shown in FIG. 69, the proximal end of the stent 66 extends to a location proximal to the stenotic region 54. After the stent 66 is fully deployed in the blood vessel 69, the catheter 8 and guidewire assembly 57 are withdrawn from the blood vessel 69. The plaque debris 58 and the remaining plaque in the stenotic region 54 are trapped between the stent 66 in the expanded state and the vessel wall 55. The stent 66 provides structural support to the vessel wall to strengthen the blood vessel 69 and prevent or reduce the likelihood of reclosure.

The atherosclerosis may be treated using other techniques, in which the distal portion of the stent 66 is deployed to provide embolic protection. For example, the plaque in the stenotic region 54 may be removed using a cutting tool mounted on the catheter 8, a laser beam emitted from a distal portion of the catheter 8, high energy signal emitted from one or more transducers or electrodes disposed on the catheter 8 and other techniques. For the example of a laser beam, the catheter may include an optical fiber for transporting the laser beam from a laser source to the distal portion of the catheter. In each of the these example techniques, the distal portion 67 of the stent 66 can be deployed as shown in FIG. 66 to capture plaque debris from the treatment.

FIG. 70 shows the catheter 8 with a cutting tool 73 for treating atherosclerosis instead of an angioplasty balloon according to some embodiments. In these embodiments, the cutting tool 73 is mounted on the outer surface of the catheter 8. FIG. 71 shows the cutting tool 73 comprising cutting blades orientated at an angle on the outer surface of the catheter 8. In these embodiments, the cutting tool 73 can be used to cut away plaque by rotating the cutting tool 73 while advancing the catheter 8 through the stenotic region 54. The cutting tool 73 may be rotated by rotating the catheter 8. The cutting tool 73 may have any shape capable of cutting away plaque. In addition, the cutting tool may have an abrasive surface.

In some embodiments, the cutting tool 73 comprises blades that are hinged to the catheter 8. This allows the blades to be folded downward along the circumference of the catheter 8 to more easily advance the catheter 8 through the blood vessel. The blades may be deployed by rotating the catheter 8 in one direction such that the centrifugal force of the rotation causes the blades to unfold. Additionally, the resistance of the fluid in which the blades are rotating can cause the blades to be deployed. The hinges may be configured so that the blades are orientated radially from the circumference of the catheter 8 when deployed. After plaque is removed, the catheter 8 may stop rotating or rotate in an opposite direction so that the blades fold back along the circumference of the catheter 8.

The catheter 8 may also include one or more aspiration lumens 71 and aspiration ports 74 for removing plaque debris released during treatment. In these embodiments, the distal portion 67 of the stent 66 may be deployed to capture plaque debris that are not removed through the aspiration ports 74.

Figure 72:
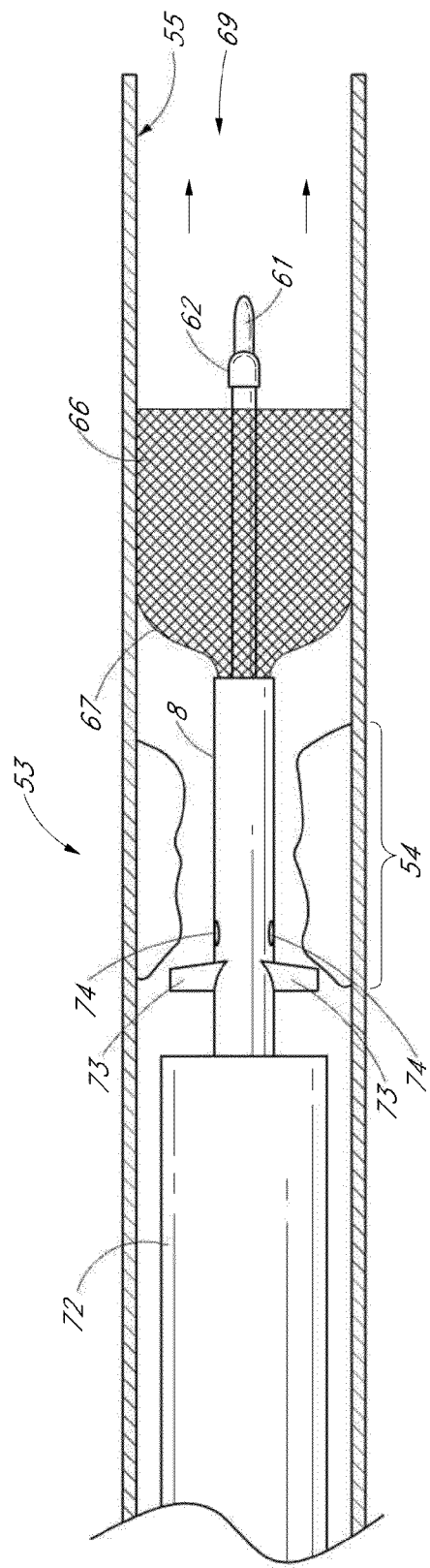
FIG. 72 illustrates an example of the cutting tool of the catheter being used to treat a stenotic region in a blood vessel with a partially deployed stent acting as a filter to capture plaque debris from the treatment.

A procedure for treating atherosclerosis and preventing or limiting embolization using the catheter 8 in FIGS. 70 and 71 is described below with reference to FIG. 72.

The catheter 8 is percutaneously introduced into a blood vessel 69 and advanced to the treatment site 53 in the blood vessel 69 with the cutting tool 73 located proximal to the stenotic region 54. In one embodiment, the catheter 8 is advanced to the treatment 53 through an outer catheter or sheath 72 in the blood vessel 69 to protect the blood vessel 69 from the cutting tool 73.

After the catheter 8 is positioned at the treatment site 53, the guidewire assembly 57 is advanced through the distal opening 18 of the catheter 8. The distal portion 67 of the stent 66 on the guidewire assembly 57 is advanced beyond the distal end 19 of the catheter 8 and deployed in the blood vessel 69, for example, by rotating the distal retaining member 62. The distal portion 67 of the stent forms a filter between the vessel wall 55 and the catheter 8 to capture plaque debris, as shown in FIG. 72. The resulting filter is located downstream or distal from the stenotic region 54.

After the distal portion 67 of the stent 66 is deployed, the cutting 73 can be used to cut away the plaque in the stenotic region 54. In one embodiment, the cutting tool 73 can be rotated and advanced through the stenotic region 54 to cut away plaque. In this embodiment, the stent 66 may be deployed with a large enough portion of the distal portion 67 contacting the vessel wall 55 so that a portion of the distal portion 67 still contacts the vessel wall 55 after the cutting tool 73 has been advanced through the stenotic region 54. After plaque has been cut away in the stenotic region 54, the catheter 8 can be withdrawn relative to the stent 66 to fully deploy the stent 66 in the blood vessel 69, as shown in FIG. 69.

Figure 73:
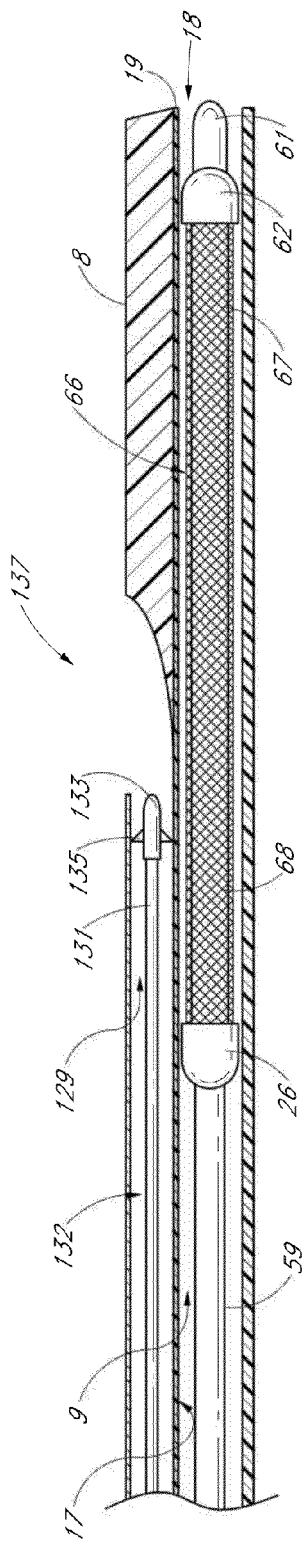
FIG. 73 is a cutaway view of a catheter carrying a guidewire assembly and a cutting tool according to embodiments disclosed herein.

FIG. 73 shows a catheter 8 with a cutting device 132 slidably received within a working lumen 129 of the catheter 8 according to some embodiments. In these embodiments, the cutting device 132 comprises a cutting tool 135 mounted on the distal tip 133 of a flexible drive shaft 131. The cutting tool 135 may comprise blades, an abrasive surface and/or a combination of both. To cut away plaque in a blood vessel, the cutting device 132 is advanced out of the catheter 8 through an opening 137. The opening 137 is positioned near the distal end 19 of the catheter 8.

Figure 74:
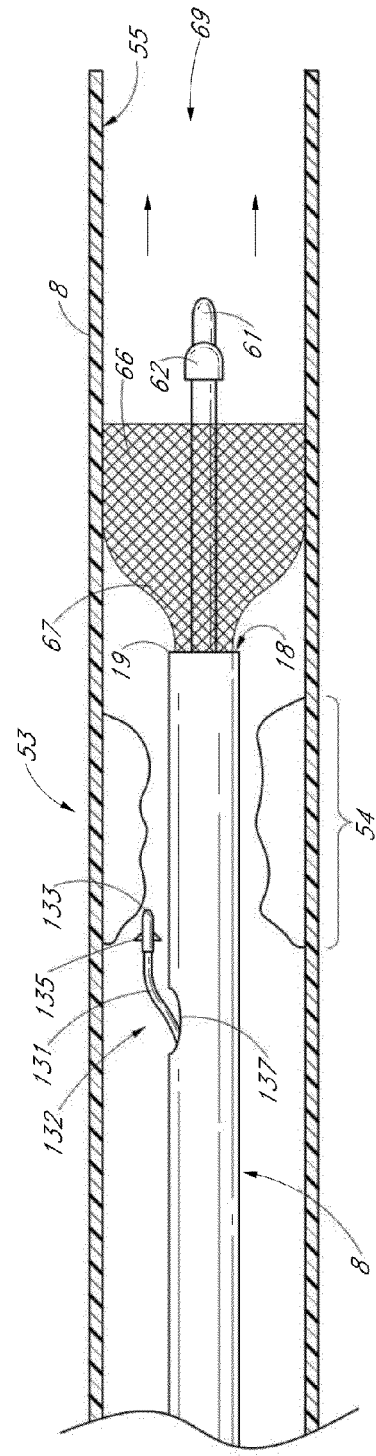
FIG. 74 illustrates an example of the catheter and the cutting tool positioned at a treatment site in a blood vessel.

FIG. 74 illustrates a procedure for treating atherosclerosis and preventing or limiting embolization using the cutting device 132 according to some embodiments. The catheter 8 is positioned at the stenotic region 54 and the distal portion 67 of the stent 66 is deployed in the blood vessel 69 to form a filter for trapping plaque debris. The cutting device 132 is then advanced through the opening 137 of the catheter 8 toward the plaque of the stenotic region 54. To cut away plaque, the drive shaft 131 rotates the cutting tool 135 and advances the cutting tool 135 through the stenotic region 54 as the cutting tool 135 rotates. The catheter 8 may also rotate slowly so that the cutting tool 135 can cut away plaque along the circumference of the blood vessel 69. As an alternative to rotating the cutting tool 135, the drive shaft 131 can move the cutting tool 135 back and forth to cut away plaque. In this example, the cutting tool 135 may comprise a plurality of blades disposed along the circumference of the distal top 133 and/or an abrasive surface.

After plaque has been cut away in the stenotic region 54, the cutting tool 135 can be withdrawn back into the catheter 8. The catheter 8 can then be withdrawn relative to the stent 66 to fully deploy the stent 66 in the blood vessel 69, as shown in FIG. 69.

The cutting device 132 may also be advanced into the blood vessel 69 separately from the catheter 8 instead of through the working lumen 129 of the catheter 8. FIG. 75 shows an example in which the cutting device 132 and the catheter 8 are advanced separately to the stenotic region 54 through an outer catheter or sheath 72 in the blood vessel 69. To cut away plaque, the drive shaft 131 may rotate the cutting tool 135 while advancing the cutting tool 135 through the stenotic region 54 and/or move the cutting tool 135 back and forth in the stenotic region 54. The cutting tool 135 may be moved around the catheter 8 to cut away plaque along the circumference of the blood vessel 69.

FIG. 76 shows a cutting tool 140 disposed on a catheter or sheath 142 separate from the catheter 8 used to deploy the stent 66 according to some embodiments. In these embodiments, the catheter 142 is advanced over the catheter 8 to the stenotic region 54. The catheter 142 includes a lumen (not shown) for receiving the catheter 8 therein as the catheter 142 is advanced over the catheter 8.

FIG. 76 illustrates a procedure for treating atherosclerosis and preventing or limiting embolization using the cutting device 132 according to some embodiments. The catheter 8 is positioned at the stenotic region 54 and the distal portion 67 of the stent 66 is deployed in the blood vessel 69 to form a filter for trapping plaque debris. The catheter 142 is advanced over the catheter 8 toward the plaque of the stenotic region 54. To cut away plaque, the cutting tool 140 may be rotated by rotating the catheter 142 over the catheter 8. The rotating cutting tool 104 may then be advanced through the stenotic region 54 by advancing the catheter 142 over the catheter 8 as the catheter 142 rotates. Alternatively, the cutting tool 140 may be moved back and forth in the stenotic region 54 to cut away plaque by moving the catheter 142 back and forth.

After plaque has been cut away in the stenotic region 54, the catheter 142 be can withdrawn through the outer catheter 72. The catheter 8 can then be withdrawn relative to the stent 66 to fully deploy the stent 66 in the blood vessel 69, as shown in FIG. 69.

In some embodiments, the cutting tool 140 comprises a blade wrapped along the circumference of the catheter 142 with a sharp edge facing distally. In these embodiments, the blade can cut away plaque around the circumference of the catheter 142 by advancing the catheter 142 through the stenotic region 54.

Figure 77:
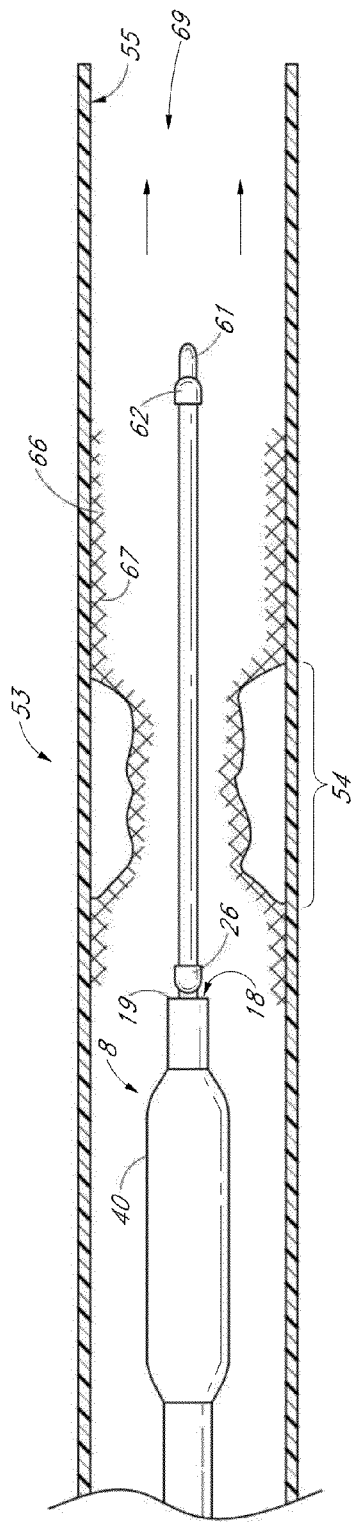
FIG. 77 illustrates an example of the stent deployed in a stenotic region of the blood vessel.

Referring to FIG. 77, in some embodiments, the stent 66 is deployed in the stenotic region 54 and in a region of the blood vessel 69 distal to the stenotic region 54 to prevent or limit embolization, as discussed below. The stent 66 may be deployed in the blood vessel 69 using the guidewire assembly 57 or other mechanism. FIG. 77 shows a cross-sectional view of the stent 66 in order to show devices positioned within the inner lumen of the stent 66. The deployed stent 66 contacts the vessel wall 55 in the region of the blood vessel 69 distal to the stenotic region 54 and plaque in the stenotic region 54. In these embodiments, the atherosclerosis may be treated using the catheter 8 shown in FIG. 64 or other catheter.

Figure 78:
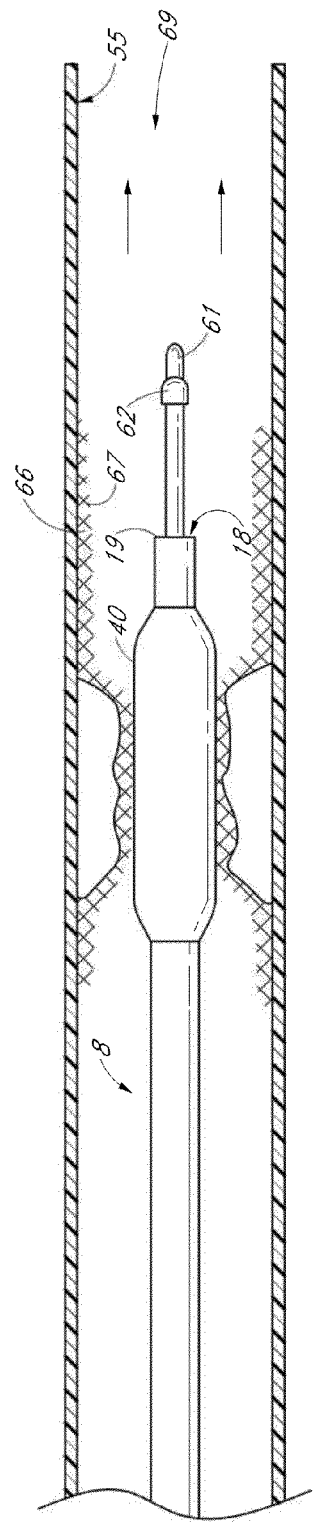
FIG. 78 illustrates an example of a balloon positioned within the deployed stent.
Figure 79:
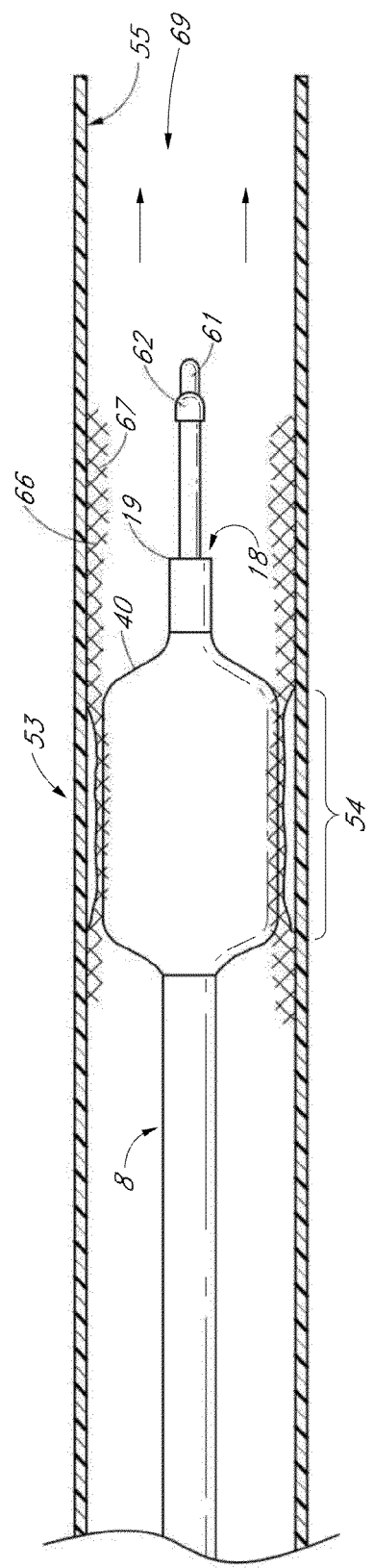
FIG. 79 illustrates an example of a balloon inflated within the deployed stent to treat the stenotic region.

In some embodiments, after the stent 66 is deployed, the balloon 40 of the catheter 8 is positioned within the stent 66 in the stenotic region 54 (shown in FIG. 78). The balloon 40 is then expanded radially to the expanded state by the injection of fluid into the balloon 40 through the lumens 56 (shown in FIG. 79). The expansion of the balloon 40 causes the balloon 40 to press radially against the inner surface of the stent 66. This in turn causes the stent 66 to compresses the plaque in the stenotic region 54 against the vessel wall 55, thereby increasing the diameter of the blood vessel 69 in the stenotic region 54. The portion of the stent 66 deployed distally from the stenotic region 54 facilitates the capture of plaque debris between the vessel wall 55 and the stent 66, thereby preventing or limiting embolization.

After the stenotic region 54 is opened, the balloon 40 is deflated to the deflated state and the catheter 8 is withdrawn from the blood vessel 69. The plaque remain trapped between the vessel wall 55 and the stent 66.

Figure 80:
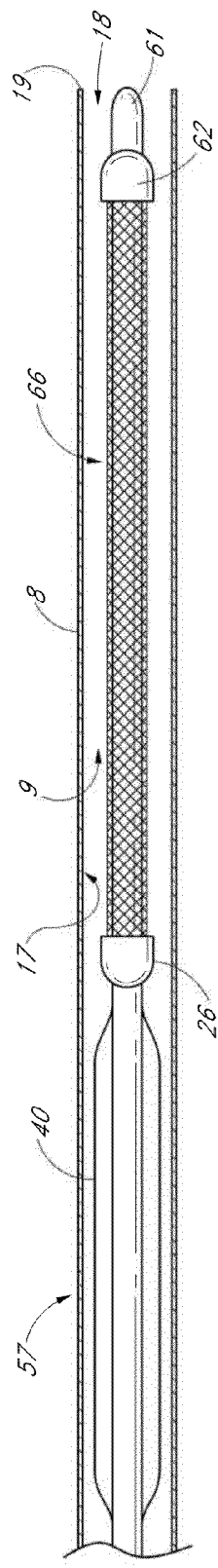
FIG. 80 is a cutaway view of a balloon disposed on a guidewire assembly according to embodiments disclosed herein.

The balloon 40 may be disposed on the guidewire assembly 57 instead of the catheter 8. FIG. 80 shows the balloon 40 disposed on the guidewire assembly 57 according to some embodiments. The balloon 40 is located proximal to the proximal retaining member 26. The guidewire assembly 57 includes one or more lumens (not shown) fluidly coupled to the balloon 40 for injecting inflation fluid into the balloon 40 to radially expand the balloon 40 from the deflated state (shown in FIG. 80) to the inflated stated.

Figure 81:
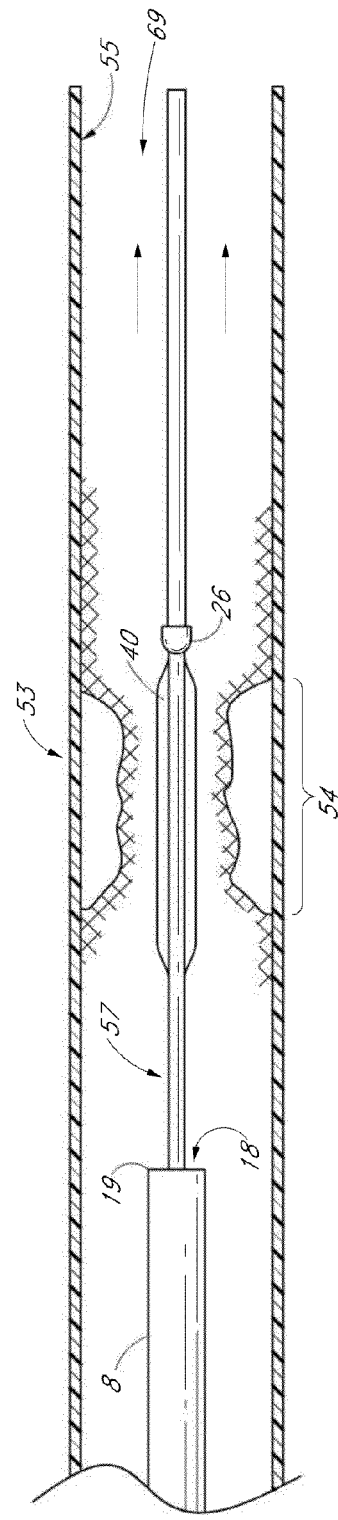
FIG. 81 illustrates an example of the stent deployed in a stenotic region of the blood vessel with the balloon on the guidewire assembly positioned within the deployed stent.

To treat atherosclerosis, the stent 66 is deployed in the stenotic region 54 and in a region of the blood vessel 69 distal to the stenotic region 54 to prevent or limit embolization, as discussed below. The stent 66 may be deployed in the blood vessel 69 using the guidewire assembly 57 (shown in FIG. 81) or other mechanism. FIG. 81 shows a cross-sectional view of the stent 66 in order to show devices positioned within the inner lumen stent 66.

Figure 82:
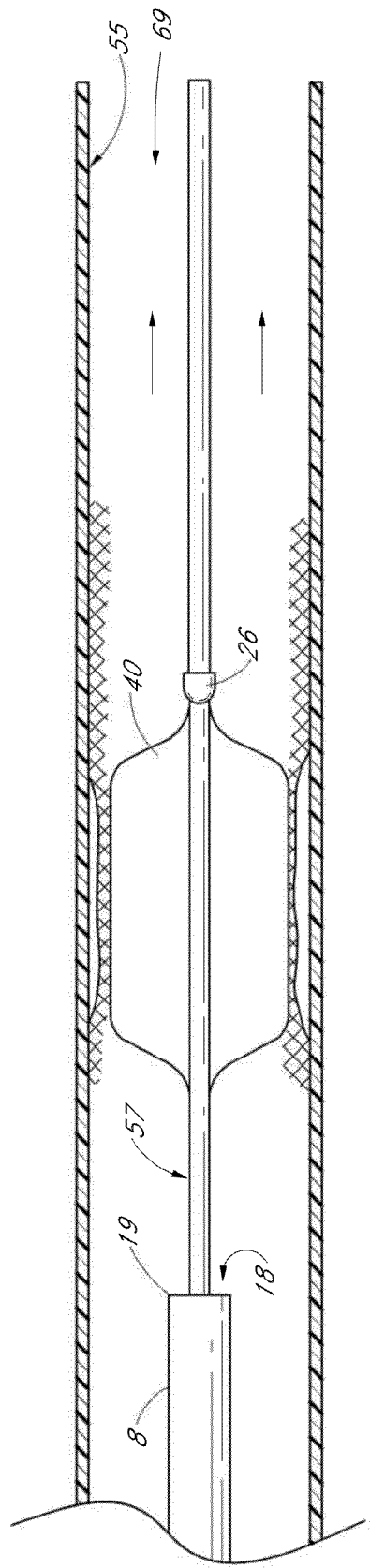
FIG. 82 illustrates an example of the balloon on the guidewire assembly inflated within the deployed stent to treat the stenotic region.

In some embodiments, after the stent 66 is deployed, the balloon 40 of the guidewire assembly 40 is positioned within the stent 66 in the stenotic region 54 (shown in FIG. 81). The balloon 40 is then expanded radially to the expanded state by the injection of fluid into the balloon 40 (shown in FIG. 82). The expansion of the balloon 40 causes the balloon 40 to press radially against the inner surface of the stent 66. This in turn causes the stent 66 to compresses the plaque in the stenotic region 54 against the vessel wall 55, thereby increasing the diameter of the blood vessel 69 in the stenotic region 54. The portion of the stent 66 deployed distally from the stenotic region 54 facilitates the capture of plaque debris between the vessel wall 55 and the stent 66, thereby preventing or limiting embolization.

After the stenotic region 54 is opened, the balloon 40 is deflated to the deflated state and the guidewire assembly 57 and the catheter 8 are withdrawn from the blood vessel. The plaque remain trapped between the vessel wall 55 and the stent 66.

In some embodiments, the expansive force of the stent 66 when deployed in the stenotic region 54 is sufficient to open the stenotic region 54. In these embodiments, the distal portion 67 of the stent 66 may be deployed in a region of the blood vessel 69 distal to the stenotic region 64. A portion of the stent 66 proximal to the distal portion 67 may then be deployed in the stenotic region 54. As the stent 66 expands radially in the stenotic region 54 during deployment, the expansive force of the stent 66 presses the plaque in the stenotic region 54 against the vessel wall 55, thereby increasing the diameter of the blood vessel in the stenotic region. Plaque is trapped between the vessel wall 55 and the stent 66. The portion of the stent 66 deployed distally from the stenotic region 54 facilitates the capture of plaque debris between the vessel wall 55 and the stent 66, thereby preventing or limiting embolization.

After the stent 66 is deployed in the blood vessel 69, plaque in the stenotic region 54 and plaque debris remain trapped between the vessel wall 55 and the stent 66. Overtime, neointima can build up over the inner surface of the stent 66. As a result, a new inner lining of the blood vessel 69 is formed over the inner surface of the stent 66, which facilitates the retention of plaque and plaque debris between the old inner lining of the blood vessel 69 and the stent 66.

In some embodiments, "occluding device" and "stent" are used interchangeably. In some embodiments, "cell" and "pore" are used interchangeably. In some embodiments, porosity refers to a value inversely proportional to lattice density.

The apparatus and methods discussed herein are not limited to the deployment and use of an occluding device within the vascular system but may include any number of further treatment applications. Other treatment sites may include areas or regions of the body such as organ bodies. Modification of each of the above-described apparatus and methods for carrying out the subject technology, and variations of aspects of the disclosure that are apparent to those of skill in the art are intended to be within the scope of the claims. Furthermore, no element, component or method step is intended to be dedicated to the public regardless of whether the element, component or method step is explicitly recited in the claims.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations which will be apparent to those skilled in the art may be made in the arrangement, operation and details of the method and apparatus of the subject technology disclosed herein without departing from the spirit and scope of the subject technology as defined in the appended claims. Therefore, the scope of the subject technology should be determined by the appended claims and their legal equivalents. Furthermore, no element, component or method step is intended to be dedicated to the public regardless of whether the element, component or method step is explicitly recited in the claims. Underlined and/or italicized headings and subheadings are used for convenience only, do not limit the subject technology, and are not referred to in connection with the interpretation of the description of the subject technology. In the claims and description, unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed by the claims.

What is claimed is:

1. A method, of treating an aneurysm in a vessel of a patient, comprising:
    expanding, in the vessel having the aneurysm, a first stent having a first stent proximal end and a first stent distal end, such that the first stent extends from a first location, proximal to the aneurysm, to a second location, distal to the aneurysm;
    expanding, within the first stent, a second stent having a second stent proximal end and a second stent distal end, such that when the second stent is expanded and engages the first stent, the second stent is axially positioned substantially adjacent to the aneurysm, and the second stent distal end is positioned proximal to the first stent distal end, thereby impeding blood flow from the vessel into the aneurysm, wherein the second stent proximal end is substantially coterminous with the first stent proximal end;
    applying an axially compressive force to a first portion of the first stent, the first portion overlying the aneurysm, whereby the first portion transitions from a first porosity to a second porosity, less than the first porosity, while (i) the first portion maintains a substantially constant cross-sectional dimension and (ii) wherein movement of a second portion of the first stent, distal to the first portion, is impeded by a frictional force applied by the first stent against a vessel wall distal to the aneurysm;
    wherein applying an axially compressive force to the first portion of the first stent causes a third portion, of the second stent, in contact with the first portion, to transition from a third porosity to a fourth porosity, less than the third porosity.

2. The method of claim 1, wherein blood flow through the first and second stents into the aneurysm is less than blood flow into the aneurysm would be through the first stent alone.

3. The method of claim 1, wherein the first stent and the second stent have, when unrestrained, substantially the same porosity.

4. The method of claim 1, wherein the axially compressive force is applied by an elongate member.

5. The method of claim 4, wherein the elongate member is a lattice density adjusting implement.

6. A method, of treating a saccular aneurysm in a vessel of a patient, comprising:
    expanding within the vessel a first stent such that the first stent extends from a first location distal to the saccular aneurysm of the vessel to a second location proximal to the saccular aneurysm; and
    expanding a second stent, within the first stent, such that a first end of the second stent is between the first location and a distal side of an ostium of the saccular aneurysm and a second end of the second stent is between the second location and a proximal side of the ostium;
    applying an axially compressive force to a first portion of the first stent, the first portion overlying the ostium, whereby the first portion transitions from a first porosity to a second porosity, less than the first porosity, while (i) the first portion maintains a substantially constant cross-sectional dimension and (ii) wherein movement of a second portion of the first stent, distal to the first portion, is impeded by a frictional force applied by the first stent against a vessel wall distal to the ostium;
    wherein applying an axially compressive force to the first portion of the first stent causes a third portion, of the second stent, in contact with the first portion, to transition from a third porosity to a fourth porosity, less than the third porosity.

7. The method of claim 6, wherein the first stent and the second stent have, when unrestrained, substantially the same porosity.

8. The method of claim 6, wherein blood flow through the first and second stents into the saccular aneurysm is less than blood flow into the aneurysm would be through the first stent alone.

9. The method of claim 6, wherein the axially compressive force is applied by an elongate member.

10. The method of claim 9, wherein the elongate member is a lattice density adjusting implement.

11. A method, of treating a saccular aneurysm in a vessel of a patient, comprising:
- expanding a first stent such that the first stent extends within the vessel from a first location, distal to a distal-most side of the saccular aneurysm, to a second location, proximal to a proximal-most side of the saccular aneurysm; and
- expanding a second stent, within the first stent, such that the second stent extends from a third location, between the first location and the distal-most side of the saccular aneurysm, to a fourth location, between the second location and the proximal-most side of the saccular aneurysm;
- applying an axially compressive force to a first portion of the first stent, the first portion overlying the saccular aneurysm, whereby the first portion transitions from a first porosity to a second porosity, less than the first porosity, while (i) the first portion maintains a substantially constant cross-sectional dimension and (ii) wherein movement of a second portion of the first stent, distal to the first portion, is impeded by a frictional force applied by the first stent against a vessel wall distal to the saccular aneurysm;
- wherein applying an axially compressive force to the first portion of the first stent causes a third portion, of the second stent, in contact with the first portion, to transition from a third porosity to a fourth porosity, less than the third porosity.

12. The method of claim 11, wherein the first stent and the second stent have, when unrestrained, substantially the same porosity.

13. The method of claim 11, wherein blood flow through the first and second stents into the saccular aneurysm is less than blood flow into the aneurysm would be through the first stent alone.

14. The method of claim 11, wherein the axially compressive force is applied by an elongate member.

15. The method of claim 14, wherein the elongate member is a lattice density adjusting implement.

\* \* \* \* \*